United States Patent
Honda et al.

(10) Patent No.: US 10,233,146 B2
(45) Date of Patent: Mar. 19, 2019

(54) ACETYLENIC CYANOENONES AS THERAPEUTICS FOR INFLAMMATION AND CARCINOGENESIS

(71) Applicants: Tadashi Honda, Port Jefferson Station, NY (US); Wei Li, Albuquerque, NM (US); Suqing Zheng, Wenzhou (CN); Albena Dinkova-Kostova, Dundee (GB)

(72) Inventors: Tadashi Honda, Port Jefferson Station, NY (US); Wei Li, Albuquerque, NM (US); Suqing Zheng, Wenzhou (CN); Albena Dinkova-Kostova, Dundee (GB)

(73) Assignees: THE RESEARCH FOUNDATION FOR THE STATE UNIVERSITY OF NEW YORK, Albany, NY (US); UNIVERSITY OF DUNDEE, Dundee (GB)

( * ) Notice: Subject to any disclaimer, the term of this patent is extended or adjusted under 35 U.S.C. 154(b) by 0 days.

(21) Appl. No.: 15/565,846

(22) PCT Filed: Apr. 14, 2016

(86) PCT No.: PCT/US2016/027514
§ 371 (c)(1),
(2) Date: Oct. 11, 2017

(87) PCT Pub. No.: WO2016/168450
PCT Pub. Date: Oct. 20, 2016

(65) Prior Publication Data
US 2018/0134654 A1  May 17, 2018

Related U.S. Application Data

(60) Provisional application No. 62/148,491, filed on Apr. 16, 2015.

(51) Int. Cl.
*A61K 31/415* (2006.01)
*C07C 255/46* (2006.01)
(Continued)

(52) U.S. Cl.
CPC .......... *C07C 255/46* (2013.01); *A61K 31/277* (2013.01); *A61P 25/28* (2018.01);
(Continued)

(58) Field of Classification Search
CPC .................................................... C07D 233/64
(Continued)

(56) References Cited

U.S. PATENT DOCUMENTS 7,714,012 B2 * 5/2010 Honda ................. C07C 49/743
514/231.2
8,067,394 B2 * 11/2011 Honda ................. C07C 49/743
514/400
(Continued)

FOREIGN PATENT DOCUMENTS

WO   WO 2008/064132 A2   5/2008
WO   WO 2008/064133 A1   5/2008
(Continued)

OTHER PUBLICATIONS

Zheng et al. CAS: 156: 666077, 2012.*
(Continued)

*Primary Examiner* — Rei Tsang Shiao
(74) *Attorney, Agent, or Firm* — Gary J. Gershik; Cooper & Dunham LLP

(57) ABSTRACT

The present invention provides a compound having the structure:

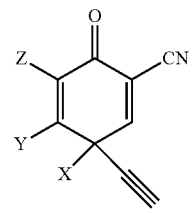

wherein
X is $C_1$-$C_{12}$ alkyl, $C_2$-$C_{12}$ alkenyl, $C_2$-$C_{12}$ alkynyl, cyano, aryl, heteroaryl, alkylaryl, alkylheteroaryl, alkenylaryl, alkenylheteroaryl, alkynylaryl, alkynylheteroaryl, alkoxy, alkenyloxy, alkynyloxy, aryloxy, heteroaryloxy, acyl, alkylhydroxy, alkylamino, alkenylamino, alkynylamino, amido, carboxyl, or carboxyl ester, or forms an unsubstituted or substituted cyclobutyl, cyclopentyl, cyclohexyl, cycloheptyl, indane or tetralin with Y,
Y is H or forms an unsubstituted or substituted cyclobutyl, cyclopentyl, cyclohexyl, cycloheptyl, indane or tetralin with X, or forms an unsubstituted or substituted monocycle with Z; and
Z is H or forms an unsubstituted or substituted monocycle with Y;
wherein when X and Y are both H, then X is $C_2$ alkenyl or $C_2$ alkynyl, and when Y is H forms a substituted cyclohexyl, cycloheptyl with X, the cyclohexyl is other than a trisubstituted
cyclohexyl bearing $CH_3$, i-Pr and $(CH_2)_2CO_2CH_3$ groups or $CH_3$, i-Pr and $(CH_2)_3NH_2$,
or a salt or ester thereof.

23 Claims, 6 Drawing Sheets

(51) Int. Cl.
    A61K 31/277     (2006.01)
    C07C 255/47     (2006.01)
    A61P 25/28      (2006.01)
    A61P 29/00      (2006.01)
    A61P 35/00      (2006.01)
(52) U.S. Cl.
    CPC .............. *A61P 29/00* (2018.01); *A61P 35/00* (2018.01); *C07C 255/47* (2013.01); *C07C 2601/16* (2017.05); *C07C 2602/10* (2017.05); *C07C 2602/24* (2017.05); *C07C 2603/18* (2017.05); *C07C 2603/26* (2017.05)
(58) Field of Classification Search
    USPC .................................................. 514/400, 520
    See application file for complete search history.

(56) References Cited

U.S. PATENT DOCUMENTS

| | | | |
|---|---|---|---|
| 8,314,137 B2* | 11/2012 | Honda | C07C 255/46 514/400 |
| 9,000,188 B2* | 4/2015 | Honda | C07C 255/46 548/335.1 |
| 2013/0274480 A1 | 10/2013 | Honda et al. | |

FOREIGN PATENT DOCUMENTS

| WO | WO2010/011782 | * | 1/2010 |
|---|---|---|---|
| WO | WO 2010/011782 A1 | | 1/2010 |
| WO | WO 2013/078371 A2 | | 5/2013 |
| WO | WO 2014/151181 A1 | | 9/2014 |

OTHER PUBLICATIONS

Or Zhang et al. CAS: 157:373488, 2011.*
Clinton, R. O. et al. Steroidal[3,2-c]pyrazoles. II. Androstanes, 19-norandrostanes and their unsaturated analogs. J. Am. Chem. Soc. 1961, 83, 1478-1491.
Fahey, J. W. et al. The "Prochaska" microtiter plate bioassay for inducers of NQO1. Methods Enzymol. 2004, 382, 243-258.
Gold, R. et al. Placebo-controlled phase 3 study of oral BG-12 for relapsing multiple sclerosis. N. Engl. J. Med. 2012, 367, 1098-1107.
Hulme, A. N.; Meyers, A. I. Asymmetric synthesis of 1,1-disubstituted tetralins and dihydronaphthalenes by diastereoselective addition of lithiosilanes to chiral naphthalenes. J. Org. Chem. 1994, 59, 952-953.
Johnson, W. S.; Shelberg, W. E. A plan for distinguishing between some five- and six-membered ring ketones. J. Am. Chem. Soc. 1945, 67, 1745-1754.
Justribó, V. et al. Studies on the intramolecular cyclizations of bicyclic □-hydroxynitriles promoted by triflic anhydride. J. Org. Chem. 2007, 72, 3702-3712.
Liotta, D. et al. III. A simple method for the efficient synthesis of unsaturated □-dicarbonyl compounds. J. Org. Chem. 1981, 46, 2920-2923.
Miller, R. A. et al. Electrophilic fragment-based design of reversible covalent kinase inhibitors. J. Am. Chem. Soc. 2013, 135, 5298-5301.
Nareddy, P. et al. Atropoisomeric (P,N) ligands for the highly enantioselective Pd-catalysed intramolecular asymmetric α-arylation of α-branched aldehydes. Angew. Chem. Int. Ed. 2012, 51, 3826-3831.
Nguyen, P. et al. A convenient synthesis of 7-halo-indanones and 8-halo-1-tetralones. J. Org. Chem. 2003, 68, 10195-10198.
Nguyen, H. N. et al. The first general palladium catalyst for the Suzuki-Miyaura and carbonyl enolate coupling of aryl arenesulfonates. J. Am. Chem. Soc. 2003, 125, 11818-11819.
Suh, N. et al. Novel triterpenoids suppress inducible nitric oxide synthase (iNOS) and inducible cyclooxygenase (COX-2) in mouse macrophages. Cancer Res. 1998, 58, 717-723.

Taylor, S. K. et al. Friedel-Crafts cyclialkylations of some epoxides. 3. Cyclizations of tertiary and meta-substituted arylalkyl epoxides. J. Org. Chem. 1988, 53, 3309-3312.
Vedejs, E. et al. A comparison of monocyclic and bicyclic phospholanes as acyl-transfer catalysts. J. Org. Chem. 2003, 68, 5020-5027.
Walker, S. D. et al. A rationally designed universal catalyst for Suzuki-Miyaura coupling processes. Angew. Chem. Int. Ed. 2004, 43, 1871-1876.
Dinkova-Kostova, A. T. et al. An exceptionally potent inducer of cytoprotective enzymes: elucidation of the structural features that determine inducer potency and reactivity with Keap1. J. Biol. Chem. 2010, 285, 33747-33755.
Brown, D. S. et al. Epoxidation with dioxiranes derived from 2-fluoro-2-substituted-1-tetralones and 1-indanones. Tetrahedron 1995, 51, 3587-3606.
Corey, E. J.; Ruden, R. A. Stereoselective methods for the synthesis of terminal cis and trans enyne units. Tetrahedron Lett. 1973, 1495-1499.
Dinkova-Kostova, A. T.; Kostov R. V. Glucosinolates and isothiocyanates in health and disease. Trends Mol. Med. 2012, 18, 337-347.
Fearnley, S. P. et al. Preparation of 2-alkyl- and 2-acylpropenals from 5-(trifluoromethanesulfonyloxy)-4H-1,3-dioxin: a versatile acrolein α-cation synthon. Tetrahedron 2000, 56, 10275-10281.
Honda, T. et al. Synthesis and biological evaluation of 1-[2-Cyano-3,12-dioxooleana-1,9(11)-dien-28-oyl]-4-ethynylimidazole. A novel and highly potent anti-inflammatory and cytoprotective agent. Bioorg. Med. Chem. Lett. 2011, 21, 2188-2191.
Kahne, D.; Collum, D. B. Kinetic cyanations of ketone enolates. Tetrahedron Lett. 1981, 22, 5011-5014.
Liu, H. et al. Coordinate regulation of enzyme markers for inflammation and for protection against oxidants and electrophiles. Proc. Natl. Acad. Sci. USA 2008, 105, 15926-15931.
Mella, M. et al. 1,2-Dideoxy-3,4:5,7-bis-O-(1-methylethylidene)-D-gluco- and D-galacto-hept-1-ynitols: synthesis and conformational studies. Tetrahedron 1988, 44, 1673-1678.
Murakata, M. et al. Synthesis of (R)-(−)-3-methoxymethyl-3-propyl-3,4-dihydrocoumarin from a chiral Michael adduct: Absolute configulation of the allylated products of enatioselective radical-mediated reactions. Chem. Pharm. Bull. 1999, 47, 1380-1383.
Muzart J. Synthesis of unsaturated carbonyl compounds via a chromium-mediated allylic oxidation by 70% tert-butylhydroperoxide. Tetrahedron Lett. 1987, 28, 4665-4668.
Noji, M. et al. A novel synthetic route of 2-arylalkanoic acids by a ruthenium-catalysed chemoselective oxidation of furan rings. Synthesis, 2008, 3835-3845.
Shirakawa, S.; Shimizu, S. Hydrogen-bond-promoted C—C bond-forming reaction: Catalyst-free Michael addition reactions in ethanol. Synlett 2007, 3160-3164.
Zhang Y. et al. A major inducer of anticarcinogenic protective enzymes from broccoli: isolation and elucidation of structure. Proc. Natl. Acad. Sci. USA, 1992, 89, 2399-2403.
Zheng, S. et al. Microwave-assisted Diels-Alder reactions between Danishefsky's diene and derivatives of ethyl α-(hydroxymethyl)acrylate. Synthetic approach towards a biotinylated anti-inflammatory monocyclic cyanoenone. Tetrahedron 2013, 69, 2052-2055.
Prochaska, H. J. and Santamaria A. B. Direct measurement of NAD(P)H:quinone reductase from cells cultured in microtiter wells: a screening assay for anticarcinogenic enzyme inducers. Anal. Biochem. 1988, 169, 2, 328-336.
Ohira, S. Methanolysis of Dimethyl (1-Diazo-2-oxopropyl) Phosphonate: Generation of Dimethyl (Diazomethyl) Phosphonate and Reaction with Carbonyl Compounds. Synthetic Communications, 2006, 19, 561-564.
International Search Report dated Jul. 18, 2016 in connection with PCT International Application No. PCT/US2016/027154.
Written Opinion of the International Searching Authority dated Jul. 18, 2016 in connection with PCT International Application No. PCT/US2016/027154.
Zheng, S. et al. "Synthesis, Chemical Reactivity as Michael Acceptors, and Biological Potency of Monocyclic Cyanoenones, Novel and Highly Potent Anti-inflammatory and Cytoprotective Agents", J. Med. Chem., 2012, 55(10), pp. 4837-4846.

(56) References Cited

OTHER PUBLICATIONS

Dinkova-Kostova, A. et al. "An Exceptionally Potent Inducer of Cytoprotective Enzymes: Elucidation of the Structural Features that Determine Inducer Potency and Reactivity with Keap1", J. Biol. Chem., 2010, 285(44), pp. 33747-33755.

Li, et al. "New Monocyclic, Bicyclic, and Tricyclic Ethynylcyanodienones as Activators of the Keap1/Nrf2/ARE Pathway and Inhibitors of Inducible Nitric Oxide Synthase", J. Med. Chem., 2015, 58(11), pp. 4738-4748.

Honda, T. et al. "Tricyclic Compounds Containing Nonenolizable Cyano Enones. A Novel Class of Highly Potent Anti-Inflammatory and Cytoprotective Agents", J. Med. Chem., 2011, 54(6), pp. 1762-1778.

Honda, T. et al. "Novel Tricyclic Compounds Having Acetylene Groups at C-8a and Cyano Enones in Rings A and C: Highly Potent Anti-inflammatory and Cytoprotective Agents", J. Med. Chem., 2007, 50(8), pp. 1731-1734.

Onyango, E.O. et al. "Synthesis of a Dicyano Abietane, a Key Intermediate for the Anti-inflammatory Agent TBE-31", Org. Lett., 2014, 16(1), pp. 322-324.

Saito, A. et al. "Synthesis and biological evaluation of biotin conjugates of (±)-(4bS,8aR,10aS)-10a-ethynyl-4b,8,8-trimethyl-3,7-dioxo-3,4b,7,8,8a,9,10,10a-octahydro-phenanthrene-2,6-dicarbonitrile, an activator of the Keap1/Nrf2/ARE pathway, for the isolation of its protein targets", Bioorganic & Medicinal Chemistry Letters, 2013, 23(20), pp. 5540-5543.

Zheng, S. et al. "(±)-(4bS,8aR,10aS)-10a-Ethynyl-4b,8,8-trimethyl-3,7-dioxo-3,4b,7,8,8a,9,10,—10a-octahydrophenanthrene-2,6-dicarbonitrile", Acta Crystallographica, Section E: Structure Reports Online, 2012, 68(11), o3095-o3096.

Kalra, S. et al. "Highly Potent Activation of Nrf2 by Topical Tricyclic Bis(Cyano Enone): Implications for Protection against UV Radiation during Thiopurine Therapy", Cancer Prevention Research, 2012, 5(7), pp. 973-981.

Zhang, Y. et al. "HSF1-Dependent Upregulation of Hsp70 by Sulfhydryl-Reactive Inducers of the KEAP1/NRF2/ARE Pathway", Chemistry & Biology, 2011, 18(11), pp. 1355-1361, Cambridge, MA, United States.

Liby, K. et al. "A Novel Acetylenic Tricyclic bis-(Cyano Enone) Potently Induces Phase 2 Cytoprotective Pathways and Blocks Liver Carcinogenesis Induced by Aflatoxin", Cancer Research, 2008, 68(16:, pp. 6727-6733.

Saito, A. et al. "An Improved Synthesis of a Hydroxymethyl Tricyclic Ketone from Cyclohexanone, the Key Processes for the Synthesis of a Highly Potent Anti-inflammatory and Cytoprotective Agent", Synthesis, 2013, 45(23), pp. 3251-3254.

Structure Search prepared Feb. 27, 2015 by SCIENCEIP: The CAS Search Service, Science IP Order 3104233.

* cited by examiner

ACETYLENIC CYANOENONES AS THERAPEUTICS FOR INFLAMMATION AND CARCINOGENESIS

CROSS-REFERENCE TO RELATED APPLICATIONS

This application is a § 371 national stage of PCT International Application No. PCT/US2016/027514, filed Apr. 14, 2016, claiming the benefit of U.S. Provisional Application No. 62/148,491, filed Apr. 16, 2015.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Tricyclic compound 1 [TBE-31, (±)-(4bS,8aR,10aS)-10a-ethynyl-4b,8,8-trimethyl-3,7-dioxo-3,4b,7,8,8a,9,10, 10a-octahydrophenanthrene-2,6-dicarbonitrile, FIG. 1] is one of the most potent activators of the Keap1/Nrf2/ARE pathway known to date (Honda, T. et al. 2007; Honda, T. et al. 2011; Liby, K. et al. 2008; Dinkova-Kostova, A. T, et al. 2010). Tricyclic compound 1 suppresses pro-inflammatory responses and induces heme oxygenase-1 (HO-1) in RAW264.7 cells, and upregulates NAD(P)H: quinone oxidoreductase 1 (NQO1) in Hepa1c1c murine hepatoma cells through the Keap1/Nrf2/ARE pathway (Honda, T. et al. 2011). Incorporation of small quantities (9.2 mg per kg of food) of 1 in the diet of mice profoundly and dose-dependently induces NQO1 and glutathione S-transferases in the stomach, skin, and liver (Dinkova-Kostova, A. T. et al. 2010). Long-term (five days per week for four weeks) topical daily applications of 200 nmol of 1 causes a robust systemic induction of the Keap1/Nrf2/ARE pathway and decreases the 6-thioguanine incorporation into DNA of skin, blood, and liver of azathioprine-treated mice, indicating extraordinary bioavailability and efficacy (Kalra, S. et al. 2012). Tricyclic compound 1 has two different monocyclic nonenolizable cyanoenones 2 and 3 (FIG. 1) in rings A and C. It has been chemically demonstrated that rings A and C of TBE-31 give reversible Michael adducts with the sulfhydryl groups of Keap1 and dithiothreitol (DTT) by UV spectroscopy studies (Liby, K. et al. 2008; Dinkova-Kostova, A. T. et al. 2010).

Generally, there are three categories of drugs: (1) Irreversible covalent drugs, which permanently bind with protein targets through covalent bonds. This category includes alkylating agents (e.g., cyclophosphamide, mitomycin C), β-lactam antibiotics (e.g., penicillin, cephalosporin) and irreversible enzyme inhibitors (e.g., acetylsalicylic acid, omeprazole); (2) Reversible non-covalent drugs, which noncovalently (e.g., hydrogen bond, hydrophobic effect and Van der Waals forces) bind with protein targets. This category contains receptor antagonists (for example, angiotensin II receptor blocker, β-blockers, and histamine $H_2$-receptor antagonists etc.); and (3) Reversible covalent drugs, which covalently bind but not permanently with protein targets. This final category is a new category. Currently, dimethyl fumarate (DMF) (Gold, R. et al. 2012), which is a Michael acceptor and an activator of the Keap1/Nrf2/ARE pathway, is the only drug that is clinically used for the treatment of multiple sclerosis. CDDO and bardoxolone methyl also belong to this category. Recently, the development of a series of reversible covalent inhibitors of MSK/RSK-family kinases has been reported (Miller, R. A. et al. 2013).

Although irreversible covalent drugs have long duration of action, high potency and high ligand efficiency, because they irreversibly bind to both on- and off-protein targets, there is a potential for immune-mediated hypersensitivity and therefore they are not suitable for chronic dosing. Reversible non-covalent drugs do not form permanent adducts and therefore are suitable for chronic dosing. However, their selectivity and potency are moderate because their ligand efficiency is usually poor. To the contrary, reversible covalent drugs have high potency, high ligand efficiency and long duration of action and because they do not form permanent adducts, they are suitable for chronic dosing. Overall, reversible covalent drugs combine the advantages and circumvent the disadvantage of irreversible covalent and reversible non-covalent drugs. Nevertheless, reversible covalent drugs have been largely ignored because of the lack of reactive compounds to produce the reversible covalent adducts with protein targets.

SUMMARY OF THE INVENTION

The present invention provides a compound having the structure:

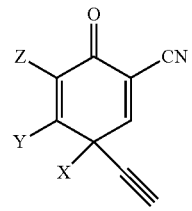

wherein
X is $C_1$-$C_{12}$ alkyl, $C_2$-$C_{12}$ alkenyl, $C_2$-$C_{12}$ alkynyl, cyano, aryl, heteroaryl, alkylaryl, alkylheteroaryl, alkenylaryl, alkenylheteroaryl, alkynylaryl, alkynylheteroaryl, alkoxy, alkenyloxy, alkynyloxy, aryloxy, heteroaryloxy, acyl, alkylhydroxy, alkylamino, alkenylamino, alkynylamino, amido, carboxyl, or carboxyl ester, or forms an unsubstituted or substituted cyclobutyl, cyclopentyl, cyclohexyl, cycloheptyl, indane or tetralin with Y, Y is H or forms an unsubstituted or substituted cyclobutyl, cyclopentyl, cyclohexyl, cycloheptyl, indane or tetralin with X, or forms an unsubstituted or substituted monocycle with Z; and Z is H or forms an unsubstituted or substituted monocycle with Y;

wherein when X and Y are both H, then X is $C_2$ alkenyl or $C_2$ alkynyl, and when Y is H forms a substituted cyclohexyl, cycloheptyl with X, the cyclohexyl is other than a trisubstituted cyclohexyl bearing $CH_3$, i-Pr and $(CH_2)_2CO_2CH_3$ groups or $CH_3$, i-Pr and $(CH_2)_3NH_2$, or a salt or ester thereof.

DETAILED DESCRIPTION OF THE INVENTION

Figure 1:
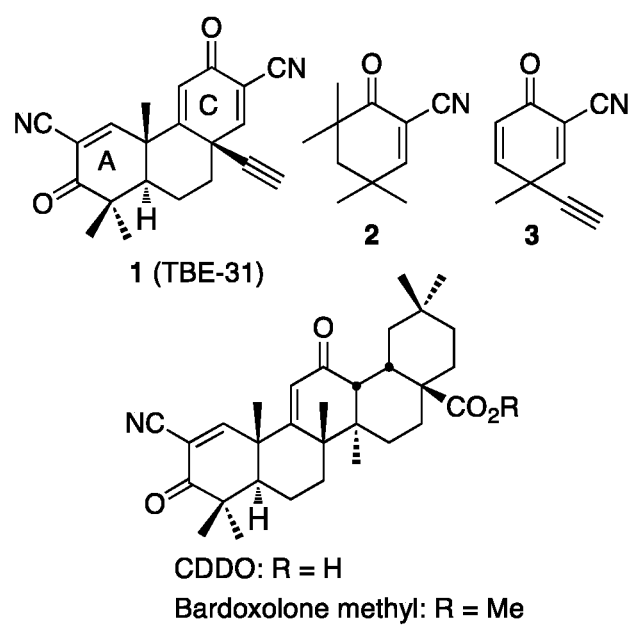
FIG. 1: Structures of 1 (TBE-31), monocyclic cyanoenones 2 and 3, CDDO and bardoxolone methyl.

The present invention provides a compound having the structure:

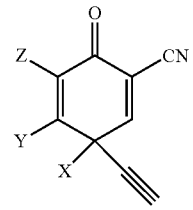

wherein
X is $C_1$-$C_{12}$ alkyl, $C_2$-$C_{12}$ alkenyl, $C_2$-$C_{12}$ alkynyl, cyano, aryl, heteroaryl, alkylaryl, alkylheteroaryl, alkenylaryl, alkenylheteroaryl, alkynylaryl, alkynylheteroaryl, alkoxy, alkenyloxy, alkynyloxy, aryloxy, heteroaryloxy, acyl, alkylhydroxy, alkylamino, alkenylamino, alkynylamino, amido, carboxyl, or carboxyl ester, or forms an unsubstituted or substituted cyclobutyl, cyclopentyl, cyclohexyl, cycloheptyl, indane or tetralin with Y, Y is H or forms an unsubstituted or substituted cyclobutyl, cyclopentyl, cyclohexyl, cycloheptyl, indane or tetralin with X, or forms an unsubstituted or substituted monocycle with Z; and Z is H or forms an unsubstituted or substituted monocycle with Y;
  wherein when X and Y are both H, then X is $C_2$ alkenyl or $C_2$ alkynyl, and when Y is H forms a substituted cyclohexyl, cycloheptyl with X, the cyclohexyl is other than a trisubstituted
  cyclohexyl bearing $CH_3$, i-Pr and $(CH_2)_2CO_2CH_3$ groups or $CH_3$, i-Pr and $(CH_2)_3NH_2$,
  or a salt or ester thereof.

In one embodiment, the compound wherein
X is $C_1$-$C_{12}$ alkyl, $C_2$-$C_{12}$ alkenyl, $C_2$-$C_{12}$ alkynyl, cyano, aryl, heteroaryl, alkylaryl, alkylheteroaryl, alkenylaryl, alkenylheteroaryl, alkynylaryl, alkynylheteroaryl, alkoxy, alkenyloxy, alkynyloxy, aryloxy, heteroaryloxy, acyl, alkylhydroxy, alkylamino, alkenylamino, alkynylamino, amido, carboxyl, or carboxyl ester, or forms an unsubstituted or substituted indane or tetralin with Y, Y is H or forms an unsubstituted or substituted indane or tetralin with X, or forms an unsubstituted or substituted monocycle with Z; and nm Z is H or forms an unsubstituted or substituted monocycle with Y,
  wherein when X and Y are both H, then X is $C_2$ alkenyl or $C_2$ alkynyl,
  or a salt or ester thereof.

In one embodiment, the compound wherein

X is $C_1$-$C_{12}$ alkyl, $C_2$-$C_{12}$ alkenyl, $C_2$-$C_{12}$ alkynyl, cyano, aryl, heteroaryl, alkylaryl, alkylheteroaryl, alkenylaryl, alkenylheteroaryl, alkynylaryl, alkynylheteroaryl, alkoxy, alkenyloxy, alkynyloxy, aryloxy, heteroaryloxy, acyl, alkylhydroxy, alkylamino, alkenylamino, alkynylamino, amido, carboxyl, or carboxyl ester, or forms an unsubstituted or substituted cyclobutyl, cyclopentyl, cyclohexyl or cycloheptyl with Y, Y is H or forms an unsubstituted or substituted cyclobutyl, cyclopentyl, cyclohexyl or cycloheptyl with X, or forms an unsubstituted or substituted monocycle with Z; and nm Z is H or forms an unsubstituted or substituted monocycle with Y, wherein when X and Y are both H, then X is $C_2$ alkenyl or $C_2$ alkynyl, and when Y is H forms a substituted cyclohexyl, cycloheptyl with X, the cyclohexyl is other than a trisubstituted cyclohexyl bearing $CH_3$, i-Pr and $(CH_2)_2CO_2CH_3$ groups or $CH_3$, i-Pr and $(CH_2)_3NH_2$, or a salt or ester thereof.

In one embodiment, the compound wherein

X is $C_1$-$C_{12}$ alkyl, $C_2$-$C_{12}$ alkenyl, $C_2$-$C_{12}$ alkynyl, cyano, aryl, heteroaryl, alkylaryl, alkylheteroaryl, alkenylaryl, alkenylheteroaryl, alkynylaryl, alkynylheteroaryl, alkoxy, alkenyloxy, alkynyloxy, aryloxy, heteroaryloxy, acyl, alkylhydroxy, alkylamino, alkenylamino, alkynylamino, amido, carboxyl, or carboxyl ester, or forms an unsubstituted or substituted cyclobutyl, cyclopentyl or cycloheptyl with Y, Y is H or forms an unsubstituted or substituted cyclobutyl, cyclopentyl or cycloheptyl with X, or forms an unsubstituted or substituted monocycle with Z; and nm Z is H or forms an unsubstituted or substituted monocycle with Y, wherein when X and Y are both H, then X is $C_2$ alkenyl or $C_2$ alkynyl, or a salt or ester thereof.

In one embodiment, when X and Y form a substituted cyclobutyl, cyclopentyl, cyclohexyl or cycloheptyl, the substituents do not form a fused bicyclic ring with the cyclobutyl, cyclopentyl, cyclohexyl or cycloheptyl.

In one embodiment, when X and Y form a substituted cyclobutyl, cyclopentyl, cyclohexyl or cycloheptyl, the substituents are other than a fused bicyclic ring with the cyclobutyl, cyclopentyl, cyclohexyl or cycloheptyl.

In one embodiment, when X and Y form a substituted cyclobutyl, cyclopentyl, cyclohexyl or cycloheptyl, the substituents do not form a fused polycyclic ring with the cyclobutyl, cyclopentyl, cyclohexyl or cycloheptyl.

In one embodiment, when X and Y form a substituted cyclobutyl, cyclopentyl, cyclohexyl or cycloheptyl, the substituents are other than a fused polycyclic ring with the cyclobutyl, cyclopentyl, cyclohexyl or cycloheptyl.

In one embodiment, the compound having the structure:

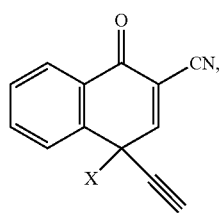

wherein X is $C_1$-$C_{12}$ alkyl, $C_2$-$C_{12}$ alkenyl, $C_2$-$C_{12}$ alkynyl, cyano, aryl, heteroaryl, alkylaryl, alkylheteroaryl, alkenylaryl, alkenylheteroaryl, alkynylaryl, alkynyiheteroaryl, alkoxy, alkenyloxy, alkenyloxy, aryloxy, heteroaryloxy, acyl, alkylhydroxy, alkylamino, alkenylamino, alkynylamino, amido, carboxyl, or carboxyl ester.

In one embodiment, the compound wherein X is $C_1$-$C_{12}$ alkyl, $C_2$-$C_{12}$ alkenyl, $C_2$-$C_{12}$ alkynyl.

In one embodiment, the compound wherein X is $C_1$-$C_{12}$ alkyl.

In one embodiment, the compound having the structure:

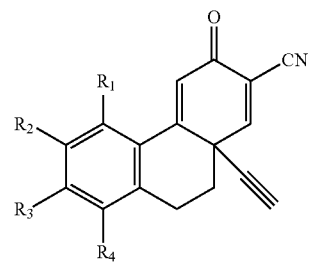

wherein $R_1$, $R_2$, $R_3$ and $R_4$ are each independently, —H, halogen, —CN, —$CF_3$, —$OCF_3$, —($C_1$-$C_{12}$ alkyl), —($C_2$-$C_{12}$ alkenyl), —($C_2$-$C_{12}$ alkynyl), -(aryl), -(heteroaryl), —($C_1$-$C_{12}$ alkyl)-(aryl), —($C_2$-$C_{12}$ alkenyl)-(aryl), —($C_2$-$C_{12}$ alkynyl)-(aryl), —($C_1$-$C_{12}$ alkyl)-(heteroaryl), —($C_2$-$C_{12}$ alkenyl)-(heteroaryl), —($C_2$-$C_{12}$ alkynyl)-(heteroaryl), -(heteroalkyl), -(hydroxyalkyl), -(alkyl)-$NH_2$, —NH-(alkyl), —NH-(alkenyl), —NH-(alkynyl) —NH-(aryl), —NH-(heteroaryl), —OH, —OAc, —$CO_2H$, —$CO_2$-(alkyl), —O—C(O)(alkyl), —O-(alkyl), —O-(alkenyl), —O-(alkynyl), —O-(aryl), —O-(heteroaryl), C(O)—$NH_2$, C(O)—NH-(alkyl), C(O)—NH-(aryl) or C(O)—NH-(heteroaryl).

In one embodiment, the compound wherein $R_1$, $R_2$, $R_3$ and $R_4$ are each independently, —H, halogen or —($C_1$-$C_{12}$ alkyl).

In one embodiment, the compound wherein $R_1$, $R_2$, $R_3$ and $R_4$ are each independently, —H, —F, —Cl, —Br, I, or —$CH_3$.

In one embodiment, the compound wherein $R_1$ is —H, halogen or —($C_1$-$C_{12}$ alkyl); and $R_2$, $R_3$ and $R_4$ are each —H.

In one embodiment, the compound wherein $R_1$ is H, —F, —Cl, —Br, I, or —$CH_3$; and $R_2$, $R_3$ and $R_4$ are each —H.

In one embodiment, the compound having the structure:

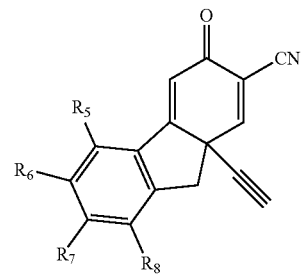

wherein $R_5$, $R_6$, $R_7$ and $R_8$ are each independently, —H, halogen, —CN, —$CF_3$, —$OCF_3$, —($C_1$-$C_{12}$ alkyl), —($C_2$-$C_{12}$ alkenyl), —($C_2$-$C_{12}$ alkynyl), -(aryl), -(heteroaryl), —($C_1$-$C_{12}$ alkyl)-(aryl), —($C_2$-$C_{12}$ alkenyl)-(aryl), —($C_2$-$C_{12}$ alkynyl)-(aryl), —($C_1$-$C_{12}$ alkyl)-(heteroaryl), —($C_2$-$C_{12}$ alkenyl)-(heteroaryl), —($C_2$-$C_{12}$ alkynyl)-(heteroaryl), -(heteroalkyl), -(hydroxyalkyl), -(alkyl)-NH$_2$, —NH-(alkyl), —NH-(alkenyl), —NH-(alkynyl) —NH-(aryl), —NH-(heteroaryl), —OH, —OAc, —CO$_2$H, —CO$_2$-(alkyl), —O—C(O)(alkyl), —O-(alkyl), —O-(alkenyl), —O-(alkynyl), —O-(aryl), —O-(heteroaryl), C(O)—NH$_2$, C(O)—NH-(alkyl), C(O)—NH-(aryl) or C(O)—NH-(heteroaryl).

In one embodiment, the compound wherein R$_5$, R$_6$, R$_7$ and R$_8$ are each independently, —H, halogen or —(C$_1$-C$_{12}$ alkyl).

In one embodiment, the compound wherein R$_5$, R$_6$, R$_7$ and R$_8$ are each independently, —H, —F, —Cl, —Br, I, or —CH$_3$.

In one embodiment, the compound wherein R$_5$ is —H, halogen or —(C$_1$-C$_{12}$ alkyl); and R$_6$, R$_7$ and R$_8$ are each —H.

In one embodiment, the compound wherein R$_5$ is H, —F, —Cl, —Br, I, or —CH$_3$; and R$_6$, R$_7$ and R$_8$ are each —H.

In one embodiment, the compound having the structure:

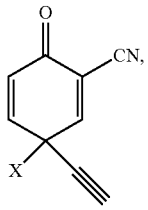

wherein X is C$_2$ alkenyl or C$_2$ alkynyl.

In one embodiment, the compound having the structure:

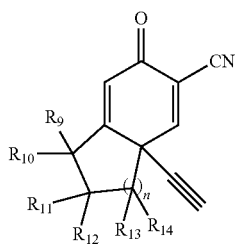

n=0-3;

R$_9$, R$_{10}$, R$_{11}$ and R$_{12}$ are each independently, —H, halogen, —CN, —CF$_3$, —OCF$_3$, —(C$_1$-C$_{12}$ alkyl), —(C$_2$-C$_{12}$ alkenyl), —(C$_2$-C$_{12}$ alkynyl), -(aryl), -(heteroaryl), —(C$_1$-C$_{12}$ alkyl)-(aryl), —(C$_2$-C$_{12}$ alkenyl)-(aryl), —(C$_2$-C$_{12}$ alkynyl)-(aryl), —(C$_1$-C$_{12}$ alkyl)-(heteroaryl), —(C$_2$-C$_{12}$ alkenyl)-(heteroaryl), —(C$_2$-C$_{12}$ alkynyl)-(heteroaryl), -(heteroalkyl), -(hydroxyalkyl), -(alkyl)-NH$_2$, —NH-(alkyl), —NH-(alkenyl), —NH-(alkynyl) —NH-(aryl), —NH-(heteroaryl), —OH, —OAc, —CO$_2$H, —CO$_2$-(alkyl), —O—C(O)(alkyl), —O-(alkyl), —O-(alkenyl), —O-(alkynyl), —O-(aryl), —O-(heteroaryl), C(O)—NH$_2$, C(O)—NH-(alkyl), C(O)—NH-(aryl) or C(O)—NH-(heteroaryl); and each occurrence of R$_{13}$ and R$_{14}$ is each independently, —H, halogen, —CN, —CF$_3$, —OCF$_3$, —(C$_1$-C$_{12}$ alkyl), —(C$_2$-C$_{12}$ alkenyl), —(C$_2$-C$_{12}$ alkynyl), -(aryl), -(heteroaryl), —(C$_1$-C$_{12}$ alkyl)-(aryl), —(C$_2$-C$_{12}$ alkenyl)-(aryl), —(C$_2$-C$_{12}$ alkynyl)-(aryl), —(C$_1$-C$_{12}$ alkyl)-(heteroaryl), —(C$_2$-C$_{12}$ alkenyl)-(heteroaryl), —(C$_2$-C$_{12}$ alkynyl)-(heteroaryl), -(heteroalkyl), -(hydroxyalkyl), -(alkyl)-NH$_2$, —NH-(alkyl), —NH-(alkenyl), —NH-(alkynyl) —NH-(aryl), —NH-(heteroaryl), —OH, —OAc, —CO$_2$H, —CO$_2$-(alkyl), —O—C(O)(alkyl), —O-(alkyl), —O-(alkenyl), —O-(alkynyl), —O-(aryl), —O-(heteroaryl), C(O)—NH$_2$, C(O)—NH-(alkyl), C(O)—NH-(aryl) or C(O)—NH-(heteroaryl).

In one embodiment, the compound wherein n=0.

In one embodiment, the compound wherein n=1 and R$_{13}$ and R$_{14}$ are each —H.

In one embodiment, the compound wherein n=2 and each occurrence of R$_{13}$ and R$_{14}$ is —H; or wherein n=3 and each occurrence of R$_{13}$ and R$_{14}$ is —H.

In one embodiment, the compound having the structure:

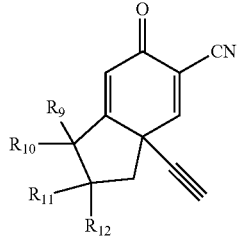

wherein R$_9$, R$_{10}$, R$_{11}$ and R$_{12}$ are each independently, —H, halogen, —CN, —CF$_3$, —OCF$_3$, —(C$_1$-C$_{12}$ alkyl), —(C$_2$-C$_{12}$ alkenyl), —(C$_2$-C$_{12}$ alkynyl), -(aryl), -(heteroaryl), —(C$_1$-C$_{12}$ alkyl)-(aryl), —(C$_2$-C$_{12}$ alkenyl)-(aryl), —(C$_2$-C$_{12}$ alkynyl)-(aryl), —(C$_1$-C$_{12}$ alkyl)-(heteroaryl), —(C$_2$-C$_{12}$ alkenyl)-(heteroaryl), —(C$_2$-C$_{12}$ alkynyl)-(heteroaryl), -(heteroalkyl), -(hydroxyalkyl), -(alkyl)-NH$_2$, —NH-(alkyl), —NH-(alkenyl), —NH-(alkynyl) —NH-(aryl), —NH-(heteroaryl), —OH, —OAc, —CO$_2$H, —CO$_2$-(alkyl), —O—C(O)(alkyl), —O-(alkyl), —O-(alkenyl), —O-(alkynyl), —O-(aryl), —O-(heteroaryl), C(O)—NH$_2$, C(O)—NH-(alkyl), C(O)—NH-(aryl) or C(O)—NH-(heteroaryl).

In one embodiment, the compound wherein R$_9$, R$_{10}$, R$_{11}$ and R$_{12}$ are each independently, —H or —(C$_1$-C$_{12}$ alkyl).

In one embodiment, the compound wherein R$_9$, R$_{10}$, R$_{11}$ and R$_{12}$ are each independently, —H or —CH$_3$.

In one embodiment, the compound wherein R$_9$, R$_{10}$, R$_{11}$ and R$_{12}$ are each —H.

In one embodiment, the compound wherein R$_9$ and R$_{10}$ are each —CH$_3$; and R$_{11}$ and R$_{12}$ are each —H.

In one embodiment, the compound having the structure:

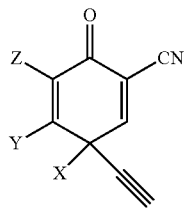

wherein

X is C$_1$-C$_{12}$ alkyl, C$_2$-C$_{12}$ alkenyl or C$_2$-C$_{12}$ alkynyl, or forms an unsubstituted or substituted cyclopentyl, indane or tetralin with Y, Y is H or forms an unsubstituted or substituted cyclopentyl, indane or tetralin with X, or forms an unsubstituted or substituted phenyl with Z; and Z is H or forms an unsubstituted or substituted phenyl with Y;

wherein when X and Y are both H, then X is C$_2$ alkenyl or C$_2$ alkynyl, or a salt or ester thereof.

In one embodiment, the compound having the structure:

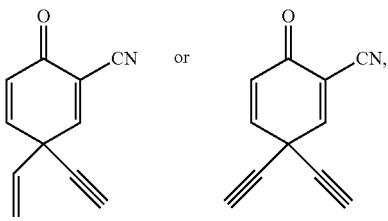

or a salt thereof.

In one embodiment, the compound having the structure:

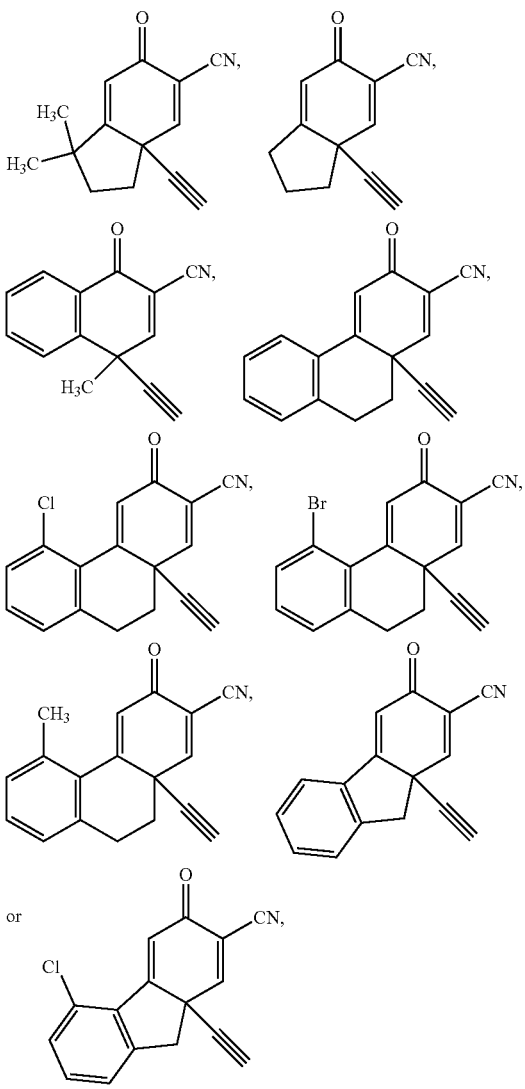

or a salt thereof.

The present invention also provides a pharmaceutical composition comprising any of the compounds of the present invention and a pharmaceutically acceptable carrier.

The present invention also provides a method of treating a subject afflicted with cancer comprising administering an effective amount of any of the compounds of the present invention to the subject so as to thereby treat the subject afflicted with cancer.

The present invention also provides a method of treating a subject afflicted with an inflammatory disease comprising administering an effective amount of the compound of any of the compounds of the present invention to the subject so as to thereby treat the subject afflicted with inflammatory disease.

The present invention also provides a method of treating a subject afflicted with a cardiovascular disease comprising administering an effective amount of the compound of any of the compounds of the present invention to the subject so as to thereby treat the subject afflicted with the cardiovascular disease.

The present invention also provides a method of treating a subject afflicted with a neurodegenerative disease comprising administering an effective amount of the compound of any of the compounds of the present invention to the subject so as to thereby treat the subject afflicted with the neurodegenerative disease.

The present invention also provides a method of treating a subject afflicted with a disease characterized by overexpression of COX-2 genes comprising administering an effective amount of the compound any of the compounds of the present invention to the subject so as to thereby treat the subject afflicted with the disease characterized by overexpression of COX-2 genes.

The present invention also provides a method of treating a subject afflicted with a disease characterized by overexpression of iNOS genes comprising administering an effective amount of the compound any of the compounds of the present invention to the subject so as to thereby treat the subject afflicted with the disease characterized by overexpression of iNOS genes.

The present invention also provides a method of treating a subject afflicted with renal or kidney disease comprising administering an effective amount of the compound of any of the compounds of the present invention to the subject so as to thereby treat the subject afflicted with the renal or kidney disease.

In one embodiment, the method further comprising the administration of an anti-cancer agent to subject.

In one embodiment, the anti-cancer agent is 5-azacitidine, 5-fluorouracil, 9-cis-retinoic acid, actinomycin D, alitretinoin, all-trans-retinoic acid, annamycin, axitinib, belinostat, bevacizumab, bexarotene, bosutinib, busulfan, capecitabine, carboplatin, carmustine, CD437, cediranib, cetuximab, chlorambucil, cisplatin, cyclophosphamide, cytarabine, dacarbazine, dasatinib, daunorubicin, decitabine, docetaxel, dolastatin-10, doxifluridine, doxorubicin, doxorubicin, epirubicin, erlotinib, etoposide, etoposide, gefitinib, gemcitabine, gemtuzumab ozogamicin, hexamethylmelamine, idarubicin, ifosfamide, imatinib, irinotecan, isotretinoin, ixabepilone, lapatinib, LBH589, lomustine, mechlorethamine, melphalan, mercaptopurine, methotrexate, mitomycin, mitoxantrone, MS-275, neratinib, nilotinib, nitrosourea, oxaliplatin, paclitaxel, plicamycin, procarbazine, semaxanib, semustine, sodium butyrate, sodium phenylacetate, streptozotocin, suberoylanilide hydroxamic acid, sunitinib, tamoxifen, teniposide, thiopeta, tioguanine, topotecan, TRAIL, trastuzumab, tretinoin, trichostatin A, valproic acid, valrubicin, vandetanib, vinblastine, vincristine, vindesine, or vinorelbine.

In one embodiment, the amount of the compound and the amount of the anti-cancer agent are administered simultaneously, separately or sequentially.

In one embodiment, the amount of the compound and the amount of the chemotherapeutic agent when taken together is more effective to treat the subject than when the anti-cancer agent is administered alone.

In one embodiment, the amount of the compound and the amount of the anti-cancer agent when taken together is effective to reduce a clinical symptom of the cancer in the subject.

In one embodiment, the treating comprises inhibiting proliferation of or inducing apoptosis of cancer cells in the subject.

In one embodiment, the compound enhances the anti-cancer effect of the anti-cancer agent.

The present invention provides a pharmaceutical composition comprising the compound of the present invention and at least one pharmaceutically acceptable carrier for use in treating cancer, an inflammatory disease, a cardiovascular disease, a neurodegenerative disease, a disease characterized by over-expression of COX-2, a disease characterized by over-expression of iNOS genes, renal disease or kidney disease.

The present invention also provides a package comprising:

1) a first pharmaceutical composition comprising an amount of an anti-cancer agent and a pharmaceutically acceptable carrier;

2) a second pharmaceutical composition comprising an amount of the compound of the present invention and a pharmaceutically acceptable carrier; and 3) instructions for use of the first and second pharmaceutical compositions together to treat cancer.

The present invention provides a pharmaceutical composition comprising the compound of the present invention and an anti-cancer agent, and at least one pharmaceutically acceptable carrier for use in treating cancer.

In some embodiments, the compound of the present invention for use as an add-on therapy or in combination with an anti-cancer agent for use in treating a subject afflicted with cancer.

In some embodiments, the compound of the present invention in combination with an anti-cancer agent for use in treating cancer.

In some embodiments, a product containing an amount of the compound of the present invention and an amount of an anti-cancer agent for simultaneous, separate or sequential use in treating a subject afflicted with cancer.

In some embodiments, the compound of the present invention for use in treating an inflammatory disease, a neurodegenerative disease, renal disease, kidney disease, a disease characterized by overexpression of COX-2 genes or a disease characterized by overexpression of iNOS genes.

Use of the compound of the present invention for treating an inflammatory disease, a neurodegenerative disease, renal disease, kidney disease, a disease characterized by overexpression of COX-2 genes or a disease characterized by overexpression of iNOS genes.

The compounds disclosed herein inhibit the production of nitric oxide in macrophage-derived RAW 264.7 cells induced by exposure to γ-interferon. They also induce the expression of antioxidant proteins such as NQO1 and reduce the expression of pro-inflammatory proteins such as COX-2 and inducible nitric oxide synthase (iNOS). These properties are relevant to the treatment of a wide array of diseases involving oxidative stress and dysregulation of inflammatory processes including cancer, mucositis resulting from radiation therapy or chemotherapy, autoimmune diseases, cardiovascular diseases including atherosclerosis, ischemia-reperfusion injury, acute and chronic organ failure including renal failure and heart failure, respiratory diseases, diabetes and complications of diabetes, severe allergies, transplant rejection, graft-versus-host disease, neurodegenerative diseases, diseases of the eye and retina, acute and chronic pain, degenerative bone diseases including osteoarthritis and osteoporosis, inflammatory bowel diseases, dermatitis and other skin diseases, sepsis, burns, seizure disorders, and neuropsychiatric disorders. Without being bound by theory, the activation of the antioxidant/anti-inflammatory Keap1/Nrf2/ARE pathway is believed to be implicated in both the anti-inflammatory and anti-carcinogenic properties of the compounds disclosed herein. For a discussion on diseases associated with the Keap1/Nrf2/ARE pathway, expression of NQO1, expression of COX-2 and/or expression of iNOS, see, for example, WO 2010/001782, published Jan. 28, 2010, which is incorporated by reference herein in its entirety.

In some embodiments, a method of treating cancer in a subject comprising administering to the subject an effective amount of a compound of the present invention. The cancer may be, but is not limited to, such as a carcinoma, sarcoma, lymphoma, leukemia, melanoma, mesothelioma, multiple myeloma, or seminoma. Other types of cancers include cancer of the bladder, blood, bone, brain, breast, central nervous system, colon, endometrium, esophagus, genitourinary tract, head, larynx, liver, lung, neck, ovary, pancreas, prostate, spleen, small intestine, large intestine, stomach, or testicle.

In some embodiments, the method may further comprise an effective amount of a second agent. In some embodiments, the method wherein the amount of the compound and the second agent are administered simultaneously, separately or sequentially.

The second agent may, in some embodiments, be an antibiotic, anti-inflammatory, anti-neoplastic, anti-proliferative, anti-viral, immunomodulatory, or immunosuppressive. The second agent may be an alkylating agent, androgen receptor modulator, cytoskeletal disruptor, estrogen receptor modulator, histone-deacetylase inhibitor, HMG-CoA reductase inhibitor, prenyl-protein transferase inhibitor, retinoid receptor modulator, topoisomerase inhibitor, or tyrosine kinase inhibitor.

In some embodiments the scond agent is an anti-cancer agent selected form 5-azacitidine, 5-fluorouracil, 9-cis-retinoic acid, actinomycin D, alitretinoin, all-trans-retinoic acid, annamycin, axitinib, belinostat, bevacizumab, bexarotene, bosutinib, busulfan, capecitabine, carboplatin, carmustine, CD437, cediranib, cetuximab, chlorambucil, cisplatin, cyclophosphamide, cytarabine, dacarbazine, dasatinib, daunorubicin, decitabine, docetaxel, dolastatin-10, doxifluridine, doxorubicin, doxorubicin, epirubicin, erlotinib, etoposide, etoposide, gefitinib, gemcitabine, gemtuzumab ozogamicin, hexamethylmelamine, idarubicin, ifosfamide, imatinib, irinotecan, isotretinoin, ixabepilone, lapatinib, LBH589, lomustine, mechlorethamine, melphalan, mercaptopurine, methotrexate, mitomycin, mitoxantrone, MS-275, neratinib, nilotinib, nitrosourea, oxaliplatin, paclitaxel, plicamycin, procarbazine, semaxanib, semustine, sodium butyrate, sodium phenylacetate, streptozotocin, suberoylanilide hydroxamic acid, sunitinib, tamoxifen, teniposide, thiopeta, tioguanine, topotecan, TRAIL, trastuzumab, tretinoin, trichostatin A, valproic acid, valrubicin, vandetanib, vinblastine, vincristine, vindesine, or vinorelbine.

In some embodiments, a method of treating inflammatory disease in a subject comprising administering to the subject an effective amount of a compound of the present invention.

The disease may be, for example, lupus or rheumatoid arthritis. The disease may be an inflammatory bowel disease, such as Crohn's disease or ulcerative colitis. The disease with an inflammatory component may be a cardiovascular disease. The disease with an inflammatory component may be diabetes, such as type 1 or type 2 diabetes. Compounds of the present invnetion may also be used to treat complications associated with diabetes. Such complications are well-known in the art and include, for example, obesity, hypertension, atherosclerosis, coronary heart disease, stroke, peripheral vascular disease, hypertension, nephropathy, neuropathy, myonecrosis, retinopathy and metabolic syndrome (syndrome X). The inflammatory disease may be a skin disease, such as psoriasis, acne, or atopic dermatitis. Administration of a compound of the present disclosure in treatment methods of such skin diseases may be, for example, topical or oral.

The inflammatory disease may be metabolic syndrome (syndrome X). A patient having this syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670, incorporated herein by reference. Patients with metabolic syndrome, whether or not they have or develop overt diabetes mellitus, have an increased risk of developing the macrovascular and microvascular complications that are listed above that occur with type 2 diabetes, such as atherosclerosis and coronary heart disease.

Another general method of the present disclosure entails a method of treating or preventing a cardiovascular disease in a subject, comprising administering to the subject a pharmaceutically effective amount of a compound of the present disclosure.

In some embodiments, a method of treating cardiovascular disease in a subject comprising administering to the subject an effective amount of a compound of the present invention. The cardiovascular disease may be, for example, atherosclerosis, cardiomyopathy, congenital heart disease, congestive heart failure, myocarditis, rheumatic heart disease, valve disease, coronary artery disease, endocarditis, or myocardial infarction. Combination therapy is also contemplated for such methods. For example, such methods may further comprise administering a pharmaceutically effective amount of a second drug. The second drug may be, for example, a cholesterol lowering drug, an anti-hyperlipidemic, a calcium channel blocker, an anti-hypertensive, or an HMG-CoA reductase inhibitor. Non-limiting examples of second drugs include amlodipine, aspirin, ezetimibe, felodipine, lacidipine, lercanidipine, nicardipine, nifedipine, nimodipine, nisoldipine or nitrendipine. Other non-limiting examples of second drugs include atenolol, bucindolol, carvedilol, clonidine, doxazosin, indoramin, labetalol, methyldopa, metoprolol, nadolol, oxprenolol, phenoxybenzamine, phentolamine, pindolol, prazosin, propranolol, terazosin, timolol or tolazoline. The second drug may be, for example, a statin, such as atorvastatin, cerivastatin, fluvastatin, lovastatin, mevastatin, pitavastatin, pravastatin, rosuvastatin or simvastatin.

In some embodiments, a method of treating neurodegenerative disease in a subject comprising administering to the subject an effective amount of a compound of the present invention. The neurodegenerative disease may be, for example, be selected from the group consisting of Parkinson's disease, Alzheimer's disease, multiple sclerosis (MS), Huntington's disease and amyotrophic lateral sclerosis. In particular embodiments, the neurodegenerative disease is Alzheimer's disease. In particular embodiments, the neurodegenerative disease is MS, such as primary progressive, relapsing-remitting secondary progressive or progressive relapsing MS.

In some embodiments, a method of treating a disorder characterized by overexpression of iNOS genes in a subject comprising administering to the subject an effective amount of a compound of the present invention.

In some embodiments, a method of inhibiting IFN-γ-induced nitric oxide production in cells of a subject comprising administering to said subject an effective amount of a compound of the present invention.

In some embodiments, a method of treating a disorder characterized by overexpression of COX-2 genes in a subject, comprising administering to the subject a pharmaceutically effective amount of compound of the present disclosure.

In some embodiments, a method of treating renal/kidney disease (RKD) in a subject comprising administering to the subject an effective amount of a compound of the present invention. See, for example, U.S. patent application Ser. No. 12/352,473, which is incorporated by reference herein in its entirety. The RKD may result from, for example, a toxic insult. The toxic insult may result from, for example, an imaging agent or a drug. The drug may be a chemotherapeutic, for example. The RKD may result from ischemia/reperfusion injury, in certain embodiments. In certain embodiments, the RKD results from diabetes or hypertension. The RKD may result from an autoimmune disease. The RKD may be further defined as chronic RKD, or acute RKD. In certain methods of treating renal/kidney disease (RKD) in a subject, comprising administering to the subject an effective amount of a compound of the present invention, the subject has undergone or is undergoing dialysis. In certain embodiments, the subject has undergone or is a candidate to undergo kidney transplant. The subject may be a primate. The primate may be a human. The subject in this or any other method may be, for example, a cow, horse, dog, cat, pig, mouse, rat or guinea pig.

In some embodiments, compounds disclosed herein may be used in treating diseases and disorders characterized by overexpression of inducible nitric oxide synthase (iNOS), inducible cyclooxygenase (COX-2), or both, in affected tissues; high levels of production of reactive oxygen species (ROS) or reactive nitrogen species (RNS) such as superoxide, hydrogen peroxide, nitric oxide or peroxynitrite; or excessive production of inflammatory cytokines or other inflammation-related proteins such as TNEa, IL-6, IL-1, IL-8, ICAM-1, VCAM-1, and VEGF. Such diseases or disorders may, in some embodiments, involve undesirable proliferation of certain cells, as in the case of cancer (e.g., solid tumors, leukemias, myelomas, lymphomas, and other cancers), fibrosis associated with organ failure, or excessive scarring. Other such disorders include (but are not limited to) autoimmune diseases such as lupus, rheumatoid arthritis, juvenile-onset diabetes, multiple sclerosis, psoriasis, and Crohn's disease; cardiovascular diseases such as atherosclerosis, heart failure, myocardial infarction, acute coronary syndrome, restenosis following vascular surgery, hypertension, and vasculitis; neurodegenerative or neuromuscular diseases such as Alzheimer's disease, Parkinson's disease, Huntington's disease, ALS, and muscular dystrophy; neurological disorders such as epilepsy and dystonia; neuropsychiatric conditions such as major depression, bipolar disorder, post-traumatic stress disorder, schizophrenia, anorexia nervosa, ADHD, and autism-spectrum disorders; retinal diseases such as macular degeneration, diabetic retinopathy, glaucoma, and retinitis; chronic and acute pain syndromes, including inflammatory and neuropathic pain; hearing loss and tinnitus; diabetes and complications of diabetes, including metabolic syndrome, diabetic nephropathy, diabetic neuropathy, and diabetic ulcers; respiratory diseases such as asthma, chronic obstructive pulmonary disease, acute respiratory distress syndrome, and cystic fibrosis; inflammatory bowel diseases; osteoporosis, osteoarthritis, and other degenerative conditions of bone and cartilage; acute or chronic organ failure, including renal failure, liver failure (including cirrhosis and hepatitis), and pancreatitis; ischemia-reperfusion injury associated with thrombotic or hemorrhagic stroke, subarachnoid hemorrhage, cerebral vasospasm, myocardial infarction, shock, or trauma; complications of organ or tissue transplantation including acute or chronic transplant failure or rejection and graft-versus-host disease; skin diseases including atopic dermatitis and acne; sepsis and septic shock; excessive inflammation associated with infection, including respiratory inflammation associated with influenza and upper respiratory infections; mucositis associated with cancer therapy, including radiation therapy or chemotherapy; and severe burns.

As used herein, a "symptom" associated with a disease or disorder includes any clinical or laboratory manifestation associated with the disease or disorder and is not limited to what the subject can feel or observe.

As used herein, "treating", e.g. of a cancer, encompasses inducing prevention, inhibition, regression, or stasis of the disease or a symptom or condition associated with the infection.

The compounds of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention.

The compounds of the subject invention may have spontaneous tautomeric forms. In cases wherein compounds may exist in tautomeric forms, such as keto-enol tautomers, each tautomeric form is contemplated as being included within this invention whether existing in equilibrium or predominantly in one form.

In the compound structures depicted herein, hydrogen atoms are not shown for carbon atoms having less than four bonds to non-hydrogen atoms. However, it is understood that enough hydrogen atoms exist on said carbon atoms to satisfy the octet rule.

This invention also provides isotopic variants of the compounds disclosed herein, including wherein the isotopic atom is $^2H$ and/or wherein the isotopic atom $^{13}C$. Accordingly, in the compounds provided herein hydrogen can be enriched in the deuterium isotope. It is to be understood that the invention encompasses all such isotopic forms.

It is understood that the structures described in the embodiments of the methods hereinabove can be the same as the structures of the compounds described hereinabove.

It is understood that where a numerical range is recited herein, the present invention contemplates each integer between, and including, the upper and lower limits, unless otherwise stated.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration.

It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano, carbamoyl and aminocarbonyl and aminothiocarbonyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2, . . . , n−1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on, or any length therein. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2, . . . , n−1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl, $C_3$-$C_{12}$ alkenyl, $C_4$-$C_{12}$ alkenyl and so on or any length therein.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n−1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl, $C_3$-$C_{12}$ alkynyl, $C_4$-$C_{12}$ alkynyl and so on or any length therein.

"Alkylene", "alkenylene" and "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "heteroalkyl" includes both branched and straight-chain saturated aliphatic hydrocarbon groups having the specified number of carbon atoms and at least 1 heteroatom within the chain or branch.

As used herein, "heterocycle" or "heterocyclyl" as used herein is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

As herein, "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to atoms with each ring being independently unsubstituted or substituted. Examples of such non-aromatic bicycle elements include but are not limited to: decahydronaphthalene. Examples of such aromatic bicycle elements include but are not limited to: naphthalene.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

As used herein, the term "polycyclic" refers to unsaturated or partially unsaturated multiple fused ring structures, which may be unsubstituted or substituted.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, triazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The alkyl, alkenyl, alkynyl, aryl, heteroaryl and heterocyclyl substituents may be substituted or unsubstituted, unless specifically defined otherwise. In the compounds of the present invention, alkyl, alkenyl, alkynyl, aryl, heterocyclyl and heteroaryl groups can be further substituted by replacing one or more hydrogen atoms with alternative non-hydrogen groups. These include, but are not limited to, halo, hydroxy, mercapto, amino, carboxy, cyano and carbamoyl.

As used herein, the term "halogen" refers to F, Cl, Br, and I.

The terms "substitution", "substituted" and "substituent" refer to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or pluraly. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5th Edition (1996), March's Advanced Organic Chemistry: Reactions, Mechanisms, and Structure, Michael B. Smith, Jerry March, (Wiley-Interscience) 5th Edition (2007), and references therein, which are incorporated by reference herein. However, these may not be the only means by which to synthesize or obtain the desired compounds.

Another aspect of the invention comprises a compound used in the method of the present invention as a pharmaceutical composition.

In some embodiments, a pharmaceutical composition comprising the compound of the present invention and a pharmaceutically acceptable carrier.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, 30th edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", $J.$ $Pharm.$ $Sci.$ 66:1-19).

The compounds of the present invention may also form salts with basic amino acids such a lysine, arginine, etc. and with basic sugars such as N-methylglucamine, 2-amino-2-deoxyglucose, etc. and any other physiologically non-toxic basic substance.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier as are slow-release vehicles.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antitumor agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or topically onto a site of disease or lesion, all using dosage forms well known to those of ordinary skill in the pharmaceutical arts.

The compounds used in the method of the present invention can be administered in admixture with suitable pharmaceutical diluents, extenders, excipients, or in carriers such as the novel programmable sustained-release multi-compartmental nanospheres (collectively referred to herein as a pharmaceutically acceptable carrier) suitably selected with respect to the intended form of administration and as consistent with conventional pharmaceutical practices. The unit will be in a form suitable for oral, nasal, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used.

The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamellar vesicles, and multilamellar vesicles. Liposomes can be formed from a variety of phospholipids such as lecithin, sphingomyelin, proteolipids, protein-encapsulated vesicles or from cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, asuitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials such as solutol and/or ethanol to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

Specific examples of pharmaceutically acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric-coated to prevent release of the active ingredient compounds before they reach the small intestine. Materials that may be used as enteric coatings include, but are not limited to, sugars, fatty acids, proteinaceous substances such as gelatin, waxes, shellac, cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers. The compounds and compositions of the invention can be coated onto stents for temporary or permanent implantation into the cardiovascular system of a subject.

Variations on those general synthetic methods will be readily apparent to those of ordinary skill in the art and are deemed to be within the scope of the present invention.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

General Procedures for Synthesis.

Melting points were determined on a Thomas Hoover capillary melting point apparatus and are uncorrected. The 400 MHz $^1$H and 100 MHz $^{13}$C NMR were recorded on a Bruker Avance 400 NMR spectrometer unless otherwise stated. The chemical shifts are reported in δ (ppm) using the δ 7.27 signal of CHCl$_3$ ($^1$H NMR) and δ 77.23 signal of CDCl$_3$ ($^{13}$C NMR), or the δ 29.92 signal of CO(CD$_3$)$_2$ ($^{13}$C NMR) as internal standards. Coupling constants are reported in hertz (Hz) and the apparent multiplicity is described as s=singlet, d=doublet, t=triplet, q=quartet, m=multiplet, and br=broad. High-resolution mass spectroscopy data were obtained by an Agilent 6224AA TOF LC/MS system.

Elemental analyses were performed by Atlantic Microlab Inc. All samples prepared for elemental analysis were dried at 50-60° C. at reduced pressure (<0.1 Torr) in a National Appliance Company model 5831 vacuum oven unless otherwise stated. TLC was performed using plates precoated with silica gel 60 F$_{254}$. Flash column chromatography was done with silica gel (230-400 mesh). Anhydrous THF and CH$_2$Cl$_2$ were obtained from a solvent purification system unless otherwise stated. All other solvents (analytical grade) including anhydrous solvents and reagents were used as received. All references to "water" correspond to reverse osmosis deionized (RODI) water. All references to "brine" refer to a saturated aqueous sodium chloride solution. The term "in vacua" refers to solvent removal by rotary evaporation followed by a lower pressure environment (≤0.2 Torr). All experiments were performed under a nitrogen atmosphere. As the elemental analyses of compounds 4-15 are consistent with their molecular formula within ±0.4%, their purity is determined to be greater than 95%.

Calculation of Approximate Equilibrium Constant (K)
Calculation of K of 3
The concentrations of 3, with initial concentration of 0.1 mM, and DTT, with initial concentration of 0.1 mM, in the phosphate buffer are calculated to be 0.085$_5$ mM as follows: (1) The absorbance (A) is 0.956 at 0.1 mM concentration of 3 in deionized water. (2) The A of 3 is 0.817 in the phosphate buffer. (3) The concentrations of 3 and DTT in the buffer are calculated to be 0.085$_5$ mM based on (1) and (2). From these concentrations, the approximate K is calculated as follows:

$K=[Adduct]/[3]\times[DTT]=0.0145\times10^{-3}/0.0855\times0.855\times10^{-6}=2.0\times10^3$ (Liters/mol).

Calculation of K of 4-8

Unfortunately, since the $\lambda_{max}$ of 4-8 was not observed due to the overlapping, we can't calculate the concentrations of the adducts of 4-8 by the same method as for 3. However, since we can speculate that the ε of the adducts of 4-8 is almost similar to that of the adduct of 2, we can calculate the concentrations of the adducts of 4-8 based on the A (0.227 at 0.0145 mM) of the adduct of 2 and the A of the adducts of 4-8. For example, the concentration of the adduct of 5 is 0.0145×0.369 (A of the adduct of 5)/0.227=0.0235 (mM). Therefore, the concentrations of 5 and DTT are 0.0765 (mM/each). Thus, K of 5=0.0235×10$^{-3}$/0.0765×0.0765×10$^{-6}$=4.0×10$^3$ (Liters/mol). The K of 4 and 6-8 are also calculated using the A (0.227 at 0.0145 mM) of the adduct of 3 and the A of the adducts of 4 and 6-8, respectively.

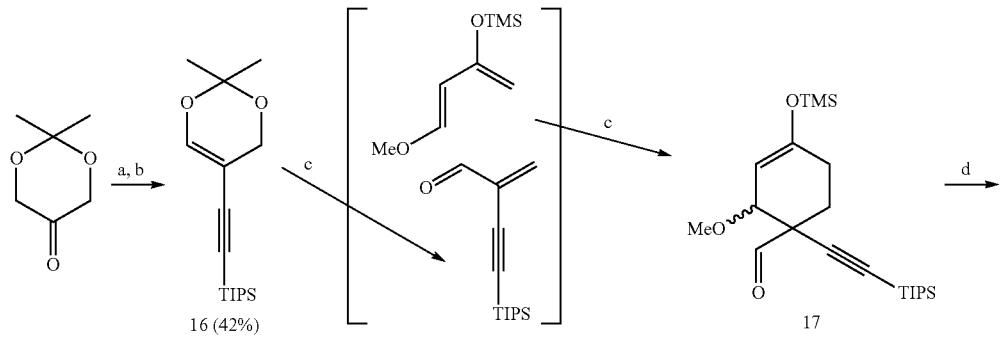

Scheme 1.$^a$ Synthesis of monocyclic ethynylcyanodienone 4

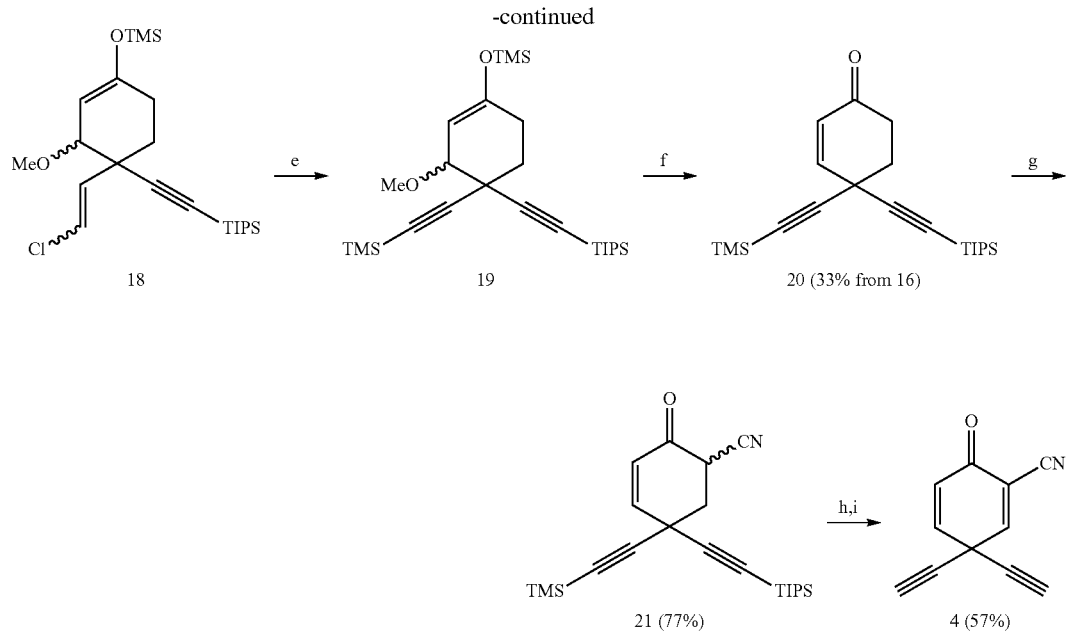

2-Oxo-5-(((triisopropylsilyl)ethynyl)-5-((trimethylsilyl)ethynyl) cyclohex-3-enecarbonitrile (21)

To a solution of 20 (83 mg, 0.22 mmol) in THF (3 mL) was added LDA (2M solution in THF/n-heptane/ethylbenzene, 0.44 mL, 0.88 mmol, 4 eq) at −78° C. (in an isopropanol-dry ice bath). The mixture was allowed to reach rt over 30 min. To the mixture was added a cloudy solution of p-TsCN (95%, 201 mg, 1.1 mmol, 5 eq) in THF (0.7 mL) at −78° C. The mixture was stirred at −78° C. for 50 min. To the reaction mixture was added 28% aqueous $NH_3$ (0.5 mL) at −78° C. The mixture was allowed to reach rt. The mixture was extracted with $CH_2Cl_2$-$Et_2O$ (1:2, 30 mL×3). The extract was washed with saturated aqueous $NaHCO_3$ solution (10 mL) and brine (20 mL×2), dried over $MgSO_4$, filtered, and concentrated in vacuo to give an oil, which was purified by flash chromatography [hexanes/$CH_2Cl_2$ (1:3) and then hexanes/EtOAc (10:1)] to give 21 (a mixture of two isomers, 68 mg, 77%) as an oil: $^1H$ NMR ($CDCl_3$) δ 6.82-6.95 (1H, m), 6.03 (1H, dd, J=2 and 10 Hz), 3.95-4.06 (1H, m), 2.80-2.90 (1H, m), 2.60-2.74 (1H, m), 1.02-1.12 (21H, brs), 0.19 (9H, s); $^{13}C$ NMR ($CDCl_3$) δ 187.0, 186.9, 149.9, 149.8, 125.6, 125.4, 115.8, 115.7, 104.5, 102.2, 101.2, 99.1, 90.4, 88.8, 87.4, 85.5, 40.3, 37.8, 37.7, 32.6, 18.7, 11.3, 11.3, −0.1, −0.2.

5,5-Diethynyl-2-oxocyclohex-3-enecarbonitrile

To a solution of 21 (66 mg, 0.166 mmol) in THF (0.8 mL) was added a TBAF solution (1 M in THF, 0.83 mL, 0.83 mmol, 5 eq) at 0° C. The solution was stirred at 0° C. for 3 h. Then, the reaction mixture was diluted with $CH_2Cl_2$-$Et_2O$ (1:2, 10 mL) and acidified with 1M aqueous HCl solution. The organic phase was washed with water (3 mL) and brine (3 mL×2), dried over $MgSO_4$, filtered, and concentrated in vacuo to give a solid, which was purified by flash chromatography [petroleum ether/$Et_2O$ (5:1)] to give the titled compound (a mixture of two isomers, 21 mg, 73%) as a colorless solid. $^1H$ NMR ($CDCl_3$) δ 6.90 (1H, dd, J=2 and 10 Hz), 6.09 (1H, d, J=10 Hz), 4.03 (1H, dd, J=4 and 9.6 Hz), 2.90 (1H, ddd, J=1, 2 and 9.2 Hz), 2.71 (1H, t, J=9.6 Hz), 2.55 (1H, s), 2.51 (1H, s); $^{13}C$ NMR ($CDCl_3$) δ 186.5, 148.5, 126.3, 115.4, 80.8, 78.3, 73.7, 72.4, 39.8, 37.6, 30.6;

3,3-Diethynyl-6-oxocyclohexa-1,4-dienecarbonitrile (4)

To a stirred solution of PhSeCl (46 mg, 0.24 mmol) in anhydrous $CH_2Cl_2$ (0.18 mL) was added a solution of pyridine (21 mg, 0.27 mmol) in anhydrous $CH_2Cl_2$ (0.5 mL) at 0° C. After the mixture was stirred for 15 min, to the mixture was added a solution of 5,5-Diethynyl-2-oxocyclohex-3-enecarbonitrile (20 mg, 0.12 mmol) in anhydrous $CH_2Cl_2$ (0.7 mL). The mixture was stirred at 0° C. for 1 h, and then it was washed with 5% aqueous HCl solution (0.3 mL×2). To the organic solution was added 30% aqueous $H_2O_2$ solution (10 μL) three times at 0° C. at 10 min interval. Twenty min after the 3rd addition, the reaction mixture was diluted with $CH_2Cl_2$ (20 mL). The mixture was washed with water (5 mL), saturated aqueous $NaHCO_3$ solution (5 mL×2) and brine (5 mL×2), dried over $MgSO_4$, filtered, and concentrated in vacuo to give a residue, which was purified by flash column chromatography [petroleum ether/$Et_2O$ (5:1)] to give 4 (15 mg, 76%) as a crystalline solid: mp: 110-111° C.; $^1H$ NMR ($CDCl_3$) δ 7.49 (1H, d, J=2.8 Hz); 6.96 (1H, dd, J=2.8 and 10 Hz), 6.39 (1H, d, J=10 Hz), 2.58 (2H, s); $^{13}C$ NMR ($CDCl_3$) δ 176.9, 153.3, 144.7, 126.7, 116.6, 112.8, 75.0, 74.2, 32.2; HRMS (ESI+) calcd for $C_{11}H_5NO+H$, 168.0443, found 168.0444. Anal. Calcd for $C_{11}H_5NO \cdot 1/6\ H_2O$: C, 77.64; H, 3.16; N, 8.23. Found: C, 77.66; H, 3.17; N, 8.17.

Scheme 2.[a] Synthesis of monocyclic ethynylcyanodienone 5

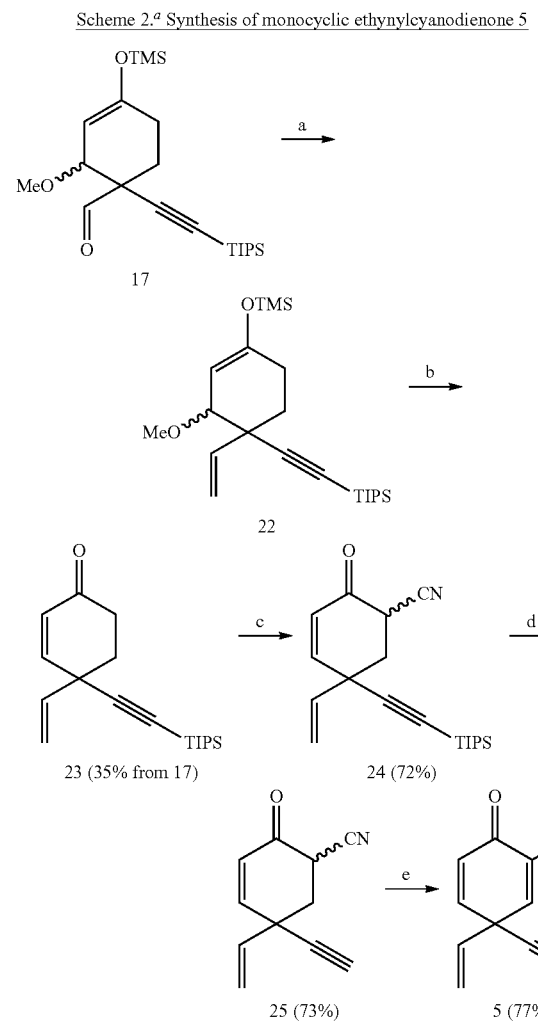

[a]Reagents: (a) Ph₃PCH₂I, n-BuLi, THF; (b) D-(+)-CSA, dioxane; (c) p-TsCN, LDA, THF; (d) TBAF, THF; (e) PhSeCl, pyridine, CH₂Cl₂; 30% aqueous H₂O₂, CH₂Cl₂.

4-((Triisopropylsilyl)ethynyl)-4-vinylcyclohex-2-enone (23)

To a suspension of methyltriphenylphosphonium iodide (939 mg, 2.32 mmol, 1.55 eq) in anhydrous THF (8 mL) was added n-BuLi (1.6 M in hexanes, 1.45 mL, 2.32 mmol, 1.55 eq) dropwise at 0° C. and the reaction mixture was stirred at rt for 30 min. To the reaction mixture was added a solution of 17 (700 mg, crude, 1.50 mmol) in anhydrous THF (6 mL) dropwise at 0° C. The reaction mixture was allowed to reach rt and stirred for 3 h. Then, 15% aqueous NH₄Cl (5 mL) solution was added. The aqueous mixture was extracted with CH₂Cl₂-Et₂O (1:2, 20 mL×3). The extract was washed with saturated aqueous NaHCO₃ solution (10 mL×1) and brine (20 mL×2), dried over MgSO₄, filtered, and concentrated in vacuo to give oil. This oil was diluted with Et₂O (30 mL), filtered, and concentrated in vacuo to give crude 22 as an oil. To a solution of 22 in dioxane (10 mL) was added CSA (71.5 mg, 0.308 mmol, 0.2 eq). This mixture was heated under reflux for 7 h. The reaction mixture was cooled to rt and then water (10 mL) was added to quench it. The aqueous mixture was extracted with CH₂Cl₂-Et₂O (1:2, 30 mL×3). The extract was washed with saturated aqueous NaHCO₃ solution (30 mL×2) and brine (30 mL×2), dried over MgSO₄, filtered, and concentrated in vacuo to give an oil, which was purified by flash column chromatography [hexanes/Et₂O (2:1) and then hexanes/CH₂Cl₂ (1:1)] to give the titled compound 23 (158 mg, 35% from 17) as an oil: ¹H NMR (CDCl₃) δ 6.67 (1H, dd, J=0.8 and 10 Hz), 5.97 (1H, d, J=10 Hz), 5.84 (1H, dd, J=10 and 17.2 Hz), 5.53 (1H, dd, J=0.8 and 17.2 Hz), 5.26 (1H, dd, J=0.8 and 10 Hz), 2.65-2.80 (1H, m), 2.44-2.55 (1H, m), 2.24-2.35 (1H, m), 2.04-2.20 (1H, m), 1.06 (21H, brs); ¹³C NMR (CDCl₃) δ 198.6, 151.2, 139.1, 128.3, 116.3, 106.6, 86.2, 41.0, 36.0, 34.9, 18.8, 11.3; HRMS (ESI+) calcd for C₁₉H₃₁OSi+H, 303.2139, found 303.2143.

2-Oxo-5-((triisopropylsilyl)ethynyl)-5-vinylcyclohex-3-enecarbonitrile (24)

To a solution of 23 (140 mg, 0.46 mmol) in anhydrous THF (5.2 mL) was added LDA (2M solution in THF/n-heptane/ethylbenzene, 0.67 mL, 1.33 mmol, 2.9 eq) at −78° C. (in an isopropanol-dry ice bath). The mixture was allowed to reach rt over 30 min. To the mixture was added a cloudy solution of p-TsCN (95%, 333 mg, 1.84 mmol, 4 eq) in anhydrous THF (3.8 mL) at −78° C. The mixture was stirred at −78° C. for 50 min. To the reaction mixture was added 28% aqueous ammonia solution (0.5 mL) at −78° C. The mixture was allowed to reach rt. The mixture was extracted with CH₂Cl₂-Et₂O (30 mL×3). The extract was washed with saturated aqueous NaHCO₃ solution (10 mL) and brine (20 mL×2), dried over MgSO₄, filtered, and concentrated in vacuo to give an oil, which was purified by flash column chromatography [hexanes/EtOAc (8:1) and then (6:1)] to give 24 (a mixture of two isomers, 110 mg, 72%) as an oil: ¹H NMR (CDCl₃) δ 6.80 (0.38H, dd, J=2 and 10 Hz), 6.73 (1H, dd, J=2 and 10 Hz), 6.16 (0.38H, dd, J=10 Hz), 6.06 (1H, d, J=10 Hz), 5.89 (0.38H, dd, J=10 and 17.2 Hz), 5.79 (1H, dd, J=10 and 16.8 Hz), 5.66 (1H, dd, J=0.8 and 16.8 Hz), 5.30-5.45 (m, 1H+2×0.38H), 4.10 (1H, dd, J=4 and 14 Hz), 3.66 (0.38H, dd, J=4.4 and 14 Hz), 2.75 (0.38H, t, J=13.6 Hz), 2.50-2.60 (1.38H, m), 2.42 (1H, t, J=13.6 Hz), 1.07 (21H, s), 1.07 (21×0.38H); ¹³C NMR (CDCl₃) δ 187.7, 187.3, 151.9, 151.7, 137.9, 135.8, 127.0, 126.1, 118.5, 117.9, 116.3, 116.0, 106.8, 102.6, 89.8, 86.5, 41.2, 40.5, 39.7, 38.8, 38.2, 36.7, 18.8, 18.8, 11.2, 11.2.

5-Ethynyl-2-oxo-5-vinylcyclohex-3-enecarbonitrile (25)

To a solution of 24 (74 mg, 0.166 mmol) in THF (0.8 mL) was added a TBAF solution (1 M in THF, 0.9 mL, 0.9 mmol, 4 eq) at 0° C. After the mixture was stirred at rt for 3 h, it was diluted with CH₂Cl₂-Et₂O (1:2, 100 mL) and acidified with 1M aqueous HCl solution. The organic layer was washed with water (20 mL) and brine (10 mL×2), dried over MgSO₄, filtered, and concentrated in vacuo to give a solid, which was purified by flash column chromatography [petroleum ether/Et₂O (5:1) and then (3:1)] to afford 25 (a mixture of two isomers, 28 mg, 73%) as a colorless solid. ¹H NMR (CDCl₃) δ 6.81 (0.59H, dd, J=2 and 10 Hz), 6.72 (1H, dd, J=2 and 10 Hz), 6.19 (0.59H, d, J=10 Hz), 6.09 (1H, d, J=10 Hz), 5.90 (0.59H, dd, J=10 and 17.2 Hz), 5.80 (1H, dd, J=10 and 16.8 Hz), 5.63 (1H, d, J=16.8 Hz), 5.30-5.45 (1H+2× 0.59H, m), 4.11 (1H, dd, J=4.4 and 13.6 Hz), 3.66 (0.59H, dd, J=4.4 and 13.6 Hz), 2.76 (0.59H, t, J=13.6 Hz), 2.55-2.64 (2H+0.59H, m), 2.46 (1H, d, J=11.2 Hz), 2.40 (0.59H, d, J=13.6 Hz); ¹³C NMR (CDCl₃) δ 187.5, 187.1, 151.1, 151.0, 137.5, 135.5, 127.4, 126.8, 118.9, 118.0, 116.1, 115.8, 83.5, 80.0, 75.9, 73.4, 39.9, 39.3, 38.3, 38.2, 36.6; HRMS (ESI+) calcd for $C_{11}H_9NO+H^+$: 172.0757, found 172.0796.

3-Ethynyl-6-oxo-3-vinylcyclohexa-1,4-dienecarbonitrile (5)

To a stirred solution of PhSeCl (55.8 mg, 0.292 mmol) in anhydrous $CH_2Cl_2$ (2.9 mL) was added a solution of pyridine (25.4 mg, 0.32 mmol) in anhydrous $CH_2Cl_2$ (0.4 mL) at 0° C. After the mixture was stirred for 15 min, a solution of 25 (25 mg, 0.146 mmol) in anhydrous $CH_2Cl_2$ (0.7 mL) was added. Then, the reaction mixture was stirred at 0° C. for 1 h. The reaction mixture was washed with 5% aqueous HCl solution (0.3 mL×2). To the organic layer was added 30% aqueous $H_2O_2$ solution (50 L) and the mixture was stirred at 0° C. for 10 min. Then, additional 30% aqueous $H_2O_2$ solution (30 µL) was added. After the mixture was stirred for 10 min, to the mixture was added additional 30% aqueous $H_2O_2$ solution dropwise until the yellow color disappeared. This colorless mixture was stirred at 0° C. for additional 20 min. After the reaction mixture was diluted with $CH_2Cl_2$ (20 mL), it was washed with water (5 mL), saturated aqueous $NaHCO_3$ solution (5 mL×2) and brine (5 mL×2), dried over $MgSO_4$, filtered, and concentrated in vacuo to give a residue, which was purified by flash column chromatography [petroleum ether/$Et_2O$ (5:1)] to afford 5 (19 mg, 77%) as a crystalline solid: mp 76.0-77.0° C.; $^1$H NMR ($CDCl_2$) δ 7.39 (1H, d, J=2.8 Hz); 6.83 (1H, dd, J=2.8 and 10 Hz), 6.39 ($^1$H, d, J=10 Hz), 5.72-5.85 (1H, m), 5.49-5.57 (2H, m), 2.65 (1H, s); $^{13}$C NMR ($CDCl_2$) δ 177.8, 157.5, 148.3, 131.9, 127.1, 121.1, 116.6, 113.3, 76.9, 76.3, 43.4; HRMS (ESI+) calcd for $C_{11}H_7NO+H$, 170.0536, found 170.0609. Anal. Calcd for $C_{11}H_7NO·1/8\ H_2O$: C, 77.07; H, 4.26; N, 8.17. Found: C, 77.06; H, 4.21; N, 8.10.

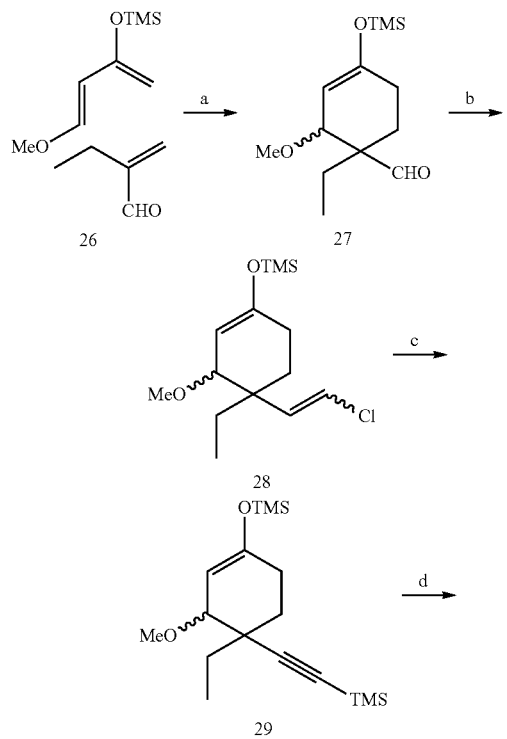

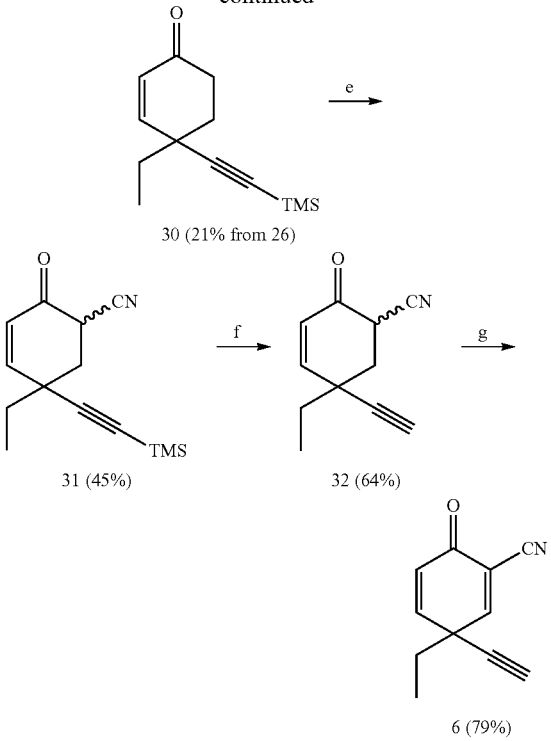

[a]Reagents: (a) microwave at 120° C.; (b) $Ph_3PCH_2Cl_2$, n-BuLi, THF; (c) TMSCl, LDA, THF; (d) TFA, $CHCl_3$; (e) p-TsCN, LDA, THF; (f) TBAF, THF; (g) PhSeCl, pyridine, $CH_2Cl_2$; 30% aqueous $H_2O_2$, $CH_2Cl_2$.

4-Ethyl-4-(((triisopropylsilyl)ethynyl)cyclohex-2-enone (30)

A mixture of ethyl acrolein (26) (252 mg, 3 mmol) and Danishefsky's diene (674 mg, 3.9 mmol, 1.3 eq) was heated at 120° C. for 1.5 h using microwave to give a crude adduct 27, which was used for the next step without further purification.

To a suspension of (chloromethyl)triphenylphosphonium chloride (1.35 g, 3.9 mmol, 1.3 eq) in anhydrous THF (22 mL) was added n-BuLi (1.6 M in hexanes, 2.2 mL, 3.45 mmol, 1.15 eq) dropwise at 0° C. The mixture was stirred at rt for 30 min. To the mixture was added a solution of 27 (the crude, 3 mmol) in anhydrous THF (7 mL) dropwise at 0° C. The mixture was allowed to reach rt and stirred for 3 h. Then, to the reaction mixture was added a solution of LDA (2 M in THF/n-heptane/ethylbezenre, 7.5 mL, 15 mmol, 5 eq) at 0° C. The resultant mixture was stirred at 0° C. for 1 h.

To the mixture containing 28 was added TMSCl (0.4 mL) dropwise at 0° C. After the mixture was stirred at 0° C. for 2 h, water (5 mL) was added. The aqueous mixture was extracted with $CH_2Cl_2$-$Et_2O$ (1:2, 20 mL×3). The extract was washed with saturated aqueous $NaHCO_3$ solution (10 mL×1) and brine (20 mL×2), dried over $MgSO_4$, filtered, and concentrated in vacuo to give an oil. The oil was diluted with $Et_2O$ (30 mL), filtered, and concentrated in vacuo to afford a crude 29 as an oil, which was used for the next step without further purification.

To a solution of 29 (the crude) in chloroform (9 mL) was added trifluoroacetic acid (1 mL). The mixture was heated under reflux for 5 h. The reaction mixture was concentrated in vacuo to give an oil. The oil was diluted with CH₂Cl₂-Et₂O (1:2, 80 mL). The solution was washed with saturated aqueous NaHCO₃ solution (30 mL×2) and brine (30 mL×2), dried over MgSO₄, filtered, and concentrated in vacuo to give an oil, which was purified by flash column chromatography [petroleum ether/Et₂O (15:1)] to afford the titled compound 30 (158 mg, 35% from 26) as an oil: $^1$H NMR (CDCl₃) δ 6.72 (1H, dd, J=1.6 and 10 Hz), 5.92 (1H, d, J=10 Hz), 2.65-2.80 (1H, m), 2.45 (1H, dt,
J=4.8 and 16.8 Hz), 2.12-2.25 (1H, m), 1.86-1.99 (1H, m), 1.59-1.79 (2H, m), 1.08 (3H, t, J=7.6 Hz), 0.15 (9H, s); $^{13}$C NMR (CDCl₃) δ 199.4, 151.8, 128.0, 106.6, 87.9, 37.9, 35.1, 34.1, 33.6, 9.0, 0.3; HRMS (ESI+) calcd for C₁₃H₂₀OSi+H, 220.1356, found 220.1357.

5-Ethyl-2-oxo-5-((trimethylsilyl)ethynyl)cyclohex-3-enecarbonitrile (31)

To a solution of 30 (128 mg, 0.58 mmol) in anhydrous THF (7 mL) was added LDA (2M solution in THF/n-heptane/ethylbenzene, 0.87 mL, 1.74 mmol, 3 eq) at −78° C. (in an isopropanol-dry ice bath). The mixture was allowed to reach rt over 30 min. To the mixture was added a cloudy solution of p-TsCN (95%, 526 mg, 2.9 mmol, 5 eq) in anhydrous THF (4 mL) at −78° C. The mixture was stirred at −78° C. for 50 min. To the reaction mixture was added 28% aqueous ammonia solution (0.5 mL) at −78° C. The mixture was allowed to reach rt. The mixture was extracted with CH₂Cl₂-Et₂O (1:2, 30 mL×3). The extract was washed with saturated aqueous NaHCO₃ solution (10 mL) and brine (20 mL×2), dried over MgSO₄, filtered, and concentrated in vacuo to give an oil, which was purified by flash column chromatography [petroleum ether/Et₂O (5:1)] to afford 31 (a mixture of two isomers, 64 mg, 45%) as an oil: $^1$H NMR (CDCl₃) (major isomer) δ 6.74 (1H, dd, J=2 and 10 Hz), 6.00 (1H, d, J=10 Hz), 4.02 (1H, dd, J=4 and 14 Hz), 2.42-2.60 (1H, m), 2.19 (1H, t, J=13.6 Hz), 1.55-1.65 (2H, m), 1.07 (3H, t, J=7.6 Hz), 0.15 (9H); $^{13}$C NMR (CDCl₃) (major isomer) δ 188.4, 152.9, 126.1, 116.7, 102.9, 90.6, 38.3, 38.2, 38.1, 33.9, 21.6, 8.6, 0.06; HRMS (ESI+) calcd for C₁₄H₁₉NOSi+NH₄⁺: 345.2357, found 345.2365.

5-Ethyl-5-ethynyl-2-oxocyclohex-3-enecarbonitrile (32)

To a solution of 31 (63 mg, 0.256 mmol) in THF (0.5 mL) was added a TBAF solution (1 M in THF, 0.513 mL, 0.513 mmol, 2 eq) at 0° C. After the mixture was stirred at 0° C. for 3 h, it was diluted with CH₂Cl₂-Et₂O (100 mL) and acidified with 1M aqueous HCl solution. The organic layer was washed with water (20 mL) and brine (10 mL×2), dried over MgSO₄, filtered, and concentrated in vacuo to give a solid, which was purified by flash column chromatography [petroleum ether/Et₂O (5:1)] to afford 32 (a mixture of two isomers, 28 mg, 64%) as a colorless solid: $^1$H NMR (CDCl₃) (major isomer) δ 6.77 (1H, dd, J=2 and 10 Hz), 6.03 (1H, d, J=10 Hz), 4.05 (1H, dd, J=4 and 14 Hz), 2.42-2.60 (1H, m), 2.38 (1H, s), 2.22 (1H, t, J=13.6 Hz), 1.60-1.90 (2H, m), 1.10 (3H, t, J=7.6 Hz); $^{13}$C NMR (CDCl₃) (major isomer) δ 188.1, 152.5, 126.5, 116.5, 81.9, 73.7, 38.3, 38.1, 37.1, 33.7, 8.6; HRMS (ESI+) calcd for C₁₄H₁₉NOSi+174.0913, found 174.0906.

3-Ethyl-3-ethynyl-6-oxocyclohexa-1,4-dienecarbonitrile (6)

To a stirred solution of PhSeCl (62 mg, 0.324 mmol, 2 eq) in anhydrous CH₂Cl₂ (3.5 mL) was added a solution of pyridine (28.2 mg, 0.357 mmol, 2.2 eq) in anhydrous CH₂Cl₂ (0.4 mL) at 0° C. After the mixture was stirred for 15 min, a solution of 32 (28 mg, 0.162 mmol) in anhydrous CH₂Cl₂ (1.5 mL) was added and the mixture was stirred at 0° C. for 1 h. The reaction mixture was washed with 5% aqueous HCl solution (0.7 mL×2). To the organic layer was added 30% aqueous H₂O₂ solution (100 µL) and stirred at 0° C. for 10 min. Then additional 30% aqueous H₂O₂ solution (30 µL) was added. After the mixture was stirred for 10 min, to the mixture was added additional 30% aqueous H₂O₂ solution (30 µL) dropwise until the yellow color disappeared. The colorless solution was stirred at 0° C. for additional 20 min. After the reaction mixture was diluted with CH₂Cl₂ (20 mL), it was washed with water (5 mL), saturated aqueous NaHCO₃ solution (5 mL×2) and brine (5 mL×2), dried over MgSO₄, filtered, and concentrated in vacuo to give a residue, which was purified by flash column chromatography [petroleum ether-Et₂O (5:1)] to afford 6 (22 mg, 79%) as a crystalline solid. mp 73.0-75.0° C.; $^1$H NMR (CDCl₃) δ 7.50 (1H, d, J=2.8 Hz); 6.91 (1H, dd, J=2.8 and 10 Hz), 6.40 (1H, d, J=10 Hz), 2.46 (s, 1H), 1.98 (1H, q, J=7.6 Hz), 1.04 (1H, t, J=7.6 Hz); $^{13}$C NMR (CDCl₃) δ 177.8, 159.5, 149.7, 127.8, 117.4, 113.5, 78.5, 74.2, 40.6, 34.0, 9.1; HRMS (ESI+) calcd for C₁₁H₉NO+H, 172.0757, found 172.0759. Anal. Calcd for C₁₁H₉NO.1/8 H₂O: C, 76.17; H, 5.38; N, 8.08. Found: C, 76.37; H, 5.35; N, 7.92.

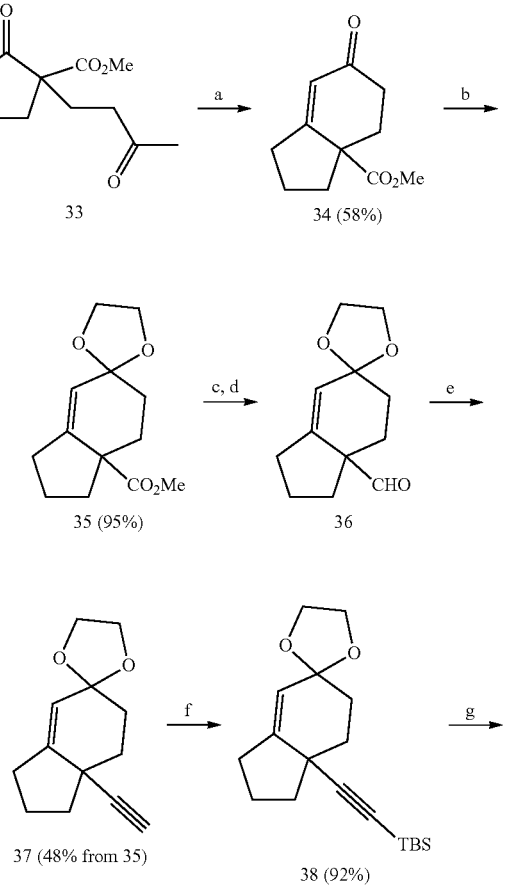

Scheme 4.$^a$ Synthesis of bicyclic ethynylcyanodienone 7

-continued

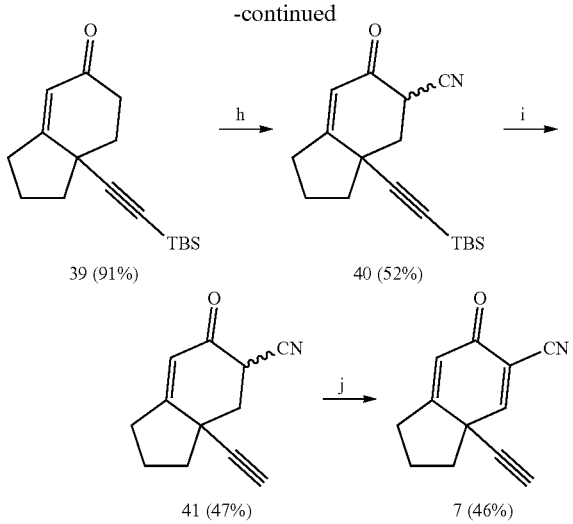

*Reagents: (a) pyrrolidine, AcOH, EtOAc; (b) ethylene glycol, PPTS, toluene; (c) LAH, Et₂O; (d) (COCl)₂, DMSO, CH₂Cl₂; (e) Ohira reagent, K₂CO₃, MeOH; (f) MeLi, TBSCl, THF; (g) 10% aqueous HCl, MeOH; (h) p-TsCN, LDA, THF; (i) TBAF, THF; (j) DDQ, PhH.

Methyl 6-oxo-2,3,3a,4,5,6-hexahydro-1H-indene-3a-carboxylate (34)

To a solution of methyl 2-oxo-1-(3-oxobutyl)cyclopentanecarboxylate (33) (Shirakawa, S. & Shimizu, S. 2007) (1.75 g, 8.25 mmol) in ethyl acetate (5 mL) were added acetic acid (472 µL, 8.248 mmol) and pyrrolidine (677 µL, 8.248 mmol) in sequence at rt. Then the reaction mixture was stirred at rt for 25 h. Subsequently, all volatile materials were removed in vacuo and the residue was purified by flash column chromatography [hexanes/EtOAc/CH₂Cl₂ (5:1:1)] to give 34 (0.92 g, 58%) as a pale yellow oil: $^1$H NMR (CDCl₃) δ 5.95 (1H, s), 3.73 (3H, s), 2.82-2.77 (1H, m), 2.66-2.60 (1H, m), 2.59-2.51 (1H, m), 2.44-2.34 (3H, m), 1.90-1.78 (3H, m), 1.65-1.59 (1H, m); $^{13}$C NMR (CDCl₃) δ 198.8, 174.0, 170.0, 123.6, 54.4, 52.6, 38.4, 34.8, 33.4, 31.9, 22.1; HRMS (ESI+) calcd for $C_{11}H_{14}O_3$+H, 195.1021, found 195.1000.

Methyl 1',2',3',6',7',7a'-hexahydrospiro[[1,3]dioxolane-2,5'-indene]-7a'-carboxylate (35)

A mixture of 34 (286.8 mg, 2.110 mmol), PPTS (53.0 mg), ethylene glycol (944 µL, 16.88 mmol) and anhydrous toluene (25 mL) was heated under reflux for 1 h using a Dean-Stark apparatus. After cooling down to rt, the solvent was removed in vacuo. The resultant residue was treated with water (40 mL) and CH₂Cl₂-Et₂O (2:1, 40 mL). The organic layer was washed with brine, dried over MgSO₄, filtered and concentrated in vacuo to give a residue, which was purified by flash column chromatography [hexanes/EtOAc (6:1)] to afford 35 (333.4 mg, 95%) as a sticky yellow oil: $^1$H NMR (400 MHz, CDCl₃) δ 5.61 (1H, s), 3.99-3.91 (4H, m), 3.70 (3H, s), 2.53 (1H, d, J=13.8 Hz), 2.47-2.36 (4H, m), 2.32-2.27 (1H, m), 1.86-1.81 (1H, m), 1.75-1.71 (2H, m), 1.56-1.49 (1H, m); $^{13}$C NMR (100 MHz, CDCl₃) δ 176.5, 140.7, 127.4, 109.0, 64.5, 64.4, 56.8, 52.0, 37.6, 36.9, 34.0, 32.9, 31.4; HRMS (ESI+) calcd for $C_{13}H_{18}O_4$+H, 239.1283, found 239.1276.

(1',2',3',6',7',7a'-Hexahydrospiro[[1,3]dioxolane-2,5'-inden]-7a'-yl)methanol To a solution of 35 (519 mg, 2.18 mmol) in anhydrous Et₂O (30 mL) was added LAH (190 mg, 5.01 mmol) slowly in batches. The mixture was stirred at rt for 1 h. Subsequently, water (0.30 mL), 40% aqueous NaOH solution (0.21 mL), and water (0.60 mL) were added to the reaction mixture sequentially. After stirring at rt for 1 h, the mixture was decanted and the off-white gummy solid in the reaction flask was washed with Et₂O (25 mL×3). The combined organic layer was dried over MgSO₄, filtered and concentrated in vacuo to give the titled compound (crude, 463 mg) as colorless oil: $^1$H NMR (CDCl₃) δ 5.56 (1H, s), 4.00-3.92 (4H, m), 3.63 (1H, d, J=10.6 Hz), 3.51 (1H, d, J=8.0 Hz), 2.48 (1H, dd, J=13.8 Hz, 2.6 Hz), 2.39-2.26 (3H, m), 2.12 (1H, ddd, J=13.0 Hz, 7.5 Hz, 3.0 Hz), 1.92 (1H, ddd, J=13.4 Hz, 7.5 Hz, 3.0 Hz), 1.78 (1H, ddd, J=14.0 Hz, 14.0 Hz, 4.2 Hz), 1.70-1.64 (1H, m), 1.62-1.48 (2H, m); $^{13}$C NMR (CDCl₃) δ 141.5, 126.7, 109.3, 65.1, 64.5, 64.4, 50.9, 36.4, 35.5, 32.3, 31.7, 31.2; HRMS (ESI+) calcd for $C_{12}H_{18}O_3$+H, 211.1334, found 211.1323.

1',2',3',6',7',7a'-Hexahydrospiro[[1,3]dioxolane-2,5'-inden]-7a'-carbaldehyde (36)

After a CH₂Cl₂ solution (12 mL) of oxalyl chloride (206 µL, 2.40 mmol) was stirred for 20 min at about −65° C. in an isopropanol-dry ice bath, to the solution was added a CH₂Cl₂ solution (2 mL) of DMSO (310 µL, 4.35 mmol) dropwise. After stirring for 10 min, to the reaction mixture was added a CH₂Cl₂ solution (5 mL) of (1',2',3',6',7',7a'-hexahydrospiro[[1,3]dioxolane-2,5'-inden]-7a'-yl)methanol (crude, 463 mg) dropwise and then the mixture was stirred for 20 min at −65° C. After removal of the cooling bath, to the reaction mixture were added Et₃N (1.05 mL) and water (10 mL) successively. After dilution with CH₂Cl₂-Et₂O (1:2, 25 mL), the organic layer was washed with 5% aqueous HCl solution (10 mL), water (20 mL), saturated aqueous NaHCO₃ solution (20 mL), and brine (15 mL), dried over MgSO₄, filtered and concentrated in vacuo to give 36 (crude, 288 mg) as a pale yellow oil: $^1$H NMR (CDCl₃) δ 9.47 (1H, s), 5.70 (1H, s), 3.89 (4H, s), 3.06-3.03 (1H, m), 2.40 (2H, s), 2.26-2.16 (3H, m), 1.68-1.66 (3H, m), 1.51-1.47 (1H, m), 1.37-1.34 (1H, m), 1.20 (1H, s); $^{13}$C NMR (CDCl₃) δ 202.2, 138.8, 128.9, 108.8, 64.4, 64.3, 61.3, 45.7, 37.3, 33.4, 32.2, 31.3, 29.7; HRMS (ESI+) calcd for $C_{12}H_{16}O_3$+H, 209.1178, found 209.1150.

7a'-Ethynyl-1',2',3',6',7',7a'-hexahydrospiro[[1,3]dioxolane-2,5'-indene] (37)

To a solution of 36 (crude, 288 mg) and K₂OC₃ (602 mg, 4.35 mmol) in anhydrous MeOH (40 mL) was added Ohira reagent[3] (502 mg, 2.61 mmol) dropwise. The mixture was stirred at rt overnight. After the reaction mixture was concentrated in vacuo, to the resultant mixture were added water (20 mL) and CH₂Cl₂-Et₂O (1:2, 40 mL). The organic layer was washed with saturated aqueous NaHCO₃ solution. The aqueous layer was extracted with CH₂Cl₂-Et₂O (1:2, 40 mL×3). The combined organic solution was dried over MgSO₄, filtered then concentrated in vacuo to give a residue, which was purified by flash column chromatography [hexanes/EtOAc (10:1)] to afford 37 (215 mg, 48% from 35) as a pale yellow solid. $^1$H NMR (300 MHz, CDCl₃) δ 5.42 (1H, s), 3.95-3.91 (4H, m), 2.57-2.44 (3H, m), 2.41-2.29 (2H, m), 2.18 (1H, s), 2.16-1.99 (2H, m), 1.88-1.78 (1H, m), 1.73-1.68 (1H, m), 1.61-1.50 (1H, m); $^{13}$C NMR (75 MHz, CDCl$_3$) δ 142.0, 124.8, 109.0, 88.3, 69.3, 64.4, 64.3, 45.0, 38.6, 36.9, 36.3, 32.2, 31.1; HRMS (ESI+) calcd for C$_{13}$H$_{16}$O$_2$+H, 205.1229, found 205.1200.

tert-Butyl((1',2',3',6',7',7a'-hexahydrospiro[[1,3]dioxolane-2,5'-inden]-7a'-yl)ethynyl)dimethylsilane (38)

To a solution of 37 (102 mg, 0.50 mmol) in anhydrous THF (10 mL) was added a solution of MeLi (1.6 M in Et$_2$O, 0.78 mL, 1.25 mmol) at 0° C. The mixture was stirred at −78° C. for 30 min. Then a solution of TBSCl (188 mg, 1.25 mmol) in anhydrous THF (1 mL) was added to the reaction mixture at −78° C. The reaction mixture was slowly warmed up to rt and stirred at rt for 3.5 h. Then, the reaction was quenched by 15% aqueous NH$_4$Cl solution (3 mL). The reaction mixture was diluted with ethyl acetate and water. The organic layer was washed with brine, dried over MgSO$_4$, filtered and concentrated in vacuo to give a residue, which was purified by flash column chromatography [hexanes/EtOAc (10:1)] to afford 38 (147 mg, 92%) as a colorless crystalline solid: $^1$H NMR (500 MHz, CDCl$_3$) δ 5.41 (1H, s), 4.00-3.91 (4H, m), 2.58-2.45 (3H, m), 2.39-2.30 (2H, m), 2.13 (1H, ddd, J=13.8 Hz, 13.8 Hz, 3.9 Hz), 2.02 (1H, ddd, J=12.8 Hz, 3.4 Hz, 3.4 Hz), 1.83 (1H, ddd, J=12.5 Hz, 8.5 Hz, 8.5 Hz), 1.72 (1H, ddd, J=13.5 Hz, 5.8 Hz, 3.1 Hz), 1.55 (1H, ddd, J=13.8 Hz, 12.9 Hz, 3.4 Hz), 0.92 (9H, s), 0.07 (6H, s); $^{13}$C NMR (125 MHz, CDCl$_3$) δ 142.3, 124.5, 111.4, 109.2, 83.3, 64.5, 64.4, 46.2, 38.8, 37.2, 36.4, 32.5, 31.1, 26.1, 16.7, -4.4; HRMS (ESI+) calcd for C$_{19}$H$_{30}$O$_2$Si+H, 319.2093, found 319.2090.

7a'-((tert-Butyldimethylsilyl)ethynyl)-2,3,7,7a-tetrahydro-1H-inden-5(6H)-one (39)

To a solution of 38 (147 mg, 0.72 mmol) in MeOH (25 mL) was added 10% aqueous HCl solution (8 mL). The mixture was stirred at rt for 2 h. The reaction mixture was carefully neutralized with Et$_3$N (5 mL). After most of the solvent was removed in vacuo, to the resultant mixture were added water (25 mL) and EtOAc (40 mL). The aqueous phase was extracted with EtOAc (25 mL×3). The combined organic solution was washed with brine, dried over MgSO$_4$, filtered and concentrated in vacuo to give a residue, which was purified by flash column chromatography [hexanes/EtOAc (5:1)] to afford 39 (115 mg, 91%) as colorless crystals: $^1$H NMR (500 MHz, CDCl$_3$) δ 5.85 (1H, s), 2.91-2.84 (2H, m), 2.57-2.50 (1H, m), 2.45 (1H, ddd, J=17.2 Hz, 2.8 Hz, 2.8 Hz), 2.38 (1H, ddd, J=12.7 Hz, 4.8 Hz, 2.4 Hz), 2.29-2.12 (1H, m), 1.96-1.92 (1H, m), 1.86 (1H, ddd, J=14.4 Hz, 12.7 Hz, 3.9 Hz), 1.57 (1H, ddd, J=11.9 Hz, 11.9 Hz, 9.4 Hz); $^{13}$C NMR (125 MHz, CDCl$_3$) δ 199.3, 172.2, 121.9, 107.0, 85.2, 43.7, 40.6, 35.1, 34.8, 30.4, 26.0, 22.2, 16.7, -4.7; HRMS (ESI+) calcd for C$_{17}$H$_{26}$OSi+H, 275.1831, found 275.1830.

3a-((tert-Butyldimethylsilyl)ethynyl)-6-oxo-2,3,3a,4,5,6-hexahydro-1H-indene-5-carbonitrile (40)

To a solution of 39 (115 mg, 0.42 mmol) in anhydrous THF (4 mL) was added a solution of LDA (2.0 M in heptane/THF/ethylbenzene) at −78° C. The reaction mixture was stirred at −78° C. for 1 h. Then, a solution of p-TsCN (96 mg, 0.50 mmol) in anhydrous THF (2 mL) was added to the reaction mixture, and then the reaction mixture was stirred at −78° C. for 30 min. The mixture was then allowed to warm up to rt and was quenched by addition of saturated aqueous NH$_4$OH solution (2 mL) and 15% aqueous NH$_4$Cl solution (2 mL). The mixture was extracted with EtOAc (25 mL×3). The combined organic extracts were washed with saturated aqueous NaHCO$_3$ solution (25 mL×2) and brine (30 mL×2), dried over MgSO$_4$, filtered and concentrated in vacuo to give a residue, which was purified by flash column chromatography [hexanes/EtOAc (6:1)] to give 40 (65 mg, 52%) as colorless crystals: $^1$H NMR (CDCl$_3$) δ 5.91 (1H, s), 4.07 (1H, d, J=12.9 Hz, 4.2 Hz), 2.84 (1H, ddd, J=19.8 Hz, 10.0 Hz, 1.3 Hz), 2.73 (1H, dd, J=12.5 Hz, 4.2 Hz), 2.60-2.52 (1H, m), 2.29 (1H, dd, J=12.0 Hz, 6.6 Hz), 2.23-2.09 (2H, m), 2.00-1.92 (1H, m), 1.59 (1H, ddd, J=12.0 Hz, 12.0 Hz, 7.5 Hz), 0.91 (9H, s), 0.10 (3H, s), 0.09 (3H, s); $^{13}$C NMR (CDCl$_3$) δ 187.9, 173.5, 120.1, 117.0, 104.3, 88.0, 43.5, 40.2, 39.1, 37.7, 30.6, 26.0, 22.1, 16.6, -4.8; HRMS (ESI+) calcd for C$_{18}$H$_{25}$NOSi+H, 300.1784, found 300.1783.

3a-Ethynyl-6-oxo-2,3,3a,4,5,6-hexahydro-1H-indene-5-carbonitrile (41)

To a solution of 40 (100 mg, 0.33 mmol) in anhydrous THF (12 mL) was added a solution of TBAF (1.0 M in THF, 0.33 mmol) at rt. The reaction mixture was stirred at rt overnight. The reaction was quenched by addition of saturated aqueous NH$_4$OH solution (5 mL) and 5% aqueous HCl solution (2 mL). The mixture was extracted with EtOAc (25 mL×3). The combined organic extract was washed with saturated aqueous NaHCO$_4$ solution (25 mL×2) and brine (25 mL×2), dried over MgSO$_4$, filtered and concentrated in vacuo to give a residue, which was purified by flash column chromatography [hexanes/EtOAc (3:1)] to afford 41 (29 mg, 47%) as a colorless oil: $^1$H NMR (500 MHz, CDCl$_4$) δ 5.93 (1H, s), 4.08 (1H, dd, J=13.7 Hz, 4.2 Hz), 2.84-2.82 (1H, m), 2.76 (1H, dd, J=12.6 Hz, 4.2 Hz), 2.62-2.52 (1H, m), 2.34 (1H, s), 2.32-2.28 (1H, m), 2.25-2.10 (2H, m), 2.01-1.93 (1H, m), 1.61 (1H, ddd, J=12.1 Hz, 12.1 Hz, 7.5 Hz); HRMS (ESI+) calcd for C$_{12}$H$_{11}$NO+H, 186.0919, found 186.0905.

3a-Ethynyl-6-oxo-2,3,3a,6-tetrahydro-1H-indene-5-carbonitrile (7)

To a solution of 41 (40 mg, 0.22 mmol) in PhH was added DDQ (74 mg, 0.33 mmol) at rt. The mixture was stirred under reflux for 6 h. After the reaction was completed (monitored by LC-MS), the reaction mixture was concentrated and directly subjected to flash column chromatography [petroleum ether-Et$_2$O (3:2)] to give 7 (19 mg, 46%) as colorless crystals: mp 107.0-108.0° C.; $^1$H NMR (CDCl$_3$) δ 7.66 (1H, s), 6.19 (1H, s), 3.04-2.95 (1H, m), 2.63-2.55 (1H, m), 2.41-2.32 (2H, m), 2.38 (1H, s), 2.13-2.04 (1H, m), 1.76-1.65 (1H, m), 0.90 (9H, s), 0.08 (3H, s), 0.07 (3H, s); $^{13}$C NMR (CDCl$_3$) δ 178.6, 168.5, 155.8, 121.5, 117.2, 113.8, 79.0, 72.9, 43.7, 36.8, 29.0, 21.4; HRMS (ESI+) calcd for C$_{22}$H$_9$NO+H, 184.0762, found 184.0759. Anal. Calcd for C$_{12}$H$_9$NO.1/7H$_2$O: C, 77.58; H, 5.04; N, 7.54. Found: C, 77.71; H, 5.07, N, 7.43.

Scheme 5.<sup>a</sup> Synthesis of bicyclic ethynylcyanodienone 8

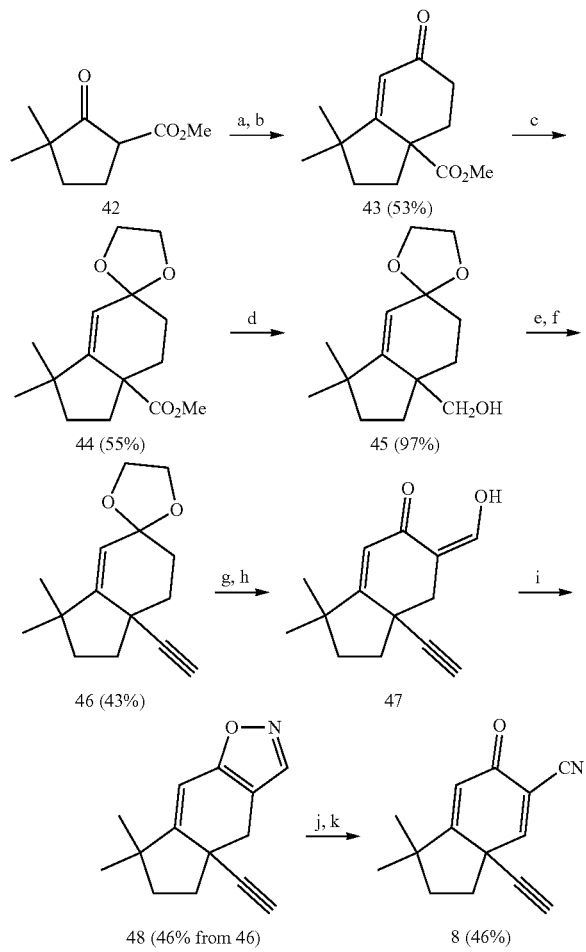

<sup>a</sup>Reagents: (a) methyl vinyl ketone, Et₃N; (b) pyrrolidine, AcOH, toluene; (c) ethylene glycol, PPTS, toluene; (d) LAH, Et₂O; (e) (COCl)₂, DMSO, CH₂Cl₂; (f) Ohira reagent, K₂CO₃, MeOH; (g) 10% aqueous HCl, MeOH; (h) HCO₂Et, NaH, THF; (i) NH₂OH·HCl, aqueous EtOH; (j) NaOMe, MeOH; (k) DDQ, PhH.

Methyl 3,3-dimethyl-2-oxo-1-(3-oxobutyl)cyclopentanecarboxylate

A mixture of methyl 3,3-dimethyl-2-oxocyclopentanecarboxylate (42, 2.10 g, 12.34 mmol) (Ohira, S. 1989), methyl vinyl ketone (1.116 mL, 13.37 mmol), and Et₃N (372 μL, 2.68 mmol) was stirred at rt for 3 h. Then, the volatiles were removed in vacuo to give a residue, which was purified by flash column chromatography [hexanes/EtOAc (5:1)] to afford the titled compound (2.14 g, 100%) as a pale yellow oil: $^1$H NMR (500 MHz, CDCl₃) δ 3.71 (1H, s), 2.70-2.64 (1H, m), 2.50-2.37 (2H, m), 2.21-2.10 (4H, m), 1.92-1.80 (4H, m), 1.11 (3H, s), 1.07 (3H, s); $^{13}$C NMR (125 MHz, CDCl₃) δ 207.7, 172.0, 59.3, 52.5, 46.2, 38.9, 35.3, 30.6, 29.9, 27.8, 24.8, 24.7; HRMS (ESI+) calcd for C₁₃H₂₀O₄+H, 241.1440, found 241.1430.

Methyl 1,1-dimethyl-6-oxo-2,3,3a,4,5,6-hexahydro-1H-indene-3a-carboxylate (43)

To a solution of methyl 3,3-dimethyl-2-oxo-1-(3-oxobutyl)cyclopentanecarboxylate (1.00 g, 4.16 mmol) in toluene (20 mL) were added acetic acid (238 μL, 4.161 mmol) and pyrrolidine (342 μL, 4.161 mmol) in sequence at rt. The reaction mixture was heated under reflux for 12 h. After cooling down to rt, the solvent was removed in vacuo to give a residue, which was purified by flash column chromatography [hexanes/EtOAc/CH₂Cl₂ (5:1:1)] to give 43 (493 mg, 53%) as a yellow oil: $^1$H NMR (CDCl₃) δ 5.92 (1H, s), 3.73 (3H, s), 2.55 (1H, ddd, J=13.0 Hz, 4.9 Hz, 2.2 Hz), 2.42-2.26 (3H, m), 1.88 (1H, ddd, J=13.3 Hz, 13.3 Hz, 5.4 Hz), 1.70-1.61 (3H, m), 1.24 (3H, s), 1.15 (3H, m); $^1$H NMR (CDCl₃) δ 199.2, 178.5, 174.2, 122.6, 56.1, 52.5, 42.9, 39.0, 35.8, 34.5, 34.3, 29.9, 28.5; HRMS (ESI+) calcd for C₁₃H C₃+H, 223.1334, found 223.1323.

Methyl 3',3'-dimethyl-1,2',3',6',7',7a'-hexahydrospiro[[1,3]dioxolane-2,5'-indene]-7a'-carboxylate (44)

A mixture of 43 (270.8 mg, 1.218 mmol), PPTS (45 mg) and ethylene glycol (545 μL, 9.746 mmol) in anhydrous toluene (25 mL) was heated under reflux overnight using a Dean-Stark apparatus. After cooling down to rt and ethylene glycol was separated, the resultant mixture was consentrated in vacuo to give a residue. To the residue was added water (15 mL) and CH₂Cl₂-Et₂O (1:2, 40 mL). The organic layer was washed with brine, dried over MgSO₄, filtered and concentrated in vacuo to give a residue, which was purified by flash column chromatography [hexanes/EtOAc (5:1)] to afford 44 (177 mg, 55%) as a pale yellow oil: $^1$H NMR (300 MHz, CDCl₃) δ 5.37 (1H, s), 4.06-3.84 (4H, m), 3.69 (3H, s), 2.30-2.22 (2H, m), 1.89-1.83 (1H, m), 1.79-1.63 (2H, m), 1.59-1.44 (3H, m), 1.18 (3H, s), 1.11 (3H, s); $^{13}$C NMR (75 MHz, CDCl₃) δ 176.1, 158.1, 119.1, 107.0, 64.8, 64.3, 55.5, 52.1, 41.0, 39.1, 36.0, 33.4, 31.8, 30.8, 29.2; HRMS (ESI+) calcd for C₁₅H₂₂O₄+H, 267.1596, found 267.1586.

(3',3'-Dimethyl-1',2',3',6',7',7a'-hexahydrospiro[[1,3]dioxolane-2,5'-inden]-7a'-yl)methanol (45)

To a solution of 44 (177 mg, 0.67 mmol) in anhydrous Et₂O (20 mL) was added LAH (58 mg, 1.53 mmol) slowly in batches. The mixture was stirred at rt for 1 h. Subsequently, to the mixture were added water (0.21 mL), 40% aqueous NaOH solution (0.15 mL), and water (0.44 mL) sequentially. After stirring at rt for 1 h, the upper solution was decanted and then the resultant off-white gummy solid in the reaction flask was washed with Et₂O (25 mL×3). The combined organic layer was dried over MgSO₄, filtered and concentrated in vacuo to give a residue, which was purified by flash column chromatography [hexanes/EtOAc (3:1)] to afford 45 (154 mg, 97%) as a colorless oil: $^1$H NMR (300 MHz, CDCl₃) δ 5.33 (1H, s), 4.13-3.88 (4H, m), 3.51-3.47 (2H, m), 2.14-2.04 (1H, m), 2.01-1.93 (1H, m), 1.85-1.68 (2H, m), 1.60-1.53 (1H, m), 1.47-1.36 (1H, m), 1.32-1.18 (2H, m), 1.11 (6H, s); $^{13}$C NMR (100 MHz, CDCl₃) δ 161.3, 119.2, 107.1, 64.6, 64.2, 62.6, 48.7, 40.6, 38.4, 33.1, 31.3, 30.5, 30.4, 30.3; HRMS (ESI+) calcd for C₁₄H₂₂O₃+H, 239.1647, found 239.1636.

3',3'-Dimethyl-1',2',3',6',7',7a'-hexahydrospiro[[1,3]dioxolane-2,5'-indene]-7a'-carbaldehyde A solution of oxalyl chloride (36 μL, 0.405 mmol) in CH₂Cl₂ (8 mL) was stirred for 20 min at about −65° C. in an isopropanol-dry ice bath. To the solution was added a CH₂Cl₂ solution (2 mL) of DMSO (63 μL, 0.883 mmol) dropwise and then the mixture was stirred for 10 min. After a CH₂Cl₂ solution (2 mL) of 45 (154 mg, 0.65 mmol) was added dropwise to the mixture, the mixture was stirred for 20 min at −65° C. To the reaction mixture were added Et$_3$N (256 µL, 1.84 mmol) and water (5 mL) successively after removal of the cooling bath. After dilution with CH$_2$Cl$_2$-Et$_2$O (1:2, 25 mL), the organic layer was washed with 5% aqueous HCl solution (10 mL), water (20 mL), saturated aqueous NaHCO$_3$ solution (20 mL) and brine (10 mL), dried over MgSO$_4$, filtered and concentrated in vacuo to give the titled compound (crude, 139.5 mg) as a pale yellow oil: $^1$H NMR (CDCl$_3$) δ 9.63 (1H, s), 5.51 (1H, s), 4.05-3.95 (4H, m), 3.89-3.84 (1H, m), 2.17-2.12 (2H, m), 1.86-1.63 (4H, m), 1.58-1.46 (2H, m), 1.45-1.39 (2H, m), 1.12 (3H, s), 1.08 (3H, s). $^{13}$C NMR (CDCl$_3$) δ 202.7, 156.5, 120.5, 106.5, 64.8, 64.4, 59.4, 41.0, 38.7, 31.9, 30.9, 30.2, 30.0, 28.6; HRMS (ESI+) calcd for C$_{14}$H$_{20}$O$_3$+H, 237.1491, found 237.1480.

7a'-Ethynyl-3',3'-diamethyl-1',2',3',6',7',7a'-hexahydrospiro[[1,3]dioxolane-2,5'-indene] (46)

To a solution of 3',3'-dimethyl-1',2',3',6',7',7a'-hexahydrospiro[[1,3]dioxolane-2,5'-indene]-7a'-carbaldehyde (crude, 139.5 mg) and K$_2$CO$_3$ (178.3 mg, 1.29 mmol) in anhydrous MeOH (20 mL) was added Ohira reagent[3] (149 mg, 0.77 mmol) dropwise. The mixture was stirred at rt overnight. The reaction mixture was concentrated in vacuo to give a residue. To the residue were added water (20 mL) and CH$_2$Cl$_2$-Et$_2$O (1:2, 40 mL). The organic layer was washed with saturated NaHCO$_3$ solution (20 mL). The aqueous layer was extracted with CH$_2$Cl$_2$-Et$_2$O (1:2, 20 mL×3). The combined organic layer was dried over MgSO$_4$, filtered and concentrated in vacuo to give a residue, which was purified by flash column chromatography [hexanes/EtOAc (6:1)] to afford 46 (64 mg, 43% from 45) as an off white solid: $^1$H NMR (CDCl$_3$) δ 5.25 (1H, s), 4.07-3.90 (4H, m), 2.31 (1H, ddd, J=14.1 Hz, 14.1 Hz, 3.2 Hz), 2.13 (1H, s), 2.09-1.98 (3H, m), 1.92-1.87 (1H, m), 1.65-1.57 (2H, m), 1.51-1.42 (1H, m), 1.27 (3H, s), 1.09 (3H, s); $^{13}$C NMR (CDCl$_3$) δ 160.1, 117.4, 107.0, 87.9, 69.4, 64.7, 64.3, 42.9, 40.7, 39.2, 38.4, 34.9, 31.4, 31.3, 30.1; HRMS (ESI+) calcd for C$_{15}$H$_{20}$O$_2$+H, 233.1542, found 233.1527.

7a-Ethynyl-3,3-dimethyl-2,3,7,7a-tetrahydro-1H-inden-5(6H)-one

To a solution of 46 (63 mg, 0.27 mmol) in MeOH (25 mL) was added 10% aqueous HCl solution (5 mL). The reaction mixture was stirred at rt for 2 h. The mixture was carefully neutralized with Et$_3$N (7 mL). After most of the solvent was removed in vacuo, water (15 mL) and EtOAc (30 mL) were added. The aqueous phase was extracted with EtOAc (20 mL×3). The combined organic layer was washed with brine, dried over MgSO$_4$, filtered and concentrated in vacuo to give the titled compound (crude, 68 mg) as a pale yellow solid: $^1$H NMR (CDCl$_3$) δ 5.74 (1H, s), 2.84-2.75 (1H, m), 2.40-2.38 (1H, m), 2.35-2.26 (1H, m), 2.18 (1H, s), 2.18-2.11 (1H, m), 2.09-2.03 (1H, m), 1.85-1.77 (1H, m), 1.70-1.54 (2H, m), 1.28 (3H, s), 1.09 (3H, s); $^{13}$C NMR (CDCl$_3$) δ 199.5, 180.2, 120.7, 85.6, 70.5, 43.3, 42.4, 38.9, 38.1, 35.6, 34.4, 30.3, 29.2; HRMS (ESI+) calcd for C$_{13}$H$_{16}$O$_2$+H, 189.1279, found 189.1267.

7a-Ethynyl-6-(hydroxymethylene)-3,3-dimethyl-2,3,7,7a-tetrahydro-1H-inden-5(6H)-one (47)

To a stirred solution of 7a-ethynyl-3,3-dimethyl-2,3,7,7a-tetrahydro-1H-inden-5(6H)-one (47 mg) in THF (8 mL) were added ethyl formate (216 µL, 2.69 mmol) and NaH (60% dispersed in mineral oil, 32.3 mg, 0.807 mmol) sequentially. After heating under reflux for 3 h, the reaction mixture was cooled to rt and quenched with 15% aqueous NH$_4$Cl solution (3 mL). The mixture was diluted with CH$_2$Cl$_2$-Et$_2$O (1:2, 15 mL) and then water (10 mL) was added. The aqueous layer was extracted with CH$_2$Cl$_2$-Et$_2$O (1:2, 15 mL×3). The combined organic layer was washed with brine, dried over MgSO$_4$, filtered and concentrated in vacuo to give 47 (crude, 89 mg) as an orange oil: $^1$H NMR (CDCl$_3$) δ 13.9 (1H, brs), 7.45 (1H, s), 5.89 (1H, s), 2.67 (1H, d, J=13.8 Hz), 2.45 (1H, d, J=13.8 Hz), 2.27-2.19 (1H, m), 2.14 (1H, s), 2.00 (1H, s), 2.10-2.02 (1H, m), 1.26 (6H, s); HRMS (ESI+) calcd for C$_{14}$H$_{16}$O$_2$+H, 217.1229, found 217.1216.

4a-Ethynyl-7,7-dimethyl-4a,5,6,7-tetrahydro-4H-indeno[5,6-d]isoxazole (48)

To a stirred solution of 47 (crude, 89 mg) in ethanol (10 mL) was added a solution of hydroxylamine hydrochloride (150 mg, 2.15 mmol) in water (1 mL). The mixture was heated under reflux for 1.5 h. After cooling to rt, the solvent was removed in vacuo. To the resultant mixture were added EtOAc (30 mL) and water (15 mL). The aqueous layer was extracted with EtOAc (15 mL×3). The combined organic layer was washed with brine, dried over MgSO$_4$, filtered and concentrated in vacuo to give a residue, which was purified by flash column chromatography [hexanes/EtOAc (5:1)] to afford 48 (27 mg, 46% from 46) as yellow oil. $^1$H NMR (500 MHz, CDCl$_3$) δ 8.06 (1H, s), 6.30 (1H, s), 3.05 (1H, d, J=15.3 Hz), 2.62 (1H, d, J=15.3 Hz), 2.22-2.18 (1H, m), 2.12-2.06 (1H, m), 2.00 (1H, s), 1.82-1.75 (2H, m), 1.34 (3H, s), 1.17 (3H, s). $^{13}$C NMR (125 MHz, CDCl$_3$) δ 167.3, 164.3, 148.4, 108.6, 106.9, 87.1, 68.3, 44.7, 41.3, 40.0, 37.9, 31.8, 30.6, 30.1. HRMS (ESI+) calcd for C$_{14}$H$_{15}$NO+H, 214.1232, found 214.1222.

3a-Ethynyl-1,1-dimethyl-6-oxo-2,3,3a,4,5,6-hexahydro-1H-indene-5-carbonitrile A solution of 48 (27 mg) in anhydrous MeOH (15 mL) was added to NaOMe (108 mg, 2.00 mmol) which was placed in a flask. The mixture was stirred at rt for 5.5 h. The solvent was removed in vacuo and then the resultant residue was diluted with EtOAc (25 mL). The organic mixture was washed with 5% aqueous HCl solution (10 mL×2), saturated aqueous NaHCO$_3$ solution (10 mL×2) and brine (10 mL×2), dried over MgSO$_4$, filtered and concentrated in vacuo to give the titled compound (crude, 26 mg) as a yellow solid: $^1$H NMR (CDCl$_3$) δ 5.88 (1H, s), 4.09 (1H, dd, J=13.6 Hz, 4.2 Hz), 2.72 (1H, dd, J=12.5 Hz, 4.2 Hz), 2.36 (1H, s), 2.27-2.17 (2H, m), 2.15-2.09 (1H, m), 1.79-1.75 (1H, m), 1.70-1.64 (1H, m), 1.33 (3H, s), 1.15 (3H, s); t$^3$C NMR (CDCl$_3$) δ 188.3, 181.5, 119.2, 116.9, 82.9, 72.7, 43.1, 43.0, 39.6, 38.8, 37.7, 37.5, 30.3, 29.2; HRMS (ESI+) calcd for C$_{14}$H$_{15}$NO+H, 214.1232, found 214.1222.

3a-Ethynyl-1,1-dimethyl-6-oxo-2,3,3a,6-tetrahydro-1H-indene-5-carbonitrile (8)

To a solution of 3a-ethynyl-1,1-dimethyl-6-oxo-2,3,3a,4,5,6-hexahydro-1H-indene-5-carbonitrile (crude, 26 mg) in PhH was added DDQ (72 mg, 0.32 mmol). The mixture was heated under reflux for 4 h. (The reaction progress was monitored by LC-MS.) The reaction mixture was concentrated in vacuo to give a residue, which was purified by flash column chromatography [petroleum ether/Et$_2$O (2:1)] to give 13 (21.0 mg, 46% from 48) as a light yellow oil: $^1$H NMR (CDCl$_3$) δ 7.64 (1H, s), 6.18 (1H, s), 2.40 (1H, s), 2.37-2.29 (2H, m), 1.92-1.86 (1H, m), 1.78-1.70 (1H, m), 1.45 (3H, s), 1.19 (3H, s); $^{13}$C NMR (CDCl$_3$) δ 179.4, 176.9, 155.9, 120.5, 117.0, 113.8, 79.3, 73.3, 45.0, 41.8, 38.5, 35.1, 30.7, 29.8; HRMS (ESI+) calcd for C$_{14}$H$_{13}$NO+H, 212.1075, found 212.1066. Anal. Calcd for C$_{12}$H$_9$NO.1/6H$_2$O: C, 78.48; H, 6.27; N, 6.54. Found: C, 78.32; H, 6.63, N, 6.37.

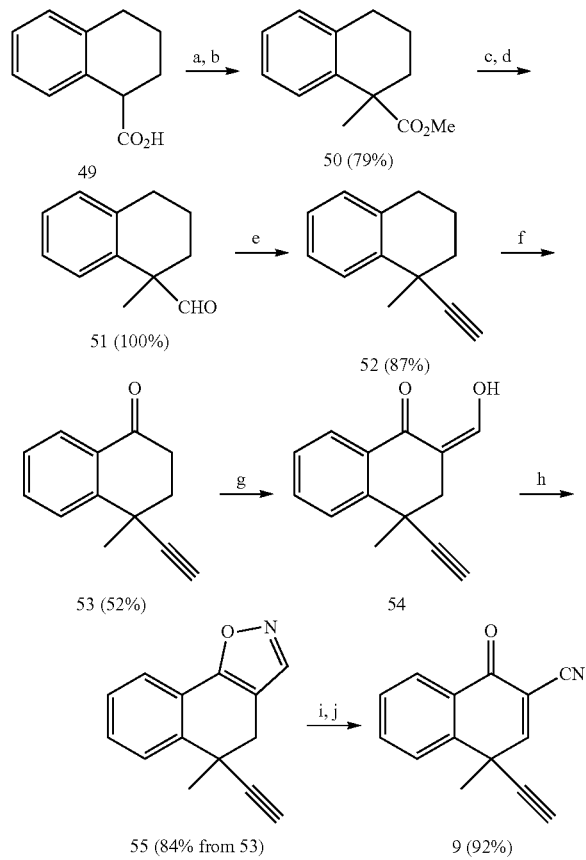

Scheme 6.$^a$ Synthesis of bicyclic ethynylcyanodienone 9

$^a$Reagents: (a) p-TsOH, MeOH; (b) MeLi, LDA, THF; (c) LAH, THF; (d) (COCl)$_2$, DMSO, CH$_2$Cl$_2$; (e) Ohira reagent, K$_2$CO$_3$, MeOH; (f) CrO$_3$, t-BuO$_2$H, CH$_2$Cl$_2$; (g) HCO$_2$Et, NaOMe, PhH; (h) NH$_2$OH•HCl, aqueous EtOH; (i) NaOMe, MeOH, Et$_2$O; (j) PhSeCl, pyridine, CH$_2$Cl$_2$; 30% aqueous H$_2$O$_2$, CH$_2$Cl$_2$.

Compound 49-50 was prepared similarly to the methods found in Noji, M. et al. 2008. Compound 51 was prepared similarly to the methods found in Taylor, S. K. et al. 1988.

1-Methyl-1,2,3,4-tetrahydronaphthalene-1-carbaldehyde (51)

To a solution of oxalyl chloride (206 μL, 2.4 mmol) in CH$_2$Cl$_2$ (24 mL) was added a solution of DMSO (342 μL, 4.8 mmol) in CH$_2$Cl$_2$ (6.4 mL) at −78° C. The mixture was stirred for 20 min at −78° C. To the reaction mixture was added a solution of (1-methyl-1,2,3,4-tetrahydronaphthalen-1-yl)methanol (346 mg, 1.96 mmol) in CH$_2$Cl$_2$ (19 mL) dropwise. and then stirred for 1 h at −78° C. After removal of the cooling bath, Et$_3$N (2 mL) and water (10 mL) were added successively. After dilution with CH$_2$Cl$_2$-Et$_2$O (1:2, 60 mL), the organic layer was washed with brine (15 mL×2), dried over MgSO$_4$, filtered and concentrated in vacuo to give 51 (crude, 340 mg), which was directly used for the next step without further purification (Nareddy, P. et al. 2012; Hulme, A. N. & Meyers, A. I. 1994).

1-Ethynyl-1-methyl-1,2,3,4-tetrahydronaphthalene (52)

To a solution of 51 (340 mg, 1.96 mmol) in anhydrous MeOH (50 mL) was added K$_2$CO$_3$ (829 mg, 6 mmol) and Ohira reagent$^3$ (422 mg, 2.2 mmol) at 0° C. The mixture was stirred at rt for 16 h. The reaction mixture was concentrated in vacuo to give a residue. To the residue were added water (10 mL) and CH$_2$Cl$_2$-Et$_2$O (1:2, 50 mL). The organic layer was washed with saturated NaHCO$_3$ solution (20 mL). The aqueous layer was extracted with CH$_2$Cl$_2$-Et$_2$O (1:2, 20 mL×3). The combined organic layer was dried over MgSO$_4$, filtered and concentrated in vacuo to give a residue, which was purified by flash column chromatography [petroleum ether/Et$_2$O (25:1)] to afford 52 (290 mg, 87%) as an oil: $^1$H NMR (CDCl$_3$) δ 7.57 (1H, d, J=7.6 Hz), 7.23 (1H, t, J=7.2 Hz), 7.15 (1H, dt, J=1.2 and 7.6 Hz), 7.08 (1H, d, J=7.6 Hz), 2.75-2.90 (2H, m), 2.24 (1H, s), 2.11-2.22 (1H, m), 1.95-2.06 (1H, m), 1.82-1.94 (2H, m), 1.63 (s, 3H); $^{13}$C NMR (CDCl$_3$) δ 141.1, 135.7, 129.5, 128.1, 126.7, 126.4, 92.7, 68.4, 38.5, 34.6, 31.5, 29.9, 19.7; HRMS (ESI+) calcd for C$_{13}$H$_{14}$+H, 171.1168, found 171.1165.

4-Ethynyl-4-methyl-3,4-dihydronaphthalen-1(2H)-one (53)

To a solution of 52 (34 mg, 0.2 mmol) in CH$_2$Cl$_2$ (1 mL) was added tert-butyl hydroperoxide (70% aqueous solution, 0.3 mL) and chromium trioxide (28 mg, 0.28 mmol) successively at 0° C. The mixture was stirred at rt for 3 h. After the reaction mixture was diluted with CH$_2$Cl$_2$-Et$_2$O (1:2, 20 mL), the resultant mixture was washed with 5% aqueous NaOH solution (10 mL×2). The aqueous layer was extracted with CH$_2$Cl$_2$-Et$_2$O (1:2, 10 mL×2). The combined organic layer was washed with 5% aqueous HCl solution (10 mL×2) and brine (10 mL×2), dried over MgSO$_4$, filtered and concentrated in vacuo to give a residue, which was purified by flash column chromatography [hexane/EtOAc (10:1)] to afford 53 (19 mg, 52%) as an oil: $^1$H NMR (CDCl$_3$) δ 8.04 (1H, d, J=7.6 Hz), 7.68 (1H, d, J=7.6 Hz), 7.58 (1H, t, J=7.2 Hz), 7.37 (1H, t, J=7.2 Hz), 2.93 (1H, ddd, J=4.8, 8.8 and 17.6 Hz), 2.75 (1H, ddd, J=4.8, 8 and 17.6 Hz), 2.38-2.50 (m, 1H), 2.32 (1H, s), 2.18-2.28 (1H, m), 1.70 (s, 3H); $^{13}$C NMR (CDCl$_3$) δ 197.2, 147.5, 134.3, 130.8, 127.7, 127.1, 89.1, 70.5, 36.6, 35.3, 34.7, 29.3; HRMS (ESI+) calcd for C$_{13}$H$_{12}$O+H, 185.0961, found 185.0973.

4-Ethynyl-2-(hydroxymethylene)-4-methyl-3,4-dihydronaphthalen-1(2H)-one (54)

To a stirred solution of 53 (37 mg, 0.20 mmol) in PhH (2 mL) were added NaOMe (54 mg, 1.0 mmol) and ethyl formate (77 μL, 0.96 mmol). After stirring at rt for 1 h, the reaction mixture was diluted with CH$_2$Cl$_2$-Et$_2$O (1:2, 20 mL). The mixture was washed with 5% aqueous HCl solution (5 mL×2) and brine (5 mL), dried over MgSO$_4$, filtered and concentrated in vacuo to give 54 as a yellow oil (crude, 38 mg). This material was used for the next reaction without further purification.

5-Ethynyl-5-methyl-4,5-dihydronaphtho[2,1-d]isoxazole (55)

To a stirred solution of 54 (crude, 38 mg) in EtOH (10 mL) was added a solution of hydroxylamine hydrochloride (139 mg, 2 mmol) in water (0.5 mL). The mixture was heated under reflux for 1 h. After cooling to rt, the mixture was treated with $CH_2Cl_2$-$Et_2O$ (1:2, 20 mL) and water (12 mL). The aqueous layer was extracted with $CH_2Cl_2$-$Et_2O$ (1:2, 10 mL×3). The combined organic layer was washed with brine (20 mL×3), dried over $MgSO_4$, filtered and concentrated in vacuo to give a residue, which was purified by flash column chromatography [hexanes/EtOAc (8:1)] to afford 55 (35 mg, 84% from 53) as a light yellow solid: $^1$H NMR (400 MHz, $CDCl_3$) δ 8.21 (1H, s), 7.80 (1H, d, J=7.6 Hz), 7.72 (1H, d, J=7.2 Hz), 7.36-7.48 (2H, m), 3.21 (1H, d, J=16 Hz), 2.94 (1H, d, J=16 Hz), 2.43 (1H, s), 1.49 (3H, s); $^{13}$C NMR (100 MHz, $CDCl_3$) δ 164.0, 149.5, 140.6, 130.6, 128.0, 127.1, 122.8, 122.6, 109.7, 88.8, 71.4, 37.1, 33.4, 29.9; HRMS (ESI+) calcd for $C_{14}H_{11}NO$+H, 210.0913, found 210.0916.

4-Ethynyl-4-methyl-1-oxo-1,4-dihydronaphthalene-2-carbonitrile (9)

To a solution of NaOMe (702 mg, 13.0 mmol) in anhydrous MeOH (9 mL) was added a solution of 55 (85 mg, 0.41 mmol) in $Et_2O$ (11 mL). The mixture was stirred at rt for 1 h. The reaction mixture was diluted with $CH_2Cl_2$-$Et_2O$ (1:2, 50 mL). The mixture was washed with 5% saturated aqueous HCl solution (15 mL×2), saturated aqueous $NaHCO_2$ solution (15 mL×2) and brine (15 mL×2), dried over $MgSO_4$, filtered and concentrated in vacuo to give 4-ethynyl-4-methyl-1-oxo-1,2,3,4-tetrahydronaphthalene-2-carbonitrile (crude, 90 mg) as a light yellow oil.

To a solution of PhSeCl (156 mg, 0.81 mmol) in anhydrous $CH_2Cl_2$ (9 mL) was added a solution of pyridine (71 mg, 0.9 mmol) in anhydrous $CH_2Cl_2$ (0.68 mL) at 0° C. The mixture was stirred at 0° C. for 15 min. Then to the mixture was added a solution of 4-ethynyl-4-methyl-1-oxo-1,2,3,4-tetrahydronaphthalene-2-carbonitrile (crude, 90 mg) in anhydrous $CH_2Cl_2$ (3.6 mL) at 0° C. After the mixture was stirred at 0° C. for 1 h, it was washed with 10% aqueous HCl solution (5 mL×2). At 0° C., 30% aqueous $H_2O_2$ solution was added 4 times at 10 min interval (total 0.4 mL). After the 4th addition of 30% aqueous $H_2O_2$ solution, the mixture was stirred at 0° C. for 20 min. The reaction mixture was washed with water (5 mL×2), saturated aqueous $NaHCO_3$ solution (10 mL) and brine (10 mL), dried over $MgSO_4$, filtered and concentrated in vacuo to give a residue, which was purified by flash column chromatography [hexanes/EtOAc (5:1)] to afford 9 (77 mg, 92% from 55) as a colorless solid: mp 164.0-165.5° C.; $^1$H NMR ($CDCl_3$) δ 8.20 (1H, dd, J=1.2 and 8 Hz), 7.79 (1H, dd, J=0.8 and 8 Hz), 7.72 (1H, dt, J=1.6 and 7.2 Hz), 7.70 (s, 1H), 7.52 (1H, dt, J=1.2 and 8 Hz), 2.47 (1H, s), 1.82 (3H, s); $^{13}$C NMR ($CDCl_3$) δ 177.9, 160.6, 144.3, 134.7, 128.8, 128.2, 128.1, 127.6, 115.7, 113.9, 82.7, 72.7, 37.3, 32.2; HRMS (ESI+) calcd for $C_{14}H_9NO$+H, 208.0757, found 208.0756. Anal. Calcd for $C_{14}H_9NO$: C, 81.14; H, 4.38; N, 6.76. Found: C, 81.03; H, 4.31; N, 6.72.

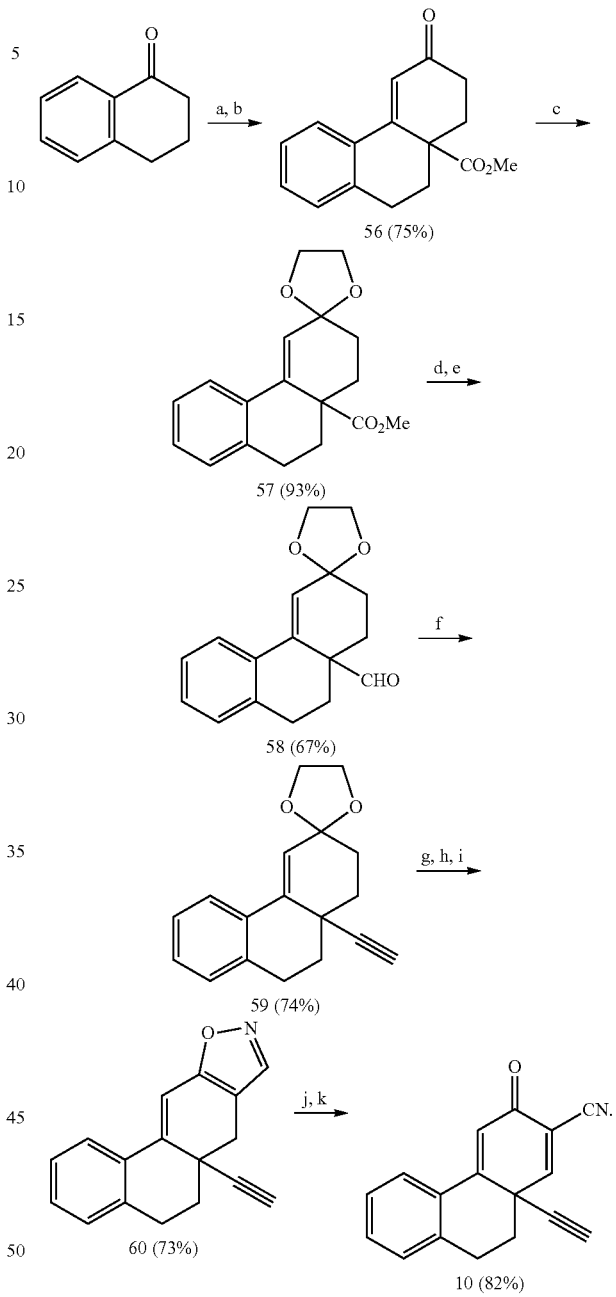

Scheme 7.[a] Synthesis of tricyclic ethynylcyanodienone 10

[a]Reagents: (a) NaH, $Me_2CO_3$; (b) methyl vinyl ketone, NaOMe, MeOH; (c) ethylene glycol, p-TsOH, toluene; (d) LAH, $Et_2O$; (e) $(COCl)_2$, DMSO, $CH_2Cl_2$; (f) Ohira reagent, $K_2CO_3$, MeOH; (g) 10% aqueous HCl, MeOH; (h) $HCO_2Et$, NaOMe, PhH; (i) $NH_2OH·HCl$, aqueous EtOH; (j) NaOMe, MeOH, $Et_2O$; (k) PhSeCl, pyridine, $CH_2Cl_2$; 30% aqueous $H_2O_2$, $CH_2Cl_2$.

Methyl 6-oxo-6,7,8,8a,9,10-hexahydrophenanthrene-8a-carboxylate (56)

To a suspension of NaH (60% in mineral oil, 4.40 g, 110 mmol) in dimethyl carbonate (20 mL) was added a solution of 1-tetralone (7.31 g, 50 mmol) in dimethyl carbonate (45 mL) at rt. The mixture was heated under reflux at 105° C. for 2 h. After cooling to rt, the reaction mixture was poured into ice water and extracted with EtOAc (200 mL×3). The combined extract was dried over MgSO$_4$, filtered and concentrated in vacuo to give a residue, which was purified through a silica gel plug eluting with hexane/EtOAc (15:1-12:1) and subsequent crystallization in hexanes/EtOAc to afford methyl 1-oxo-1,2,3,4-tetrahydronaphthalene-2-carboxylate (9.2 g, 90%) as pale yellow crystals. (Justribo, V. et al. 2007; Brown, D. et al. 1995): $^1$H NMR (300 MHz, CDCl$_3$) δ 8.05 (1H, d, J=7.8 Hz), 7.50 (1H, t, J=7.2 Hz), 7.35-7.24 (2H, m), 3.78 (3H, s), 3.04 (1H, dd, J=4.8 Hz, 10.2 Hz), 3.07-3.00 (2H, m), 2.53-2.46 (1H, m), 2.41-2.33 (1H, m); $^{13}$C NMR (100 MHz, CDCl$_3$) δ 193.1, 170.6, 143.6, 133.9, 131.7, 128.8, 127.7, 126.9, 54.4, 52.3, 27.6, 26.3.

To a solution of methyl 1-oxo-1,2,3,4-tetrahydronaphthalene-2-carboxylate (102 mg, 0.5 mmol) and NaOMe (81 mg, 1.5 mmol) in MeOH was added methyl vinyl ketone (52 μL, 0.625 mmol) dropwise at rt. The mixture was heated at 50° C. for 1 h and then was heated at 90° C. for 1 h. After cooling to rt, the solvent was removed in vacuo and the resultant residue was treated with CH$_2$Cl$_2$ (10 mL) and water (10 mL). The aqueous layer was extract with CH$_2$Cl$_2$ (10 mL×3). The combined organic layer was washed with brine (15 mL×3), dried over MgSO$_4$, filtered and concentrated in vacuo to give a residue, which was purified by flash column chromatography [hexanes/EtOAc (6:1-3:1)] to afford the titled compound 56 (106 mg, 83%) as a pale yellow solid: $^1$H NMR (CDCl$_3$) δ 7.78 (1H, d, J=8.0 Hz), 7.34 (1H, t, J=7.2 Hz), 7.26 (1H, t, J=7.2 Hz), 7.17 (1H, d, J=7.6 Hz), 3.66 (3H, s), 2.89 (2H, dd, J=3.2 Hz, 7.2 Hz), 2.54-2.39 (4H, m), 2.09 (1H, ddd, J=13.2 Hz, 13.2 Hz, 4.8 Hz), 1.87 (1H, ddd, J=13.0 Hz, 9.2 Hz, 9.2 Hz); $^{13}$C NMR (CDCl$_3$) δ 199.1, 173.7, 154.7, 138.3, 131.3, 130.6, 129.6, 126.8, 125.7, 122.2, 52.7, 47.8, 35.0, 34.7, 34.6, 27.1; HRMS (ESI+) calcd for C$_{16}$H$_{16}$O$_3$+H, 257.1178, found 257.1169.

Methyl 2',9',10',10a'-tetrahydro-1'H-spiro[[1,3]dioxolane-2,3'-phenanthrene]-10a'-carboxylate (57)

A mixture of 56 (129 mg, 0.5 mmol), ethylene glycol (195 μL, 3.5 mmol), and p-TsOH (19 mg) in anhydrous toluene (20 mL) was heated under reflux for 4 h using a Dean-Stark apparatus. After cooling down to rt, the solvent was removed in vacuo. To the resultant residue were added water (20 mL) and CH$_2$Cl$_2$-Et$_2$O (1:2, 20 mL). The organic layer was washed with saturated aqueous NaHCO$_3$ solution (5 mL×2) and brine (5 mL×2), dried over MgSO$_4$, filtered and concentrated in vacuo to give a residue, which was purified by flash column chromatography [hexanes/EtOAc (6:1)] to afford 57 (140 mg, 93%) as a pale yellow solid. $^1$H NMR (CDCl$_3$) δ 7.65-7.63 (1H, m), 7.17 (1H, t, J=3.6 Hz), 7.06-7.04 (1H, m), 6.14 (1H, s), 4.11-4.05 (3H, m), 3.96-3.91 (1H, m), 3.58 (3H, s), 2.81-2.79 (2H, m), 2.44-2.39 (1H, m), 2.31-2.27 (1H, m), 1.95-1.73 (4H, m); $^{13}$C NMR (CDCl$_3$) δ 175.2, 139.3, 135.9, 133.3, 129.0, 127.9, 126.1, 124.7, 121.7, 106.3, 65.0, 64.3, 52.2, 47.1, 34.5, 33.7, 30.7, 26.8; HRMS (ESI+) calcd for C$_{18}$H$_{10}$O$_4$+H, 301.1440, found 301.1438.

(2',9',10',10a'-Tetrahydro-1'H-spiro[[1,3]dioxolane-2,3'-phenanthren]-10a'-yl)methanol To a solution of 57 (402 mg, 1.34 mmol) in anhydrous Et$_2$O (45 mL) was added LAH (117 mg, 3.09 mmol) slowly in batches. After the mixture was stirred at rt for 1 h, to the reaction mixture were added water (0.3 mL), 40% aqueous NaOH solution (0.21 mL), and water (0.6 mL) sequentially. The mixture was stirred at rt for 1 h. After the upper solution was decanted, the off-white gummy solid in the reaction flask was washed with Et$_2$O (40 mL×3). The combined organic layer was dried over MgSO$_4$, filtered and concentrated in vacuo to give a residue, which was purified by flash column chromatography [hexanes/EtOAc (3:1)] to afford the titled compound (264 mg, 72%) as a colorless solid: $^1$H NMR (CDCl$_3$) δ 7.53 (1H, dd, J=7.8 Hz, 1.2 Hz), 7.20-7.07 (3H, m), 6.04 (1H, d, J=1.2 Hz), 4.09-4.03 (3H, m), 3.97-3.92 (1H, m), 3.55 (1H, d, J=11.2 Hz), 3.44 (1H, d, J=11.2 Hz), 2.97-2.76 (2H, m), 2.15-2.07 (2H, m), 2.05-1.96 (1H, m), 1.92 (1H, brs), 1.86-1.80 (1H, m), 1.63-1.53 (2H, m); $^{13}$C NMR (100 MHz, CDCl$_3$) δ 142.1, 136.4, 133.1, 129.0, 127.9, 125.9, 125.0, 122.2, 106.4, 64.8, 64.3, 61.8, 38.3, 31.5, 29.7, 29.4, 25.7; HRMS (ESI+) calcd for C$_{17}$H$_{10}$O$_3$+H, 273.1491, found 273.1490.

2',9',10',10a'-Tetrahydro-1'H-spiro[[1,3]dioxolane-2,3'-phenanthrene]-10a'-carbaldehyde (58)

A solution of oxalyl chloride (92 μL, 1.09 mmol) in CH$_2$Cl$_2$ (6 mL) was stirred for 20 min at about −65° C. in an isopropanol-dry ice bath. To the stirred solution was added a solution of DMSO (169 μL, 2.37 mmol) in CH$_2$Cl$_2$ (2 mL) dropwise. After the mixture was stirred for 10 min, to the mixture was added a solution (2 mL) of (2',9',10',10a'-tetrahydro-1'H-spiro[[1,3]dioxolane-2,3'-phenanthren]-10a'-yl)methanol (269 mg, 0.99 mmol) in CH$_2$Cl$_2$ (2 mL) dropwise. Then, the mixture was stirred for 20 min at −65° C. After removal of the cooling bath, to the mixture were added Et$_3$N (700 μL) and water (8 mL). After dilution with CH$_2$Cl$_2$-Et$_2$O (1:2, 40 mL), the organic layer was washed with 5% aqueous HCl solution (10 mL), water (10 mL), saturated aqueous NaHCO$_3$ solution (10 mL) and brine (10 mL), dried over MgSO$_4$, filtered and concentrated in vacuo to give a residue, which was purified by flash column chromatography [hexanes/EtOAc (4:1→3:1)] to afford 58 (141 mg, 93%) as a colorless foamy solid: $^1$H NMR (CDCl$_3$) δ 7.65-7.63 (1H, m), 7.17 (1H, t, J=3.6 Hz), 7.06-7.04 (1H, m), 6.14 (1H, s), 4.11-4.05 (3H, m), 3.96-3.91 (1H, m), 3.58 (3H, s), 2.81-2.79 (2H, m), 2.44-2.39 (1H, m), 2.31-2.27 (1H, m), 1.95-1.73 (4H, m); $^{13}$C NMR (CDCl$_3$) δ 175.2, 139.3, 135.9, 133.3, 129.0, 127.9, 126.1, 124.7, 121.7, 106.3, 65.0, 64.3, 52.2, 47.1, 34.5, 33.7, 30.7, 26.8; HRMS (ESI+) calcd for C$_{17}$H$_{10}$O$_3$+H, 271.1334, found 271.1332.

10a'-Ethynyl-2',9',10',10a'-tetrahydro-1'H-spiro[[1,3]dioxolane-2,3'-phenanthrene] (59)

To a stirred solution of 58 (0.89 g, 3.28 mmol) and K$_2$CO$_3$ (0.91 g, 6.56 mmol) in anhydrous MeOH (50 mL) was added Ohira reagent[3] (0.76 g, 3.94 mmol) dropwise. After the stirring was continued at rt for 3 h, the reaction mixture was concentrated in vacuo. The resultant mixture was treated with water (20 mL) and CH$_2$Cl$_2$-Et$_2$O (1:2, 40 mL). The organic layer was washed with saturated aqueous NaHCO$_3$ solution (40 mL). The aqueous layer was extracted with CH$_2$Cl$_2$-Et$_2$O (1:2, 50 mL×3). The combined organic layer was dried over MgSO$_4$, filtered and concentrated in vacuo to give a residue, which was purified by flash column chromatography [hexanes/EtOAc (6:1)] to afford 59 (0.64 g, 74%) as a pale yellow solid: $^1$H NMR (CDCl$_3$) δ 7.62 (1H, d, J=8.0 Hz), 7.24-7.13 (3H, m), 6.05 (1H, s), 4.12-4.05 (3H, m), 3.99-3.93 (1H, m), 3.34 (1H, ddd, J=17.6 Hz, 12.8 Hz, 4.8 Hz), 2.83 (1H, dd, J=16.8 Hz, 3.6 Hz), 2.34 (1H, ddd, J=13.7 Hz, 13.7 Hz, 3.0 Hz), 2.13-2.00 (2H, m), 1.98 (1H, s), 1.97-1.80 (2H, m), 1.76 (1H, ddd, J=13.0 Hz, 13.0 Hz, 5.0 Hz); $^{13}$C NMR (CDCl$_3$) δ 140.6, 136.7, 131.9, 129.1, 128.2, 126.0, 125.1, 120.2, 106.4, 86.0, 69.4, 65.0, 64.4, 36.2, 35.7, 35.2, 30.6, 26.8; HRMS (ESI+) calcd for $C_{18}H_{18}O_2$+H, 267.1385, found 267.1378.

10a-Ethynyl-1,9,10,10a-tetrahydrophenanthren-3(2H)-one

To a solution of 59 (110 mg, 0.42 mmol) in MeOH (30 mL) was added 10% aqueous HCl solution (8 mL). The mixture was stirred at rt for 10 min. The mixture was carefully neutralized with $Et_3N$ (5 mL). After most of the solvent was removed in vacuo, the resultant mixture was treated with water (25 mL) and EtOAc (40 mL). The aqueous phase was extracted with EtOAc (25 mL×3). The combined organic layer was washed with brine (30 mL×2), dried over $MgSO_4$, filtered and concentrated in vacuo to give the titled compound (crude, 100 mg) as a colorless solid: $^1$H NMR (300 MHz, $CDCl_3$) δ 7.73 (1H, d, J=8.4 Hz), 7.35 (1H, t, J=7.5), 7.22 (2H, d, J=8.1 Hz), 6.57 (1H, s), 3.43 (1H, ddd, J=17.1 Hz, 12.9 Hz, 4.5 Hz), 3.04-2.86 (2H, m), 2.53 (1H, ddd, J=17.1 Hz, 3.0 Hz, 3.0 Hz), 2.29 (1H, ddd, J=13.2 Hz, 4.8 Hz, 2.4 Hz), 2.15 (1H, ddd, J=12.9 Hz, 4.8 Hz, 2.1 Hz), 2.13 (1H, s), 2.05 (1H, ddd, J=14.7 Hz, 13.2 Hz, 3.9 Hz), 1.87 (1H, ddd, J=13.2 Hz, 13.2 Hz, 4.8 Hz); $^{13}$C NMR (75 MHz, $CDCl_3$) δ 199.7, 156.0, 139.2, 131.2, 130.2, 130.0, 127.0, 126.3, 120.7, 83.8, 71.2, 36.9, 36.3, 36.0, 35.0, 23.3; HRMS (ESI+) calcd for $C_{16}H_{14}O$+H, 223.1123, found 223.1121. This material was used for the next step without further purification.

10a-Ethynyl-2-(hydroxymethylene)-1,9,10,10a-tetrahydrophenanthren-3(2H)-one

To a stirred solution of crude 10a-ethynyl-1,9,10,10a-tetrahydrophenanthren-3(2H)-one (100 mg) in PhH (3 mL) were added ethyl formate (196 µL, 2.36 mmol) and NaOMe (130.1 mg, 2.36 mmol) sequentially. After stirring at rt for 1 h, 5% aqueous HCl solution (5 mL) was added slowly to acidify the reaction mixture. The mixture was treated with $CH_2Cl_2$-$Et_2O$ (1:2, 15 mL) and water (10 mL). The aqueous layer was extracted with $CH_2Cl_2$-$Et_2O$ (1:2, 15 mL×3). The combined organic layer was washed with brine (25 mL×2), dried over $MgSO_4$, filtered and concentrated in vacuo to give the titled compound as a bright yellow solid (crude, 110 mg): $^1$H NMR ($CDCl_3$) δ 14.0 (1H, brs), 7.83 (1H, d, J=8.0 Hz), 7.76 (1H, s), 7.35 (1H, t, J=6.0 Hz), 7.26 (2H, dt, J=11.4 Hz, 8.0 Hz), 6.73 (1H, s), 3.40 (1H, ddd, J=17.2 Hz, 13.1 Hz, 4.2 Hz), 2.89 (1H, ddd, J=16.8 Hz, 4.0 Hz, 2.4 Hz), 2.68 (2H, s), 2.20 (1H, ddd, J=12.8 Hz, 4.4 Hz, 2.4 Hz), 2.08 (1H, s), 1.86 (1H, ddd, J=13.1 Hz, 13.1 Hz, 4.4 Hz); $^{13}$C NMR ($CDCl_3$) δ 187.2, 168.6, 152.4, 139.1, 130.6, 129.6, 129.2, 126.6, 125.5, 119.0, 106.2, 84.1, 70.5, 37.6, 36.4, 35.0, 27.0; HRMS (ESI+) calcd for $C_{17}H_{11}O_2$+H, 251.1072, found 251.1068. This material was used for the next step without further purification.

6a-Ethynyl-5,6,6a,7,7a,10a-hexahydrophenanthro[2,3-d]isoxazole (60)

To a stirred solution of 10a-ethynyl-2-(hydroxymethylene)-1,9,10,10a-tetrahydrophenanthren-3(2H)-one (110 mg) in EtOH (7 mL) was added a solution of hydroxylamine hydrochloride (483 mg, 6.95 mmol) in water (1.2 mL). The mixture was heated under reflux for 1 h. After cooling to rt, the solvent was removed in vacuo. The resultant mixture was treated with EtOAc (30 mL) and water (20 mL). The aqueous layer was extracted with EtOAc (15 mL×3). The combined organic layer was washed with brine (25 mL×2), dried over $MgSO_4$, filtered and concentrated in vacuo to give a residue, which was purified by flash column chromatography [hexanes/EtOAc (4:1)] to afford 60 (75 mg, 73% from 59) as a pale yellow solid: $^1$H NMR (300 MHz, $CDCl_3$) δ 8.16 (1H, s), 7.84-7.81 (1H, m), 7.29-7.19 (4H, s), 3.47-3.36 (1H, m), 3.13 (1H, d, J=15.6 Hz), 2.91-2.81 (2H, m), 2.28-2.21 (1H, m, J=16.8 Hz, 3.6 Hz), 1.95 (1H, s), 1.93 (1H, ddd, J=12.9 Hz, 12.9 Hz, 5.1 Hz); $^{13}$C NMR ($CDCl_3$) δ 166.2, 148.1, 141.0, 137.6, 130.5, 129.5, 129.0, 126.6, 124.3, 109.2, 107.1, 85.8, 68.8, 37.7, 35.3, 33.8, 28.5; HRMS (ESI+) calcd for $C_{17}H_{13}NO$+H, 248.1075, found 248.1060.

10a-Ethynyl-3-oxo-1,2,3,9,10,10a-hexahydrophenanthrene-2-carbonitrile

To a solution of NaOMe (263.2 mg, 4.77 mmol) in anhydrous MeOH (12 mL) was added a solution of 60 (74 mg, 0.30 mmol) in $Et_2O$ (3 mL). The mixture was stirred at rt for 2 h. The solvent was removed in vacuo. The resultant residue was diluted with EtOAc (30 mL) and washed with 5% aqueous HCl solution (10 mL×2), saturated aqueous $NaHCO_3$ solution (10 mL×2) and brine (10 mL×2). The organic layer was dried over $MgSO_4$, filtered and concentrated in vacuo to give the titled compound (crude, 78 mg) as a pale yellow solid: $^1$H NMR (300 MHz, $CDCl_3$) δ 7.72 (1H, d, J=8.1 Hz), 7.44 (1H, t, J=7.2 Hz), 7.32-7.25 (2H, m), 6.64 (1H, m), 4.22 (1H, dd, J=14.7 Hz, 4.2 Hz), 3.44 (1H, ddd, J=14.7 Hz, 13.2 Hz, 4.2 Hz), 2.96 (1H, ddd, J=15.2 Hz, 4.8 Hz, 2.4 Hz), 2.68 (1H, dd, J=12.9 Hz, 4.2 Hz), 2.41 (1H, t, J=13.2 Hz), 2.25 (1H, s), 2.21 (1H, dd, J=5.1 Hz, 2.1 Hz), 1.90 (1H, ddd, J=12.9 Hz, 4.8 Hz); HRMS (ESI+) calcd for $C_{17}H_{13}NO$+H, 248.1075, found 248.1070. This material was used for the next step without further purification.

10a-Ethynyl-3-oxo-3,9,10,10a-tetrahydrophenanthrene-2-carbonitrile (10)

To a solution of PhSeCl (121 mg, 0.63 mmol) in anhydrous $CH_2Cl_2$ (6 mL) was added a solution of pyridine (59 µL, 0.69 mmol) in anhydrous $CH_2Cl_2$ (1 mL) at 0° C. The mixture was stirred at 0° C. for 20 min. Then, to the mixture was added a solution of 10a-ethynyl-3-oxo-1,2,3,9,10,10a-hexahydrophenanthrene-2-carbonitrile (78 mg) in anhydrous $CH_2Cl_2$ (3 mL) at 0° C. The reaction mixture was stirred at 0° C. for 1 h. The mixture was washed with 10% aqueous HCl solution (2 mL×2). At 0° C., 30% aqueous $H_2O_2$ solution (25 µL) was added 5 times at 10 min interval. After the 5$^{th}$ addition, the mixture was stirred at 0° C. for additional 20 min. The reaction mixture was diluted with $CH_2Cl_2$-$Et_2O$ (1:2, 40 mL). The resultant mixture was washed with water (5 mL×2), saturated aqueous $NaHCO_3$ solution (10 mL) and brine (10 mL), dried over $MgSO_4$, filtered and concentrated in vacuo to give a residue, which was purified by flash column chromatography [hexanes/EtOAc (4:1)] to afford 10 (60 mg, 82% from 60) as an off-white solid: mp 209.5-211.0° C.; $^1$H NMR ($CDCl_3$) δ 7.64 (1H, d, J=7.8 Hz), 7.53 (1H, s), 7.44 (1H, t, J=7.8 Hz), 7.33 (1H, t, J=7.6 Hz), 7.28 (1H, d, J=6.0 Hz), 6.71 (1H, s), 3.54 (1H, ddd, J=16.0 Hz, 12.3 Hz, 5.6 Hz), 3.09 (1H, dd, J=17.5 Hz, 5.3 Hz), 2.42 (1H, ddd, J=12.8 Hz, 5.8 Hz, 1.2 Hz), 2.25 (1H, s), 1.98 (1H, ddd, J=12.6 Hz, 12.6 Hz, 5.6 Hz); $^{13}$C NMR ($CDCl_3$) δ 178.7, 158.1 156.0, 136.9, 131.5, 130.9, 129.2, 127.2, 126.0, 120.4, 116.6, 113.5, 77.4, 73.6, 38.3, 34.0, 26.0; HRMS (ESI+) calcd for $C_{17}H_{11}NO$+H, 246.0919, found 246.0911. Anal. Calcd for $C_{17}H_{11}NO.1/3H_2O$: C, 81.26; H, 4.68; N, 5.57. Found: C, 81.08; H, 4.87, N, 5.34.

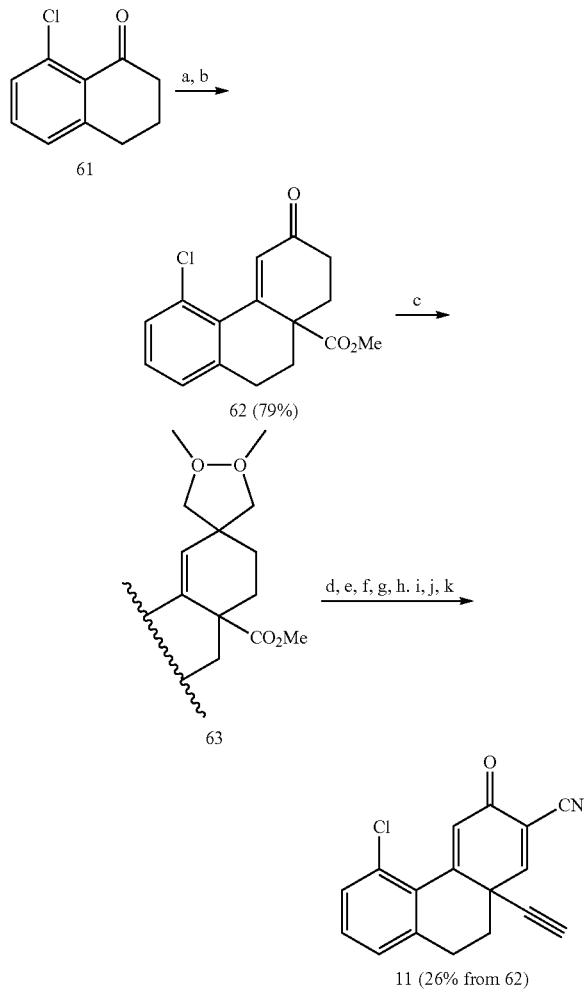

Scheme 8A (X = Cl).[a] Synthesis of chlorotricyclic ethynylcyanodienone

[a]Reagents: (a) NaH, Me$_2$CO$_3$; (b) methyl vinyl ketone, NaOMe, MeOH; (c) 2,3-butanediol, p-TsOH, toluene; (d) LAH, Et$_2$O; (e) (COCl)$_2$, DMSO, CH$_2$Cl$_2$; (f) Ohira reagent, K$_2$CO$_3$, MeOH; (g) 10% aqueous HCl, MeOH; (h) HCO$_2$Et, NaOMe, PhH; (i) NH$_2$OH•HCl, aqueous EtOH; (j) NaOMe, MeOH, Et$_2$O; (k) PhSeCl, pyridine, CH$_2$Cl$_2$; 30% aqueous H$_2$O$_2$, CH$_2$Cl$_2$.

Methyl 8-chloro-1-hydroxy-3,4-dihydronaphthalene-2-carboxylate

To a suspension of NaH (60% in mineral oil, 558 mg, 13.7 mmol) in dimethyl carbonate (30 mL) was added a solution of 8-chloro-1-tetralone (61) (0.84 g, 4.65 mmol) in dimethyl carbonate (10 mL) at rt. The mixture was heated under reflux for 2 h. After cooling to rt, the reaction mixture was poured into ice water and extracted with EtOAc (30 mL×3). The combined organic layer was dried over MgSO$_4$, filtered and concentrated in vacuo to give a residue, which was purified by flash column chromatography [hexanes/EtOAc (5:1)] to afford the titled compound (1.02 g, 92%) as a yellow solid (Nguyen, P. et al. 2003): $^1$H NMR (CDCl$_3$, The compound was observed as a mixture of keto and enol isomers); Enol isomer: δ 13.0 (1H, s), 7.33-7.31 (1H, m), 7.21 (1H, t, J=8.0 Hz), 7.12-7.10 (1H, m), 3.85 (3H, s), 2.77 (2H, t, J=6.6 Hz), 2.50 (1H, t, J=7.6 Hz); $^{13}$C NMR (CDCl$_3$) δ 172.9, 165.4, 145.9, 132.4, 130.5, 130.4, 127.3, 126.0, 99.1, 51.7, 29.3, 20.2; HRMS (ESI+) calcd for $C_{12}H_{11}ClO_3$+H, 239.0475, found 239.0455.

Methyl 4-chloro-6-oxo-6,7,8,8a,9,10-hexahydrophenanthrene-8a-carboxylate (62)

To a stirred solution of methyl 8-chloro-1-hydroxy-3,4-dihydronaphthalene-2-carboxylate (119 mg, 0.5 mmol) and NaOMe (81 mg, 1.5 mmol) in MeOH (12 mL) was added methyl vinyl ketone (52 μL, 0.63 mmol) dropwise at rt. The mixture was heated at 50° C. for 1 h and then was heated at 90° C. for 1 h. After cooling to rt, the solvent was removed in vacuo and then the resultant residue was treated with CH$_2$Cl$_2$ (25 mL) and water (10 mL). The aqueous layer was extract with CH$_2$Cl$_2$ (10 mL×3). The combined organic layer was washed with brine (25 mL×2), dried over MgSO$_4$, filtered and concentrated in vacuo to give a residue, which was purified by flash column chromatography [hexanes/EtOAc/CH$_2$Cl$_2$ (4:1:1)] to afford 62 (125 mg, 86%) as a pale yellow solid: $^1$H NMR (CDCl$_3$) δ 7.34 (1H, d, J=8.0 Hz), 7.19 (1H, t, J=7.8 Hz), 7.07 (1H, d, J=7.6 Hz), 6.49 (1H, s), 3.62 (3H, s), 2.79-2.73 (1H, m), 2.66-2.49 (4H, m), 2.25-2.16 (1H, m), 2.10-2.03 (1H, m), 1.99-1.94 (1H, m); $^{13}$C NMR (CDCl$_3$) δ 198.3, 174.0, 152.3, 142.0, 133.9, 131.8, 129.5, 129.3, 129.0, 125.4, 52.6, 47.8, 35.1, 34.5, 33.1, 27.6; HRMS (ESI+) calcd for $C_{16}H_{15}ClO_3$+H, 291.0788, found 291.0785.

Methyl 5'-chloro-4,5-dimethyl-2',9',10',10a'-tetrahydro-1'H-spiro [[1,3]dioxolane-2,3'-phenanthrene]-10a'-carboxylate (63)

A mixture of 62 (126 mg, 0.43 mmol), 2,3-butanediol (316 μL, 3.46 mmol), and PPTS (11 mg) in anhydrous toluene (12 mL) was heated under reflux for 1 h using a Dean-Stark apparatus. After cooling down to rt, the solvent was removed in vacuo and then the resultant residue was treated with water (10 mL) and CH$_2$Cl$_2$-Et$_2$O (1:2, 30 mL). The organic layer was washed with saturated NaHCO$_3$ solution (10 mL) and brine (10 mL), dried over MgSO$_4$, filtered and concentrated in vacuo to give 63 (152 mg) as a pale yellow solid: HRMS (ESI+) calcd for $C_{20}H_{23}ClO_4$+H, 363.1363, found 363.1358. This material was used for the next step without further purification.

(5'-Chloro-4,5-dimethyl-2',9',10',10a'-tetrahydro-1'H-spiro[[1,3]dioxolane-2,3'-phenanthren]-10a'-yl)methanol To a stirred solution of 63 (crude, 152 mg) in anhydrous Et$_2$O (20 mL) was added LAH (37 mg, 0.97 mmol) slowly in batches. The mixture was stirred at rt for 1 h. To the reaction mixture were added water (0.15 mL), 40% aqueous NaOH solution (0.1 mL), and water (0.3 mL) sequentially. The mixture was stirred at rt for 1 h. After the upper solution was decanted, the off-white gummy solid in the reaction flask was washed with Et$_2$O (20 mL×3). The combined organic solution was dried over MgSO$_4$, filtered and concentrated in vacuo to give the titled compound (crude, 146 mg) as a pale yellow oily solid: HRMS (ESI+) calcd for $C_{19}H_{23}ClO_3$+H, 335.1414, found 335.1410. This material was used for the next step without further purification. 5'-Chloro-4,5-dimethyl-2',9',10',10a'-tetrahydro-1'H-spiro[[1,3]dioxolane-2,3'-phenanthrene]-10a'-carbaldehyde. A solution of oxalyl chloride (41 μL, 0.47 mmol) in $CH_2Cl_2$ (6 mL) was stirred at about −65° C. in an isopropanol-dry ice bath for 20 min. To the stirred solution was added a solution of DMSO (62 μL, 0.86 mmol) in $CH_2Cl_2$ (2 mL) dropwise and then the mixture was stirred for 10 min. To the the mixture was added a solution of (5'-chloro-4,5-dimethyl-2', 9',10',10a'-tetrahydrospiro[[1,3]dioxolane-2,3'-phenanthren]-10a'-yl)methanol (crude, 146 mg) in $CH_2Cl_2$ (2 mL) dropwise and then the mixture was stirred at −65° C. for 20 min. To the reaction mixture were added $Et_3N$ (300 μL) and water (4 mL) successively after removal of the cooling bath. After dilution with $CH_2Cl_2$-$Et_2O$ (1:2, 40 mL), the organic layer was washed with of 5% aqueous HCl solution (5 mL×2), water (5 mL×2), 5 mL of saturated aqueous $NaHCO_3$ solution (5 mL×2) and brine (5 mL×2), dried over $MgSO_4$, filtered and concentrated in vacuo to give the titled compound (crude, 146 mg) as a pale yellow oil. HRMS (ESI+) calcd for $C_{19}H_{21}ClO_3$+H, 333.1257, found 333.1254. This material was used for the next step without further purification.

5'-Chloro-10a'-ethynyl-4,5-dimethyl-2',9',10',10a'-tetrahydro-1'H-spiro[[1,3]dioxolane-2,3'-phenanthrene]

To a solution of 5'-chloro-4,5-dimethyl-2',9',10',10a'-tetrahydro-1'H-spiro[[1,3]dioxolane-2,3'-phenanthrene]-10a'-carbaldehyde (crude, 146 mg) and $K_2CO_3$ (119 mg, 0.86 mmol) in anhydrous MeOH (25 mL) was added Ohira reagent[16] (100 mg, 0.52 mmol) dropwise. After stirring at rt for 3 h, the reaction mixture was concentrated in vacuo to remove the solvent. The resultant residue was treated with water (15 mL) and $CH_2Cl_2$-$Et_2O$ (1:2, 30 mL). The organic layer was washed with saturated aqueous $NaHCO_3$ solution (10 mL). The aqueous layer was extracted with $CH_2Cl_2$-$Et_2O$ (1:2, 15 mL×3). The combined organic layer was dried over $MgSO_4$, filtered and concentrated in vacuo to give the titled compound (crude, 147 mg) as a pale yellow solid. HRMS (ESI+) calcd for $C_{20}H_{21}ClO_2$+H, 323.1308, found 329.1306. This material was used for the next step without further purification.

5-Chloro-10a-ethynyl-1,9,10,10a-tetrahydrophenanthren-3 (2H)-one

To a solution of 5'-chloro-10a'-ethynyl-4,5-dimethyl-2',9', 10',10a'-tetrahydro-1'H-spiro[[1,3]dioxolane-2,3'-phenanthrene] (crude, 147 mg) in MeOH (30 mL) was added 10% aqueous HCl solution (3 mL). The mixture was stirred at rt for 1 h. The reaction mixture was carefully neutralized with $Et_3N$ (3 mL). After most of the solvent was removed in vacuo, the resultant residue was treated with water (15 mL) and EtOAc (30 mL). The aqueous phase was extracted with EtOAc (10 mL×3). The combined organic layer was washed with brine (20 mL×2), dried over $MgSO_4$, filtered and concentrated in vacuo to give a residue (100 mg), which was purified by flash column chromatography [hexanes/EtOAc (5:1)] to afford the titled compound (68.0 mg, 61% from 62) as a colorless solid: $^1$H NMR ($CDCl_3$) δ 7.34 (1H, d, J=7.8 Hz), 7.21 (1H, t, J=7.8 Hz), 7.11 (1H, d, J=7.4 Hz), 6.63 (1H, s), 3.62 (3H, s), 3.04-2.93 (2H, m), 2.68-2.61 (1H, m), 2.57-2.51 (1H, m), 2.33-2.28 (1H, m), 2.12 (1H, s), 2.20-2.07 (3H, m); $^{13}$C NMR ($CDCl_3$) δ 198.7, 153.0, 142.3, 132.9, 131.7, 130.0, 129.3, 128.0, 126.2, 84.9, 70.5, 37.3, 35.8, 35.7, 34.9, 27.8; HRMS (ESI+) calcd for $C_{16}H_{13}ClO$+H, 257.0733, found 257.0729.

5-Chloro-10a-ethynyl-2-(hydroxymethylene)-1,9,10, 10a-tetrahydrophenanthren-3(2H)-one To a stirred solution of 5-chloro-10a-ethynyl-1,9,10,10a-tetrahydrophenanthren-3(2H)-one (68 mg, 0.27 mmol) in PhH (3 mL) were sequentially added ethyl formate (118 μL, 1.46 mmol) and NaOMe (79 mg, 1.46 mmol). After stirring at rt for 1 h, 5% aqueous HCl solution (3 mL) was added slowly to acidify the reaction mixture. The reaction mixture was treated with $CH_2Cl_2$-$Et_2O$ (1:2, 20 mL) and water (10 mL). The aqueous layer was extracted with $CH_2Cl_2$-$Et_2O$ (1:2, 10 mL×3). The combined organic layer was washed with brine (20 mL×2), dried over $MgSO_4$, filtered and concentrated in vacuo to give the titled compound as a bright yellow solid (77 mg): $^1$H NMR ($CDCl_3$) δ 7.88 (1H, s), 7.35 (1H, d, J=8.0 Hz), 7.21 (1H, t, J=7.7 Hz), 7.11 (1H, d, J=8.0 Hz), 6.80 (1H, s), 2.91-2.84 (2H, m), 2.67-2.55 (2H, m), 2.12 (1H, s), 2.10-2.06 (1H, m), 2.00-1.94 (1H, m); $^{13}$C NMR ($CDCl_3$) δ 185.8, 171.1, 149.7, 142.6, 132.6, 131.6, 129.8, 129.4, 126.7, 125.9, 106.1, 86.2, 70.1, 36.2, 35.9, 35.7, 28.2; HRMS (ESI+) calcd for $C_{17}H_{13}ClO_2$+H, 285.0682, found 285.0681. This material was used for the next step without further purification.

1-Chloro-6a-ethynyl-5,6,6a,7-tetrahydrophenanthro [2,3-d]isoxazole

To a stirred solution of 5-chloro-10a-ethynyl-2-(hydroxymethylene)-1,9,10,10a-tetrahydrophenanthren-3(2H)-one (77 mg) in EtOH (8 mL) was added a solution of hydroxylamine hydrochloride (147 mg, 2.12 mmol) in water (1.5 mL). The mixture was heated under reflux for 1 h. After cooling to rt, the solvent was removed in vacuo and the resultant residue was treated with EtOAc (30 mL) and water (15 mL). The aqueous layer was extracted with EtOAc (10 mL×3). The combined organic layer was washed with brine (20 mL×2), dried over $MgSO_4$, filtered and concentrated in vacuo to give a residue, which was purified by flash column chromatography [hexanes/EtOAc (6:1)] to afford the titled compound (39 mg, 52% over two steps) as a yellow solid: $^1$H NMR ($CDCl_3$) δ 8.18 (1H, s), 7.37 (1H, d, J=8.0 Hz), 7.35 (1H, s), 7.17 (1H, t, J=7.6 Hz), 7.11 (1H, d, J=7.5 Hz), 3.07-2.97 (2H, m), 2.91 (1H, ddd, J=15.2 Hz, 4.8 Hz, 4.8 Hz), 2.63 (1H, ddd, J=15.0 Hz, 11.2 Hz, 4.0 Hz), 2.13 (1H, ddd, J=13.4 Hz, 4.6 Hz, 4.6 Hz), 1.99 (1H, s), 2.00-1.93 (1H, m); $^{13}$C NMR ($CDCl_3$) δ 165.5, 148.2, 141.7, 138.0, 132.3, 132.0, 129.3, 128.7, 125.9, 115.1, 109.3, 87.6, 68.3, 37.0, 36.7, 32.1, 28.6; HRMS (ESI+) calcd for $C_{17}H_{12}ClO$+H, 282.0686, found 282.0682.

5-Chloro-10a-ethynyl-3-oxo-1,2,3,9,10,10a-hexahydrophenanthrene-2-carbonitrile

To a solution of NaOMe (119 mg, 2.21 mmol) in anhydrous MeOH (12 mL) was added a solution of 1-chloro-6a-ethynyl-5,6,6a,7-tetrahydrophenanthro[2,3-d]isoxazole (39 mg, 0.14 mmol) in anhydrous $Et_2O$ (1 mL). The mixture was stirred at rt for 1 h. After the solvent was removed in vacuo, the resultant residue was diluted with EtOAc (30 mL). The organic solution was washed with 5% aqueous HCl solution (10 mL×2), saturated aqueous $NaHCO_3$ solution (10 mL×2) and brine (10 mL×2), dried over $MgSO_4$, filtered and concentrated in vacuo to give the titled compound (crude, 43 mg) as a pale yellow solid: $^1$H NMR ($CDCl_3$) δ 7.37 (1H, d, J=8.0 Hz), 7.27 (1H, t, J=7.7 Hz), 7.14 (1H, d, J=7.6 Hz), 6.79 (1H, s), 4.21 (1H, dd, J=14.0 Hz, 4.0 Hz), 3.10-3.02 (1H, m), 2.76-2.67 (2H, m), 2.43 (1H, t, J=14.0 Hz), 2.28

(1H, s), 2.22-2.15 (1H, m), 2.11-2.04 (1H, m); $^{13}$C NMR (CDCl$_3$) δ 187.7, 153.8, 142.1, 133.4, 130.9, 130.2, 129.8, 126.8, 125.9, 116.3, 82.5, 72.6, 39.3, 37.7, 36.8, 36.0, 27.5; HRMS (ESI+) calcd for C$_{17}$H$_{12}$ClNO+H, 282.0686, found 282.0680. This material was used for the next step without further purification.

5-Chloro-10a-ethynyl-3-oxo-3,9,10,10a-tetrahydro-phenanthrene-2-carbonitrile (11)

To a solution of PhSeCl (53 mg, 0.28 mmol) in anhydrous CH$_2$Cl$_2$ (3 mL) was added a solution of pyridine (53 μL, 0.66 mmol) in anhydrous CH$_2$Cl$_2$ (1 mL) at 0° C. The mixture was stirred at 0° C. for 20 min. Then, to the stirred solution was added a solution of 5-chloro-10a-ethynyl-3-oxo-1,2,3,9,10,10a-hexahydrophenanthrene-2-carbonitrile (43 mg) in anhydrous CH$_2$Cl$_2$ (3 mL) at 0° C. After the mixture was stirred at 0° C. for 1 h, it was washed with 10% aqueous HCl solution (1 mL×2). At 0° C., 30% aqueous H$_2$O$_2$ solution (15 μL) was added 5 times at 10 min interval. After the 5th addition, the mixture was stirred at 0° C. for additional 20 min. The reaction mixture was washed with water (5 mL×2), saturated aqueous NaHCO$_3$ solution (10 mL) and brine (10 mL). The organic layer was dried over MgSO$_4$, filtered and concentrated in vacuo to give a residue, which was purified by flash column chromatography [hexanes/EtOAc (5:1)] to afford 11 (32 mg, 82% over two steps, 261 from 62) as an off-white solid: mp>230° C.; $^1$H NMR (CDCl$_3$) δ 7.58 (1H, s), 7.35 (1H, d, J=7.8 Hz), 7.25 (1H, t, J=7.8 Hz), 7.13 (1H, d, J=7.6 Hz), 7.09 (1H, s), 3.42 (1H, ddd, J=18.0, 11.6, 8.2), 3.11 (1H, dd, J=17.6 Hz, 6.4 Hz), 2.46 (1H, dd, J=12.8 Hz, 5.6 Hz), 2.22 (1H, s), 1.91 (1H, ddd, J=12.2 Hz, 12.2 Hz, 6.4 Hz); $^{13}$C NMR (CDCl$_3$) δ 178.3, 158.8, 152.5, 139.1, 133.0, 130.6, 129.8, 129.7, 127.5, 126.2, 116.2, 113.3, 74.0, 38.9, 35.6, 26.3; HRMS (ESI+) calcd for C$_{17}$H$_{10}$ClNO+H, 280.0529, found 280.0523. Anal. Calcd for C$_{17}$H$_{10}$CLNO.1/6CH$_2$Cl$_2$: C, 70.16; H, 3.54; Cl, 16.09; N, 4.77. Found: C, 70.01; H, 3.68; Cl, 15.92; N, 4.65.

Scheme 8B (X = Br).$^a$ Synthesis of bromotricyclic ethynylcyanodienone

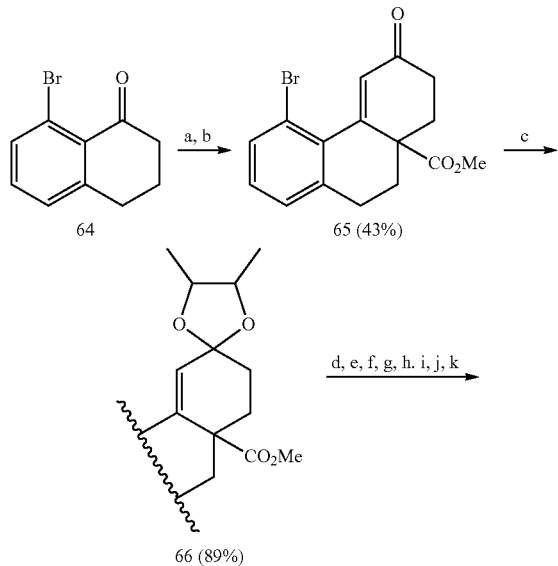

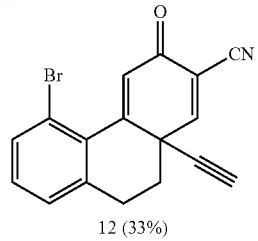

12 (33%)

$^a$Reagents: (a) NaH, Me$_2$CO$_3$; (b) methyl vinyl ketone, NaOMe, MeOH; (c) 2,3-butanediol, PPTS, toluene; (d) LAH, Et$_2$O; (e) (COCl)$_2$, DMSO, CH$_2$Cl$_2$; (f) Ohira reagent, K$_2$CO$_3$, MeOH; (g) 10% aqueous HCl, MeOH; (h) HCO$_2$Et, NaOMe, PhH; (i) NH$_2$OH·HCl, aqueous EtOH; (j) NaOMe, MeOH, Et$_2$O; (k) PhSeCl, pyridine, CH$_2$Cl$_2$; 30% aqueous H$_2$O$_2$, CH$_2$Cl$_2$.

Methyl 8-bromo-1-hydroxy-3,4-dihydronaphthalene-2-carboxylate

To a suspension of NaH (60% in mineral oil, 398.1 mg, 9.952 mmol) in dimethyl carbonate (20 mL) was added a solution of 8-bromo-1-tetralone (64)$^{11}$ (747 mg, 3.32 mmol) in dimethyl carbonate (20 mL) at rt. The mixture was heated under reflux for 1 h. After cooling to rt, the reaction mixture was poured into ice water and extracted with EtOAc (200 mL×3). The combined extract was dried over MgSO$_4$, filtered and concentrated in vacuo to give a residue, which was purified by flash column chromatography [hexanes/EtOAc (8:1→3:1)] to afford the titled compound (536 mg, 57%) as a pale yellow solid: $^1$H NMR (CDCl$_3$. The compound was observed as a mixture of keto and enol isomers.) Enol isomer, δ 13.0 (s, 1H), 7.55 (d, J=7.6 Hz, 1H), 7.16-7.08 (m, 2H), 3.84 (s, 3H), 2.75 (t, J=7.0 Hz, 2H), 2.48 (t, J=7.2 Hz, 2H); $^{13}$C NMR (CDCl$_3$) δ 173.0, 165.3, 143.5, 134.1, 134.0, 130.7, 126.7, 120.0, 99.2, 51.8, 29.5, 20.2; HRMS (ESI+) calcd for C$_{12}$H$_{11}$BrO$_3$+H, 282.9970, found 282.9964.

Methyl 4-bromo-6-oxo-6,7,8,8a,9,10-hexahydrophenanthrene-8a-carboxylate (65)

To a stirred mixture of methyl 8-bromo-1-hydroxy-3,4-dihydronaphthalene-2-carboxylate (536 mg, 1.89 mmol) and NaOMe (307 mg, 5.68 mmol) in MeOH (20 mL) was added methyl vinyl ketone (0.20 mL, 2.37 mmol) dropwise at rt. The mixture was heated at 50° C. for 30 min and then was heated at 90° C. for 1.5 h. After cooling to rt, the solvent was removed in vacuo and the resultant residue was treated with CH$_2$Cl$_2$ (15 mL) and water (15 mL). The aqueous layer was extract with CH$_2$Cl$_2$ (15 mL×3). The combined organic layer was washed with brine (25 mL×2) and dried over MgSO$_4$, filtered and concentrated in vacuo to give a residue, which was purified by flash column chromatography [hexanes/EtOAc/CH$_2$Cl$_2$ (5:1:1)] to afford 65 (483 mg, 76%) as a pale yellow solid: $^1$H NMR (CDCl$_3$) δ 7.54 (t, J=4.4 Hz, 1H), 7.12 (d, J=4.4 Hz, 2H), 6.46 (s, 1H), 3.65 (s, 3H), 2.75 (d, J=14.8 Hz, 1H), 2.67-2.48 (m, 4H), 2.24-2.17 (m, 1H), 2.09 (d, J=13.2 Hz, 1H), 1.94 (ddd, J=13.0 Hz, 1H); $^{13}$C NMR (CDCl$_3$) δ 198.3, 174.1, 153.8, 142.3, 136.0, 132.4, 129.8, 129.4, 125.9, 121.2, 52.6, 47.8, 35.3, 34.6, 33.1, 27.9; HRMS (ESI+) calcd for C$_{16}$H$_{15}$BrO$_3$+H, 335.0283, found 335.0266.

Methyl 5'-bromo-4,5-dimethyl-2',9',10',10a'-tetrahydro-1'H-spiro[[1,3]dioxolane-2,3'-phenanthrene]-10a'-carboxylate (66)

A mixture of 65 (96 mg, 0.29 mmol), 2,3-butane-diol (207 μL, 2.29 mmol) and PPTS (9.8 mg) in anhydrous toluene (30 mL) was heated under reflux for 3 h using a Dean-Stark apparatus. After cooling down to rt, the solvent was removed in vacuo. The resultant residue was dissolved in $CH_2Cl_2$-$Et_2O$ (1:2, 3 mL) and filtered through a silica gel plug. Then the organic solution was concentrated in vacuo to give a residue, which was purified by flash column chromatography [hexanes/EtOAc (5:1)] to afford 66 (a mixture of diasteromers, 104 mg, 89%) as a pale yellow solid: $^1$H NMR ($CDCl_3$) δ 7.48 (d, J=7.2 Hz, 1H), 7.02-6.98 (m, 2H), 6.09 (s, 1H), 3.78-3.73 (m, 1H), 3.61-3.55 (m, 1H), 2.71-2.57 (m, 2H), 2.35-2.30 (m, 1H), 2.04-1.87 (m, 5H), 1.34-1.24 (m, 6H); HRMS (ESI+) calcd for $C_{20}H_{23}BrO_4$+H, 407.0858, found 407.0848.

(5'-Bromo-4,5-dimethyl-2',9',10',10a'-tetrahydro-1'H-spiro [[1,3]dioxolane-2,3'-phenanthren]-10a'-yl)methanol To a stirred solution of 66 (104 mg, 0.26 mmol) in anhydrous $Et_2O$ (10 mL) was added LAH (22 mg, 0.59 mmol) slowly in batches. The mixture was stirred at rt for 1 h. To the reaction mixture were added water (60 µL), 40% aqueous NaOH solution (45 µL), and water (120 µL) sequentially. After stirring at rt for 1 h, the upper solution was decanted. The resultant off-white gummy solid in the reaction flask was washed with $Et_2O$ (20 mL×3). The combined organic layer was dried over $MgSO_4$, filtered and concentrated in vacuo to give the titled compound (crude, 95 mg) as a yellow waxy solid: HRMS (ESI+) calcd for $C_{19}H_{23}BrO_3$+H, 379.0909, found 379.0882. This material was used for the next step without further purification.

5'-Bromo-4,5-dimethyl-2',9',10',10a'-tetrahydro-1'H-spiro [[1,3]dioxolane-2,3'-phenanthrene]-10a'-carbaldehyde A solution of oxalyl chloride (24 µL, 0.27 mmol) in $CH_2Cl_2$ (3 mL) was stirred at about −65° C. in an isopropanol-dry ice bath for 20 min. To the stirred solution was added a solution of DMSO (24 µL, 0.60 mmol) in $CH_2Cl_2$ (1 mL) was added dropwise and then the mixture was stirred for 10 min. To the mixture was added a solution of (5'-bromo-4,5-dimethyl-2',9',10',10a'-tetrahydro-1'H-spiro[[1,3]dioxolane-2,3'-phenanthren]-10a'-yl)methanol (crude, 95 mg) in $CH_2Cl_2$ (1 mL) dropwise and then the mixture was stirred for 20 min at −65° C. To the reaction mixture were added $Et_3N$ (174 µL) and water (4 mL) after removal of the cooling bath. After dilution with $CH_2Cl_2$-$Et_2O$ (1:2, 30 mL), the organic layer was washed with 5% aqueous HCl solution (10 mL), water (10 mL), saturated aqueous $NaHCO_3$ solution (10 mL) and brine (10 mL), dried over $MgSO_4$, filtered and concentrated in vacuo to give the titled compound (96 mg) as a yellow foamy solid: HRMS (ESI+) calcd for $C_{19}H_{21}BrO_3$+H, 377.0752, found 377.0720. This material was used for the next step without further purification.

5'-Bromo-10a'-ethynyl-4,5-dimethyl-2',9',10',10a'-tetrahydro-1'H-spiro[[1,3]dioxolane-2,3'-phenanthrene]

To a solution of 5'-bromo-4,5-dimethyl-2',9',10',10a'-tetrahydro-1'H-spiro[[1,3]dioxolane-2,3'-phenanthrene]-10a'-carbaldehyde (96.3 mg) and $K_2CO_3$ (70.6 mg, 0.511 mmol) in anhydrous MeOH (10 mL) was added Ohira reagent[16] (59 mg, 0.31 mmol) dropwise. The mixture was stirred at rt overnight. The reaction mixture was concentrated in vacuo to remove solvent. The resultant residue was treated with water (15 mL) and $CH_2Cl_2$-$Et_2O$ (1:2, 20 mL). The organic layer was washed with saturated aqueous $NaHCO_3$ solution (10 mL). The aqueous layer was extracted with $CH_2Cl_2$-$Et_2O$ (1:2, 15 mL×3). The combined organic layer was dried over $MgSO_4$, filtered and concentrated in vacuo to give the titled compound (crude, 98 mg) as a pale yellow solid: HRMS (ESI+) calcd for $C_{20}H_{21}BrO_2$+H, 373.0803, found 377.0771. This material was used for the next step without further purification.

5-Bromo-10a-ethynyl-1,9,10,10a-tetrahydrophenanthren-3(2H)-one

To a solution of 5'-bromo-10a'-ethynyl-4,5-dimethyl-2',9',10',10a'-tetrahydro-1'H-spiro[[1,3]dioxolane-2,3'-phenanthrene] (98 mg) in 4eOH (30 mL) was added 10% aqueous HCl solution (8 mL). The mixture was stirred at rt for 20 min. The reaction mixture was carefully neutralized with $Et_3N$ (5 mL). After most of the solvent was removed in vacuo, the resultant residue was treated with water (25 mL) and EtOAc (40 mL). The aqueous phase was extracted with EtOAc (25 mL×3). The combined organic layer was washed with brine (30 mL×2), dried over $MgSO_4$, filtered and concentrated in vacuo to give a residue, which was purified by flash column chromatography [hexanes/EtOAc (4:1)] to afford the titled compound (65 mg, 84% from 66) as a colorless solid: $^1$H NMR ($CDCl_3$) δ 7.56 (t, J=4.4 Hz, 1H), 7.15-7.14 (m, 2H), 6.52 (s, 1H), 3.02 (ddd, J=18.0 Hz, 14.0 Hz, 15.0 Hz, 1H), 2.85 (ddd, J=15.2 Hz, 4.8 Hz, 4.8 Hz, 1H), 2.60-2.54 (m, 2H), 2.31-2.27 (m, 1H), 2.23-2.16 (m, 2H), 2.14-2.03 (m, 2H); $^{13}$C NMR ($CDCl_3$) δ 198.6, 154.6, 142.7, 134.3, 132.6, 130.1, 12.2, 126.4, 121.9, 85.2, 70.5, 37.5, 35.8, 35.2, 28.0; HRMS (ESI+) calcd for $C_{16}H_{13}BrO$+H, 301.0228, found 301.0225.

5-Bromo-10a-ethynyl-2-(hydroxymethylene)-1,9,10,10a-tetrahydrophenanthren-3(2H)-one To a solution of 5-bromo-10a-ethynyl-1,9,10,10a-tetrahydrophenanthren-3(2H)-one (70 mg, 0.23 mmol) in PhH (3 mL) were added ethyl formate (103 µL, 1.28 mmol) and NaOMe (69 mg, 1.28 mmol) sequentially. After stirring at rt for 1.5 h, 5% aqueous HCl solution (5 mL) was added slowly to acidify the reaction mixture. The mixture was treated with $CH_2Cl_2$-$Et_2O$ (1:2, 15 mL) and water (10 mL). The aqueous layer was extracted with $CH_2Cl_2$-$Et_2O$ (1:2, 15 mL×3). The combined organic layer was washed with brine (20 mL×2), dried over $MgSO_4$, filtered and concentrated in vacuo to give the titled compound (crude, 87 mg) as a yellow oil: $^1$H NMR ($CDCl_3$) δ 13.90 (brs, 1H), 7.85 (s, 1H), 7.57 (dd, J=11.0 Hz, 1.8 Hz, 1H), 7.36 (s, 1H), 7.17-7.12 (m, 2H), 6.69 (s, 1H), 2.89-2.78 (m, 2H), 2.67-2.53 (m, 2H), 2.14 (s, 1H), 2.12-2.05 (m, 1H), 1.95 (ddd, J=12.9 Hz, 12.9 Hz, 3.8 Hz, 1H); $^{13}$C NMR ($CDCl_3$) δ 186.0, 170.6, 151.2, 142.8, 134.0, 132.6, 130.1, 128.3, 126.8, 126.2, 121.7, 106.1, 86.2, 70.2, 36.2, 36.0, 35.6, 28.4; HRMS (ESI+) calcd for $C_{17}H_{13}BrO$+H, 329.0177, found 329.0168. This material was used for the next step without further purification.

1-Bromo-6a-ethynyl-5,6,6a,7-tetrahydrophenanthro[2,3-d]isoxazole

To a stirred solution of 5-bromo-10a-ethynyl-2-(hydroxymethylene)-1,9,10,10a-tetrahydrophenanthren-3(2H)-one (87 mg) in EtOH (10 mL) was added a solution of hydroxylamine hydrochloride (129.0 mg, 1.856 mmol) in water (1 mL). The mixture was heated under reflux for 1 h.

After cooling to rt, the solvent was removed in vacuo and the resultant residue was treated with EtOAc (20 mL) and water (15 mL). The aqueous layer was extracted with EtOAc (15 mL×3). The combined organic layer was washed with brine (20 mL×2), dried over MgSO$_4$, filtered and concentrated in vacuo to give a residue, which was purified by flash column chromatography [hexanes/EtOAc (6:1)] to afford the titled compound (44 mg, 58% over two steps) as a pale yellow solid: $^1$H NMR (CDCl$_3$) δ 8.18 (s, 1H), 7.58 (d, J=7.8 Hz, 1H), 7.25 (s, 1H), 7.17-7.08 (m, 2H), 3.03 (d, J=4.6 Hz, 2H), 2.85 (ddd, J=15.1 Hz, 4.3 Hz, 4.3 Hz, 1H), 2.62 (ddd, J=15.2 Hz, 11.7 Hz, 3.7 Hz, 1H), 2.15 (ddd, J=13.2 Hz, 4.4 Hz, 4.4 Hz, 1H), 2.01 (s, 1H), 1.93 (ddd, J=12.6 Hz, 12.6 Hz, 4.0 Hz, 1H); $^{13}$C NMR (CDCl$_3$) δ 165.2, 148.3, 141.9, 139.4, 134.6, 132.6, 129.1, 126.3, 121.3, 115.1, 109.1, 87.5, 68.5, 37.0, 36.7, 31.9, 28.7; HRMS (ESI+) calcd for C$_{17}$H$_{12}$BrNO+H, 326.0181, found 326.0177.

5-Bromo-10a-ethynyl-3-oxo-1,2,3,9,10,10a-hexahydrophenanthrene-2-carbonitrile

To a solution of NaOMe (226 mg, 4.19 mmol) in anhydrous MeOH (10 mL) was added a solution of 1-bromo-6a-ethynyl-5,6,6a,7-tetrahydrophenanthro[2,3-d]isoxazole (85 mg, 0.26 mmol) in anhydrous MeOH (15 mL) and Et$_2$O (3 mL). The mixture was stirred at rt for 40 min. After the solvent was removed in vacuo, the resultant residue was treated with EtOAc (30 mL). The organic layer was washed with 5% aqueous HCl solution (10 mL×2), saturated aqueous NaHCO$_3$ solution (10 mL×2) and brine (10 mL×2), dried over MgSO$_4$, filtered and concentrated in vacuo to give the titled compound (crude, 86 mg) as a yellow solid: $^1$H NMR (CDCl$_3$) δ 7.59-7.55 (m, 1H), 7.21-7.15 (m, 2H), 6.64 (s, 1H), 4.24 (dd, J=13.8 Hz, 4.1 Hz, 1H), 2.94 (ddd, J=15.7 Hz, 5.2 Hz, 5.2 Hz, 1H), 2.69-2.58 (m, 2H), 2.47 (dd, J=13.4 Hz, 13.4 Hz, 1H), 2.31 (s, 1H), 2.15-2.09 (m, 1H); $^{13}$C NMR (CDCl$_3$) δ 187.4, 155.3, 142.4, 132.9, 132.7, 131.0, 126.8, 125.9, 122.1, 116.2, 82.8, 72.5, 39.2, 37.9, 36.8, 35.8, 23.6, 23.6; HRMS (ESI+) calcd for C$_{17}$H$_{12}$BrNO+H, 326.0181, found 326.0175. This material was used for the next step without further purification.

5-Bromo-10a-ethynyl-3-oxo-3,9,10,10a-tetrahydrophenanthrene-2-carbonitrile (12)

To a solution of PhSeCl (86 mg, 0.26 mmol) in anhydrous CH$_2$Cl$_2$ (5 mL) was added a solution of pyridine (50 μL, 0.58 mmol) in anhydrous CH$_2$Cl$_2$ (1 mL) at 0° C. After the mixture was stirred at 0° C. for 20 min, to the mixture was added a solution of 5-bromo-10a-ethynyl-3-oxo-1,2,3,9,10,10a-hexahydrophenanthrene-2-carbonitrile (0.26 mmol) in anhydrous CH$_2$Cl$_2$ (1 mL) at 0° C. The rmixture was stirred at 0° C. for 1 h. The reaction mixture was washed with 10% aqueous HCl solution (2 mL×2). At 0° C., 30% aqueous H$_2$O$_3$ solution (60 μL) was added 5 times at 10 min interval. After the 5$^{th}$ addition, the mixture was stirred at 0° C. for additional 20 min. The mixture was washed with water (5 mL×2), saturated aqueous NaHCO$_3$ solution (10 mL×2) and brine (10 mL×2), dried over MgSO$_4$, filtered and concentrated in vacuo to give a residue, which was purified by flash column chromatography [hexanes/EtOAc (4:1→3:1)] to afford 12 (57 mg, 67% over two steps, 33% from 66) as an off-white solid: mp 202-205° C.; $^1$H NMR (CDCl$_3$) δ 7.62 (s, 1H), 7.59 (t, J=4.6 Hz, 1H), 7.19 (d, J=5.2 Hz, 1H), 7.09 (s, 1H), 3.43 (ddd, J=18.0 Hz, 11.4 Hz, 6.6 Hz, 1H), 3.14 (dd, J=17.8 Hz, 6.1 Hz, 1H), 2.50 (dd, J=12.9 Hz, 6.9 Hz, 1H), 2.26 (s, 1H), 1.94 (ddd, J=11.9 Hz, 11.9 Hz, 6.7 Hz, 1H); $^{13}$C NMR (CDCl$_3$) δ 178.1, 158.8, 154.1, 139.3, 133.2, 131.6, 130.9, 128.1, 126.3, 121.9, 116.2, 113.3, 77.3, 74.1, 38.9, 36.1, 26.4; HRMS (ESI+) calcd for C$_{17}$H$_{10}$BrNO+H, 324.0024, found 324.0018. Anal. Calcd for C$_{17}$H$_{10}$BrNO: C, 62.99; H, 3.11; Br, 24.65; N, 4.32. Found: C, 63.33; H, 3.40, Br, 23.97, N, 4.18.

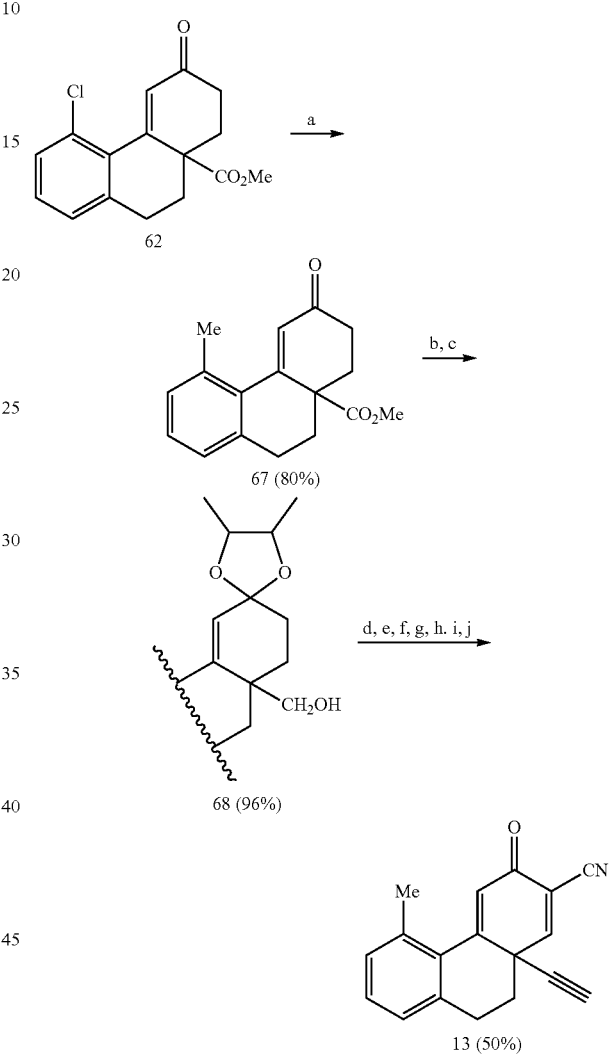

Scheme 9.$^a$ Synthesis of methyltricyclic ethynylcyanodienone 13

$^a$Reagents: (a) Pd(OAc)$_2$, RuPhos, MeB(OH)$_2$, K$_3$PO$_4$, toluene; (b) 2,3-butanediol, PPTS, toluene; (c) LAH, Et$_2$O; (d) (COCl)$_2$, DMSO, CH$_2$Cl$_2$; (e) Ohira reagent, K$_2$CO$_3$, MeOH; (f) 10% aqueous HCl, MeOH; (g) HCO$_2$Et, NaOMe, PhH; (h) NH$_2$OH•HCl, aqueous EtOH; (i) NaOMe, MeOH; (j) PhSeCl, pyridine, CH$_2$Cl$_2$; 30% aqueous H$_2$O$_2$, CH$_2$Cl$_2$.

Methyl 4-methyl-6-oxo-6,7,8,8a,9,10-hexahydrophenanthrene-8a-carboxylate (67)

A stirred mixture of 62 (231 mg, 0.80 mmol), MeB(OH)$_2$ (95 mg, 1.59 mmol), palladium acetate (4.2 mg, 3 mol %), RuPhos (2-Dicyclohexylphosphino-2',6'-diisopropoxybiphenyl, 22 mg, 6 mol %), K$_3$PO$_4$ (338 mg, 1.59 mmol) in toluene (8 mL) was heated at 100° C. for 47 h. After cooling to rt, the reaction mixture was treated with 15% aqueous NH$_4$Cl solution (10 mL) to quench the reaction. EtOAc (25 ml) was added to dilute the mixture and the aqueous layer was extracted with EtOAc (10 mL×3). The combined organic layer was washed with brine (20 mL×2), dried over MgSO$_4$, filtered and concentrated in vacuo to give a residue, which was purified by flash column chromatography [hexanes/EtOAc/CH$_2$Cl$_2$ (8:1:1)] to afford 67 (172 mg, 0.64 mmol, 80%) as a colorless solid: $^1$H NMR (CDCl$_3$) δ 7.22-7.16 (m, 2H), 7.01 (d, J=6.2, 1H), 6.12 (s, 1H), 3.64 (s, 3H), 2.72 (ddd, J=14.8 Hz, 4.0 Hz, 4.0 Hz, 1H), 2.57-2.49 (m, 4H), 2.48 (s, 3H), 2.31-2.22 (m, 1H), 2.09 (ddd, J=13.4 Hz, 4.0 Hz, 4.0 Hz, 1H), 1.96 (ddd, J=17.2 Hz, 4.0 Hz, 4.0 Hz, 1H); NMR (CDCl$_3$) δ 198.6, 174.5, 155.9, 140.4, 135.5, 135.4, 129.6, 128.7, 128.3, 124.3, 52.5, 48.5, 35.3, 34.6, 33.4, 27.7, 20.0; HRMS (ESI+) calcd for C$_{17}$H$_{18}$O$_3$+H, 271.1334, found 271.1329.

Methyl 4,5,5'-trimethyl-2',9',10',10a'-tetrahydro-1'H-spiro[[1,3]dioxolane-2,3'-phenanthrene]-10a'-carboxylate A mixture of 67 (172 mg, 0.64 mmol), 2,3-butanediol (581 μL, 6.36 mmol), and PPTS (16 mg) in anhydrous toluene (25 mL) was heated under reflux for 2.5 h. using a Dean-Stark apparatus. After cooling down to rt, the solvent was removed in vacuo and the resultant residue was treated with water (20 mL) and CH$_2$Cl$_2$-Et$_2$O (1:2, 40 mL). The organic layer was washed with saturated aqueous NaHCO$_3$ solution (15 mL×2) and brine (15 mL×2), dried over MgSO$_4$, filtered and concentrated in vacuo to give the titled compound (crude, 519 mg) as an off-white waxy solid: HRMS (ESI+) calcd for C$_{21}$H$_{26}$O$_4$+H, 343.1909, found 343.1903. This material was used for the next step without further purification.

(4,5,5'-Trimethyl-2',9',10',10a'-tetrahydro-1'H-spiro[[1,3]dioxolane-2,3'-phenanthren]-10a'-yl)methanol (68)

To a solution of methyl 4,5,5'-trimethyl-2',9',10',10a'-tetrahydro-1'H-spiro[[1,3]dioxolane-2,3'-phenanthrene]-10a'-carboxylate (519 mg) in anhydrous Et$_2$O (30 mL) was added LAH (56 mg, 1.46 mmol) slowly in batches. The mixture was stirred at rt for 1 h. To the reaction mixture were added water (0.24 mL), 40% aqueous NaOH solution (0.18 mL), and water (0.48 mL) sequentially. After stirring at rt for 1 h, the upper solution was decanted and the resultant off-white gummy solid in the reaction flask was washed with Et$_2$O (25 mL×3). The combined organic layer was dried over MgSO$_4$, filtered and concentrated in vacuo to give a residue, which was purified by flash column chromatography [hexanes/EtOAc (2:1)] to afford 68 (193 mg, 0.61 mmol, 96% over two steps) as a colorless waxy solid: HRMS (ESI+) calcd for C$_{20}$H$_{26}$O$_3$+H, 315.1960, found 315.1956.

4,5,5'-Trimethyl-2',9',10',10a'-tetrahydro-1'H-spiro[[1,3]dioxolane-2,3'-phenanthrene]-10a'-carbaldehyde A solution of oxalyl chloride (106 μL, 1.35 mmol) in CH$_2$Cl$_2$ (8 mL) was stirred in the bath at about −65° C. in an isopropanol-dry ice bath for 20 min. To the mixture was added a solution of DMSO (75 μL, 2.45 mmol) in CH$_2$Cl$_2$ (1 mL) dropwise and then the mixture was stirred for 10 min. To the mixture was added a solution of 68 (193 mg, 0.61 mmol) in CH$_2$Cl$_2$ (2 mL) dropwise and then the mixture was stirred for 20 min at −65° C. To the reaction mixture were added Et$_3$N (428 μL) and water (8 mL) after removal of the cooling bath. After dilution with CH$_2$Cl$_2$-Et$_2$O (1:2, 40 mL), the organic layer was washed with 5% aqueous HCl solution (10 mL×2), water (10 mL×2), saturated aqueous NaHCO$_3$ solution (10 mL×2), and brine (10 mL×2), dried over MgSO$_4$, filtered and concentrated in vacuo to give the titled compound (crude, 226 mg) as an off-white waxy solid: HRMS (ESI+) calcd for C$_{20}$H$_{24}$O$_3$+H, 313.1804, found 313.1798. This material was used for the next step without further purification.

10a'-Ethynyl-4,5,5'-trimethyl-2',9',10',10a'-tetrahydro-1'H-spiro[[1,3]dioxolane-2,3'-phenanthrene]

To a solution of 4,5,5'-trimethyl-2',9',10',10a'-tetrahydro-1'H-spiro[[1,3]dioxolane-2,3'-phenanthrene]-10a'-carbaldehyde (226 mg) and K$_2$CO$_3$ (185 mg, 1.34 mmol) in anhydrous MeOH (25 mL) was added Ohira reagent[16] (41 mg, 0.74 mmol) dropwise. The mixture was stirred at rt for 3.5 h. The reaction mixture was concentrated in vacuo to remove solvent. The resultant residue was treated with water (10 mL) and CH$_2$Cl$_2$-Et$_2$O (1:2, 30 mL). The organic layer was washed with saturated aqueous NaHCO$_3$ solution (10 mL×2). The aqueous layer was extracted with CH$_2$Cl$_2$-Et$_2$O (1:2, 15 mL×3). The combined organic layer was dried over MgSO$_4$, filtered and concentrated in vacuo to give the titled compound (crude, 208 mg) as an off-white solid: HRMS (ESI+) calcd for C$_{21}$H$_{24}$O$_2$+H, 309.1855, found 309.1851. This material was used for the next step without further purification.

10a-Ethynyl-5-methyl-1,9,10,10a-tetrahydrophenanthren-3(2H)-one

To a solution of 10a'-ethynyl-4,5,5'-trimethyl-2',9',10',10a'-tetrahydro-1'H-spiro[[1,3]dioxolane-2,3'-phenanthrene] (crude, 208 mg) in MeOH (30 mL) was added 10% aqueous HCl solution (4 mL). The mixture was stirred at rt for 2 h. The reaction mixture was carefully neutralized with Et$_3$N (4 mL). After most of the solvent was removed in vacuo, the resultant residue was treated with water (15 mL) and EtOAc (30 mL). The aqueous phase was extracted with EtOAc (15 mL×3). The combined organic layer was washed with brine (20 mL×2), dried over MgSO$_4$, filtered and concentrated in vacuo to give a residue, which was purified by flash column chromatography [hexanes/EtOAc (10:1)] to afford the titled compound (115 mg, 79% over three steps) as a colorless solid: $^1$H NMR (CDCl$_3$) δ 7.23-7.16 (m, 2H), 7.04 (d, J=7.2 Hz, 1H), 6.09 (s, 1H), 3.00 (ddd, J=17.0 Hz, 13.8 Hz, 5.3 Hz, 1H), 2.87 (ddd, J=15.3 Hz, 5.1 Hz, 5.1 Hz, 1H), 2.62-2.52 (m, 2H), 2.47 (s, 3H), 2.31-2.16 (m, 2H), 2.13 (s, 3H), 2.11-2.02 (m, 2H); $^{13}$C NMR (CDCl$_3$) δ 198.9, 156.7, 140.7, 136.3, 133.6, 129.7, 129.0, 126.9, 124.9, 85.6, 70.0, 37.4 36.1, 35.6, 35.1, 27.7, 21.2; HRMS (ESI+) calcd for C$_{17}$H$_{16}$O+H, 237.1279, found 237.1273.

10a-Ethynyl-2-(hydroxymethylene)-5-methyl-1,9,10,10a-tetrahydrophenanthren-3(2H)-one To a stirred solution of 10a-ethynyl-5-methyl-1,9,10,10a-tetrahydrophenanthren-3 (2H)-one (115 mg, 0.49 mmol) in PhH (3 mL) were added ethyl formate (216 μL, 2.67 mmol) and NaOMe (144 mg, 2.67 mmol) sequentially. After stirring at rt for 2.5 h, 5% aqueous HCl solution (5 mL) was added slowly to acidify the reaction mixture. The mixture was treated with CH$_2$Cl$_2$-Et$_2$O (1:2, 15 mL) and H$_2$O (10 mL). The aqueous layer was extracted with CH$_2$Cl$_2$-Et$_2$O (1:2, 15 mL×3). The combined organic layer was washed with brine (15 mL×2), dried over MgSO$_4$, filtered and concentrated in vacuo to give the titled compound (crude, 142 mg) as a bright yellow solid: $^1$H NMR (CDCl$_3$) δ 13.9 (brs, 1H), 7.77 (s, 1H), 7.23-7.18 (m, 2H), 7.05 (d, J=6.6 Hz, 1H), 6.21 (s, 1H), 2.88 (d, J=14.2 Hz, 1H), 2.80 (ddd, J=15.0 Hz, 4.1 Hz, 4.1 Hz, 1H), 2.60-2.55 (m, 2H), 2.53 (s, 1H), 2.12-2.07 (m, 2H), 1.95 (ddd, J=12.7 Hz, 12.7 Hz, 3.8 Hz, 1H); $^{13}$C NMR (CDCl$_3$) δ 187.3, 169.2, 153.4, 140.9, 136.2, 133.4, 129.8, 128.9, 125.5, 124.7, 106.3, 86.7, 69.8, 36.5, 36.2, 35.7, 28.1, 21.1; HRMS (ESI+) calcd for C$_{18}$H$_{16}$O$_2$+H, 265.1229, found 265.1223. This material was used for the next step without further purification.

6a-Ethynyl-1-methyl-5,6,6a,7-tetrahydrophenanthro[2,3-d]isoxazole

To a stirred solution of 10a-ethynyl-2-(hydroxymethylene)-5-methyl-1,9,10,10a-tetrahydrophenanthren-3(2H)-one (142 mg) in EtOH (10 mL) was added hydroxylamine hydrochloride (270 mg, 3.88 mmol) in water (1 mL). The mixture was heated under reflux for 1 h. After cooling to rt, the solvent was removed in vacuo and the resultant residue was treated with EtOAc (30 mL) and water (15 mL). The aqueous layer was extracted with EtOAc (10 mL×3). The combined organic layer was washed with brine (20 mL×2), dried over MgSO$_4$, filtered and concentrated in vacuo to give the titled compound (crude, 156 mg) as a pale yellow solid: $^1$H NMR (CDCl$_3$) δ 8.19 (s, 1H), 7.21-7.16 (m, 2H), 7.06 (d, J=6.4 Hz, 1H), 6.68 (s, 1H), 3.01 (s, 3H), 2.81 (ddd, J=14.9 Hz, 4.2 Hz, 4.2 Hz, $^1$H), 2.64-2.49 (m, 4H), 2.12 (ddd, J=13.2 Hz, 4.1 Hz, 4.1 Hz, 1H), 1.96 (s, 1H), 1.91 (dd, J=13.0 Hz, 3.8 Hz, 1H); $^{13}$C NMR (CDCl$_3$) δ 165.9, 148.3, 141.1, 140.0, 135.6, 134.1, 129.8, 127.9, 124.7, 113.4, 108.8, 88.1, 67.9, 37.2, 36.9, 31.8, 28.4, 21.2; HRMS (ESI+) calcd for C$_{18}$H$_{15}$NO+H, 262.1232, found 262.1227. This material was used for the next step without further purification.

10a-Ethynyl-5-methyl-3-oxo-1,2,3,9,10,10a-hexahydrophenanthrene-2-carbonitrile To a stirred solution of NaOMe (419 mg, 7.76 mmol) in anhydrous MeOH (15 mL) was added a solution of 6a-ethynyl-1-methyl-5,6,6a,7-tetrahydrophenanthro[2,3-d]isoxazole (156 mg) in anhydrous MeOH (10 mL). The mixture was stirred at rt for 1 h. After the solvent was removed in vacuo, the resultant residue was diluted with EtOAc (60 mL). The organic solution was washed with 5% aqueous HCl solution (15 mL×2), saturated aqueous NaHCO$_3$ solution (15 mL×2), and brine (15 mL×2), dried over MgSO$_4$, filtered and concentrated in vacuo to give a residue, which was purified by flash column chromatography [hexanes/EtOAc (3:1)] to afford the titled compound (81 mg, 64% over three steps) as a pale yellow solid: $^1$H NMR (CDCl$_3$) δ 7.28-7.24 (m, 1H), 7.18 (d, J=7.6 Hz, 1H), 7.07 (d, J=7.6 Hz, 1H), 6.18 (s, 1H), 4.23 (dd, J=13.9 Hz, 4.1 Hz, 1H), 2.96 (ddd, J=15.8 Hz, 5.6 Hz, 5.6 Hz, 1H), 2.68-2.61 (m, 2H), 2.50 (d, J=13.2 Hz, 1H), 2.45 (s, 3H), 2.26 (s, 1H), 2.18-2.05 (m, 2H); $^{13}$C NMR (CDCl$_3$) δ 187.6, 157.6, 140.4, 136.8, 132.1, 130.2, 129.9, 125.5, 124.5, 116.4, 83.2, 72.1, 39.2, 37.8, 36.8, 36.3, 29.6, 27.4, 21.5; HRMS (ESI+) calcd for C$_{18}$H$_{15}$NO+H, 262.1232, found 262.1226.

10a-Ethynyl-5-methyl-3-oxo-3,9,10,10a-tetrahydrophenanthrene-2-carbonitrile (13)

To a solution of PhSeCl (91 mg, 0.48 mmol) in anhydrous CH$_2$Cl$_2$ (5 mL) was added a solution of pyridine (45 μL, 0.52 mmol) in anhydrous CH$_2$Cl$_2$ (1 mL) at 0° C. After the mixture was stirred at 0° C. for 20 min, to the mixture was added a solution of 10a-ethynyl-5-methyl-3-oxo-1,2,3,9,10,10a-hexahydrophenanthrene-2-carbonitrile (62 mg, 0.24 mmol) in anhydrous CH$_2$Cl$_2$ (3 mL) at 0° C. The mixture was stirred at 0° C. for 1 h. The reaction mixture was washed with 10% aqueous HCl solution (2 mL×2). At 0° C., 30% aqueous H$_2$O$_2$ solution (60 μL) was added 5 times at 10 min interval. After the 5$^{th}$ h addition, the mixture was stirred at 0° C. for additional 20 min. The reaction mixture was washed with water (5 mL×2), saturated aqueous NaHCO$_3$ solution (10 mL) and brine (10 mL), dried over MgSO$_4$, filtered and concentrated in vacuo to give a residue, which was purified by flash column chromatography [hexanes/EtOAc (4:1)] to afford 13 (62 mg, 100%, 50% from 68) as a pale yellow solid: mp 195.5-197° C.; $^1$H NMR (CDCl$_3$) δ 7.61 (s, 1H), 7.26 (d, J=7.6 Hz, 1H), 7.18 (d, J=7.4 Hz, 1H), 7.09 (d, J=7.6 Hz, 1H), 6.50 (s, 1H), 3.43 (ddd, J=17.8 Hz, 11.6 Hz, 6.4 Hz, 1H), 3.12 (dd, J=17.5 Hz, 6.3 Hz, 1H), 2.51 (s, 3H), 2.50-2.46 (m, 1H), 2.21 (s, 1H), 1.96 (ddd, J=12.1 Hz, 12.1 Hz, 6.5 Hz, 1H); $^{13}$C NMR (CDCl$_3$) δ 178.4, 159.3, 156.2, 137.2, 136.7, 131.5, 130.2, 129.9, 126.6, 124.8 115.9, 113.5, 77.7, 73.6, 39.5, 35.9, 26.3, 21.9; HRMS (ESI+) calcd for C$_{18}$H$_{13}$NO+H, 260.1075, found 260.1069. Anal. Calcd for C$_{18}$H$_{13}$NO.1/5H$_2$O: C, 82.23; H, 5.14; N, 5.33. Found: C, 82.28; H, 5.17, N, 5.18.

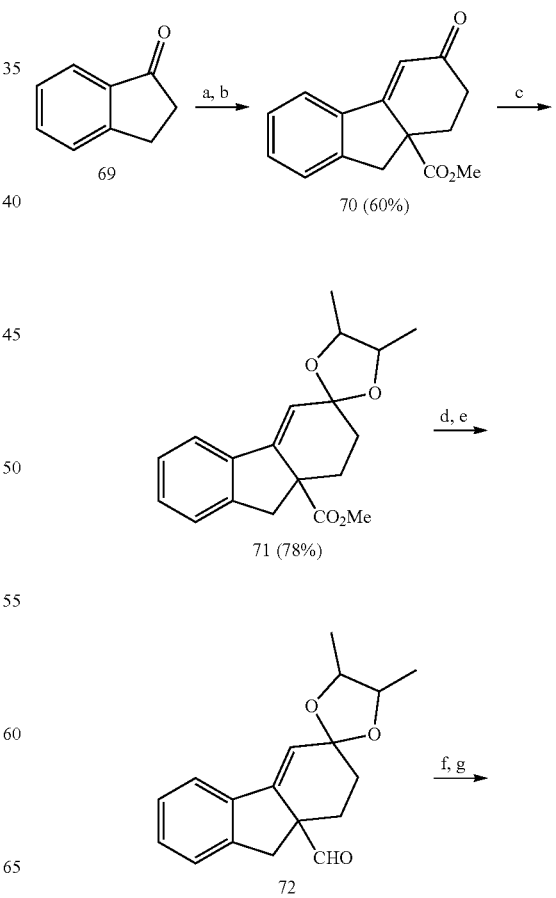

Scheme 10A (X = H).$^a$
Synthesis of tricyclic ethynylcyanodienone (flourenone skeleton) 14

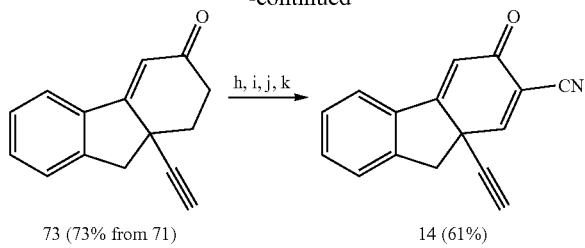

73 (73% from 71)  14 (61%)

[a]Reagents: (a) NaH, Me$_2$CO$_3$; (b) methyl vinyl ketone, NaOMe, MeOH; (c) 2,3-butanediol, PPTS, toluene; (d) LAH, Et$_2$O; (e) (COCl)$_2$, DMSO, CH$_2$Cl$_2$; (f) Ohira reagent, K$_2$CO$_3$, MeOH; (g) 10% aqueous HCl, MeOH; (h) HCO$_2$Et, NaOMe, PhH; (i) NH$_2$OH·HCl, aqueous EtOH; (j) NaOMe, MeOH, Et$_2$O; (k) PhSeCl, pyridine, CH$_2$Cl$_2$; 30% aqueous H$_2$O$_2$, CH$_2$Cl$_2$.

Methyl 1-oxo-2,3-dihydro-1H-indene-2-carboxylate

To a suspension of NaH (60% in mineral oil, 2.40 g, 0.06 mol) in dimethyl carbonate (30 mL) was added a solution of 1-indanone (69) (3.30 g, 0.025 mol) in dimethyl carbonate (50 mL) at rt. The mixture was heated under reflux for 2 h. After cooling to rt, the reaction mixture was poured into ice water and extracted with EtOAc (200 mL×3). The combined organic layer was dried over MgSO$_4$, filtered and concentrated in vacuo to the titled compound (crude, 5.54 g) as a pale yellow solid: $^1$H NMR (CDCl$_3$ The compound was observed as a mixture of keto and enol isomers.) Keto isomer: δ 7.75 (1H, d, J=7.4 Hz), 7.60 (1H, t, J=7.4 Hz), 7.49-7.36 (2H, m), 3.77 (3H, s), 3.74-3.71 (1H, m), 3.57-3.49 (2H, m), 3.35 (1H, dd, J=18.0 Hz, 4.2 Hz). This material was used for the next step without further purification.

Methyl 3-oxo-2,3,9,9a-tetrahydro-1H-fluorene-9a-carboxylate (70)

To a solution of methyl 1-oxo-2,3-dihydro-1H-indene-2-carboxylate (4.76 g, 25 mmol) and NaOMe (4.05 g, 75 mmol) in MeOH (100 mL) was added methyl vinyl ketone (2.61 mL, 31.25 mmol) dropwise at rt. The mixture was heated at 50° C. for 1 h and then was heated at 80° C. for 1 h. After cooling to rt, the solvent was removed in vacuo and the resultant residue was treated with CH$_2$Cl$_2$ (150 mL) and water (150 mL). The aqueous layer was extract with CH$_2$Cl$_2$ (100 mL×3). The combined organic layer was washed with brine (100 mL×2), dried over MgSO$_4$, filtered and concentrated in vacuo to give a residue, which was purified by flash column chromatography [hexanes/EtOAc/CH$_2$Cl$_2$ (5:1:1)] to afford 70 (3.63 g, 60%) as a pale yellow solid: $^1$H NMR (CDCl$_3$) δ 7.61 (1H, d, J=7.4 Hz), 7.42 (1H, t, J=7.0 Hz), 7.40-7.27 (2H, m), 6.38 (1H, s), 3.64 (3H, s), 3.58 (1H, d, J=16.5 Hz), 3.06 (1H, d, J=16.5 Hz), 2.79-2.76 (1H, m), 2.56-2.53 (2H, m), 2.21-2.13 (1H, m); $^{13}$C NMR (CDCl$_3$) δ 198.6, 173.8, 164.4, 145.6, 138.0, 131.9, 127.7, 125.3, 122.9, 119.1, 54.5, 52.8, 43.0, 35.1, 32.9; HRMS (ESI+) calcd for C$_{15}$H$_{14}$O$_3$+H, 243.1021, found 243.1011.

Methyl 4,5-dimethyl-1',2',9',9a'-tetrahydrospiro[[1,3]dioxolane-2,3'-fluorene]-9a'-carboxylate (71)

A mixture of 70 (200 mg, 0.83 mmol), 2,3-butane-diol (599 μL, 6.60 mmol), and PPTS (20.7 mg) in anhydrous toluene (30 mL) was heated under reflux for 3 h using a Dean-Stark apparatus. After cooling down to rt, the solvent was removed in vacuo. The resultant residue was treated with water (40 mL) and CH$_2$Cl$_2$-Et$_2$O (1:2, 40 mL). The organic layer was washed with saturated NaHCO$_3$ solution (10 mL×2) and brine (10 mL×2), dried over MgSO$_4$, filtered and concentrated in vacuo to give a residue, which was purified by flash column chromatography [hexanes/EtOAc (5:1)] to afford 71 (204 mg, 78%) as a pale yellow solid: $^1$H NMR (CDCl$_3$) δ 7.47 (1H, s), 7.20 (3H, s), 5.91 (1H, s), 3.78 (1H, t, J=8.3 Hz), 3.58 (3H, s), 3.36 (1H, d, J=16.0 Hz), 2.93 (1H, d, J=16.0 Hz), 2.55-2.49 (1H, m), 2.12-1.92 (3H, m), 1.35-1.18 (6H, m); HRMS (ESI+) calcd for C$_{19}$H$_{22}$O$_4$+H, 315.1596, found 315.1596.

(4,5-Dimethyl-1',2',9',9a'-tetrahydrospiro[[1,3]dioxolane-2,3'-fluoren]-9a'-yl)methanol To a solution of 71 (204 mg) in anhydrous Et$_2$O (25 mL) was added LAH (57 mg, 1.50 mmol) in batches. After the mixture was stirred at rt for 1 h, water (0.3 mL), 40% aqueous NaOH solution (0.21 mL), and water (0.6 mL) were added to the mixture sequentially. The mixture was stirred at rt for 1 h. After the upper solution was decanted, the resultant off-white gummy solid in the reaction flask was washed with Et$_2$O (25 mL×3). The combined organic layer was dried over MgSO$_4$, filtered and concentrated in vacuo to give the titled compound (crude, 191 mg) as a pale yellow oily solid: HRMS (ESI+) calcd for C$_{18}$H$_{22}$O$_3$+H, 287.1647, found 287.1639. This material was used fir the next step without further purification.

4,5-Dimethyl-1',2',9',9a'-tetrahydrospiro[[1,3]dioxolane-2,3'-fluorene]-9a'-carbaldehyde (72)

A solution of oxalyl chloride (62 μL, 0.72 mmol) in CH$_2$Cl$_2$ (8 mL) was stirred at about −65° C. in an isopropanol-dry ice bath for 20 min. To the stirred solution was added a solution of DMSO (93 μL, 1.30 mmol) in CH$_2$Cl$_2$ (1 mL) dropwise. After stirring for 10 min, to the stirred solution was added a solution of (4,5-dimethyl-1',2',9',9a'-tetrahydrospiro[[1,3]dioxolane-2,3'-fluoren]-9a'-yl)methanol (191 mg) in CH$_2$Cl$_2$ (2 mL) dropwise. Then, the mixture was stirred at −65° C. for 20 min. To the reaction mixture were added Et$_3$N (454 μL) and water (6 mL) after removal of the cooling bath. After dilution with CH$_2$Cl$_2$-Et$_2$O (1:2, 50 mL), the organic layer was washed with 5% aqueous HCl solution (10 mL×2), water (10 mL×2), saturated aqueous NaHCO$_3$ solution (10 mL×2) and brine (10 mL×2), dried over MgSO$_4$, filtered and concentrated in vacuo to give 72 (crude, 190 mg) as a foamy solid: HRMS (ESI+) calcd for C$_{18}$H$_{20}$O$_3$O+H, 284.1491, found 285.1498. This material was used for the next step without further purification.

9a'-Ethynyl-4,5-dimethyl-1',2',9',9a'-tetrahydrospiro[[1,3]dioxolane-2,3'-fluorene]

To a solution of 72 (190 mg) and K$_2$OC$_3$ (180 mg, 1.30 mmol) in anhydrous MeOH (30 mL) was added Ohira reagent[3] (150 mg, 0.78 mmol) dropwise. The mixture was stirred at rt for 3 h. After the reaction mixture was concentrated in vacuo to remove the solvent, the resultant residue was treated with water (15 mL) and CH$_2$Cl$_2$-Et$_2$O (1:2, 30 mL). The aqueous layer was extracted with CH$_2$Cl$_2$-Et$_2$O (1:2, 10 mL×3). The combined organic layer was washed with saturated aqueous NaHCO$_3$ solution (20 mL×3) and brine (20 mL×3), dried over MgSO$_4$, filtered and concentrated in vacuo to give the titled compound (crude, 204 mg) as a pale yellow solid: HRMS (ESI+) calcd for C$_{19}$H$_{20}$O$_2$+

H, 281.1542, found 281.1550. This material used for the next step without further purification.

9a-Ethynyl-9,9a-dihydro-1H-fluoren-3(2H)-one (73)

To a solution of 9a'-Ethynyl-4,5-dimethyl-1',2',9',9a'-tetrahydrospiro[[1,3]dioxolane-2,3'-fluorene] (204 mg) in MeOH (30 mL) was added 10% aqueous HCl solution (4 mL). The mixture was stirred at rt for 30 min. The reaction mixture was carefully neutralized with Et$_3$N (4 mL). After most of the solvent was removed in vacuo, the resultant residue was treated with water (15 mL) and EtOAc (30 mL). The aqueous phase was extracted with EtOAc (15 mL×3). The combined organic layer was washed with brine (20 mL×2), dried over MgSO$_4$, filtered and concentrated in vacuo to afford a residue, which was purified by flash column chromatography [hexanes/EtOAc (5:1)] to afford 73 (99 mg, 73% from 71) as a colorless solid: $^1$H NMR (CDCl$_3$) δ 7.62 (1H, d, J=7.6 Hz), 7.46-7.33 (3H, m), 6.28 (1H, s), 3.47 (1H, d, J=16.0 Hz), 3.08 (1H, d, J=16.0 Hz), 2.98 (1H, ddd, J=18.0 Hz, 12.6 Hz, 4.4 Hz), 2.61-2.49 (2H, m), 2.17-2.09 (2H, m); $^{13}$C NMR (CDCl$_3$) δ 198.8, 166.1, 146.0, 136.7, 132.1, 127.7, 125.7, 123.5, 117.7, 86.0, 68.8, 45.7, 42.7, 35.3, 34.6; HRMS (ESI+) calcd for C$_{15}$H$_{12}$O+H, 209.0966, found 209.0984.

9a-Ethynyl-2-(hydroxymethylene)-9,9a-dihydro-1H-fluoren-3 (2H)-one

To a stirred solution of 73 (99 mg, 0.47 mmol) in PhH (3 mL) were added ethyl formate (211 μL, 2.61 mmol) and NaOMe (141 mg, 2.61 mmol) sequentially. After stirring at rt for 1 h, 5% aqueous HCl solution (5 mL) was added slowly to acidify the reaction mixture. The resultant mixture was treated with CH$_2$Cl$_2$-Et$_2$O (1:2, 15 mL) and water (10 mL). The aqueous layer was extracted with CH$_2$Cl$_2$-Et$_2$O (1:2, 15 mL×3). The combined organic layer was washed with brine (20 mL×2), dried over MgSO$_4$, filtered and concentrated in vacuo to give the titled compound (90 mg) as a bright yellow solid: $^1$H NMR (CDCl$_3$) δ 14.3 (1H, brs), 7.80 (1H, s), 7.66 (1H, d, J=7.6 Hz), 7.48-7.34 (3H, m), 3.51 (1H, d, J=16.0 Hz), 3.06 (1H, d, J=16.0 Hz), 2.89 (1H, d, J=13.5 Hz), 2.67 (1H, d, J=13.5 Hz), 1.99 (1H, s); $^{13}$C NMR (CDCl$_3$) δ 188.2, 169.5, 162.6, 146.9, 136.1, 132.0, 127.8, 125.8, 123.6, 116.0, 106.4, 86.2, 68.4, 45.5, 41.8, 35.7; HRMS (ESI+) calcd for C$_{16}$H$_{12}$O$_2$+H, 237.0916, found 237.0945. This material was used for the next step without further purification.

4a-Ethynyl-4a,5-dihydro-4H-fluoreno[2,3-d]isoxazole

To a stirred solution of 9a-ethynyl-2-(hydroxymethylene)-9,9a-dihydro-1H-fluoren-3(2H)-one (90 mg) in EtOH (8 mL) was added a solution of hydroxylamine hydrochloride (264 mg, 3.79 mmol) in water (1 mL). The mixture was heated under reflux for 45 min. After cooling to rt, the solvent was removed in vacuo. The resultant residue was treated with EtOAc (30 mL) and water (15 mL). The aqueous layer was extracted with EtOAc (15 mL×3). The combined organic layer was washed with brine (20 mL×2), dried over MgSO$_4$, filtered and concentrated in vacuo to give a residue, which was purified by flash column chromatography [hexanes/EtOAc (4:1)] to afford the titled compound (81 mg, 92% over two steps) as a yellow solid: $^1$H NMR (CDCl$_3$) δ 8.21 (1H, s), 7.68 (1H, d, J=6.5 Hz), 7.42-7.36 (3H, m), 6.97 (1H, s), 3.54 (1H, d, J=16.0 Hz), 3.30 (1H, d, J=15.4 Hz), 3.01 (1H, d, J=16.0 Hz), 2.74 (1H, d, J=15.4 Hz), 1.84 (1H, s); $^{13}$C NMR (CDCl$_3$) δ 166.8, 150.9, 148.5, 145.7, 136.5, 130.2, 127.6, 125.8, 122.4, 109.8, 104.4, 87.3, 66.8, 45.8, 42.1, 31.3; HRMS (ESI+) calcd for C$_{16}$H$_{11}$NO+H, 234.0919, found 234.0950.

9a-Ethynyl-3-oxo-2,3,9,9a-tetrahydro-1H-fluorene-2-carbonitrile

To a solution of NaOMe (298 mg, 5.52 mmol) in anhydrous MeOH (10 mL) was added a solution of 4a-ethynyl-4a,5-dihydro-4H-fluoreno[2,3-d]isoxazole (81 mg, 0.35 mmol) in anhydrous MeOH (10 mL) and Et$_2$O (1 mL). The mixture was stirred at rt for 1 h. After most of the solvent was removed in vacuo, the resultant residue was treated with EtOAc (50 mL). The mixture was washed with 5% aqueous HCl solution (10 mL×2), saturated aqueous NaHCO$_3$ solution (10 mL×2), and brine (10 mL×2), dried over MgSO$_4$, filtered and concentrated in vacuo to give the titled compound (crude, 96 mg) as a pale yellow solid: $^1$H NMR (CDCl$_3$) δ 7.62 (1H, d, J=7.6 Hz), 7.51 (1H, t, J=7.2 Hz), 7.42-7.36 (2H, m), 6.34 (1H, s), 4.22 (1H, dd, J=13.2 Hz, 4.2 Hz), 3.51 (1H, d, J=16.0 Hz), 3.15 (1H, d, J=16.0 Hz), 2.89 (1H, dd, J=12.4 Hz, 4.2 Hz), 2.48 (1H, d, J=12.4 Hz, 12.4 Hz), 2.22 (1H, s); $^{13}$C NMR (CDCl$_3$) δ 187.6, 167.0, 145.8, 135.7, 133.1, 128.2, 125.9, 123.8, 116.8, 115.6, 83.9, 70.7, 44.9, 42.3, 38.4, 38.2; HRMS (ESI+) calcd for C$_{16}$H$_{11}$NO+H, 234.0919, found 234.0939. This material was used for the next step without further purification.

9a-Ethynyl-3-oxo-9,9a-dihydro-3H-fluorene-2-carbonitrile (14)

To a stirred solution of PhSeCl (132 mg, 0.69 mmol) in anhydrous CH$_2$Cl$_2$ (7 mL) was added a solution of pyridine (62 μL, 0.759 mmol) in anhydrous CH$_2$Cl$_2$ (5 mL) at 0° C. The mixture was stirred at 0° C. for 20 min. Then, to the mixture was added a solution of 9a-ethynyl-3-oxo-2,3,9,9a-tetrahydro-1H-fluorene-2-carbonitrile (96 mg) in anhydrous CH$_2$Cl$_2$ (2 mL) at 0° C. The mixture was stirred at 0° C. for 1 h. The reaction mixture was washed with 10% aqueous HCl solution (2 mL×2). At 0° C., 30% aqueous H$_2$O solution (60 μL) was added five times at 10 min interval. After the 5th addition, the mixture was stirred at 0° C. for additional 20 min. The reaction mixture was washed with water (5 mL×2), saturated aqueous NaHCO$_3$ solution (10 mL) and brine (5 mL×2), dried over MgSO$_4$, filtered and concentrated in vacuo to give a residue, which was purified by flash column chromatography [hexanes/EtOAc (6:1)] to afford 14 (57 mg, 66% over two steps, 61% from 73) as a pale yellow solid: mp 202-203° C.; $^1$H NMR (CDCl$_3$) δ 7.80 (1H, s), 7.67 (1H, d, J=7.6 Hz), 7.52-7.40 (3H, m), 6.59 (1H, s), 3.54 (1H, d, J=14.6 Hz), 3.28 (1H, d, J=14.6 Hz), 2.19 (1H, s); $^{13}$C NMR (CDCl$_3$) δ 178.8, 164.0, 154.6, 144.2, 136.1, 132.4, 128.5, 126.2, 123.4, 118.0, 117.9, 113.8, 81.5, 70.5, 45.1, 42.9; HRMS (ESI+) calcd for C$_{16}$H$_9$NO+H, 232.0762, found 232.0784. Anal. Calcd for C$_{16}$H$_9$NO: C, 83.10; H, 3.92; N, 6.06. Found: C, 82.91; H, 3.90; N, 5.94.

Scheme 10B (X = Cl).$^a$
Synthesis of tricyclic ethynylcyanodienone (flourenone skeleton) 15

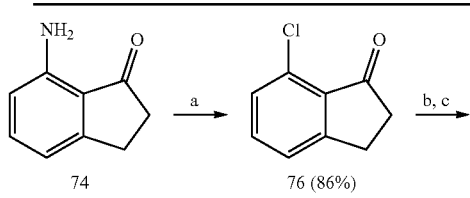

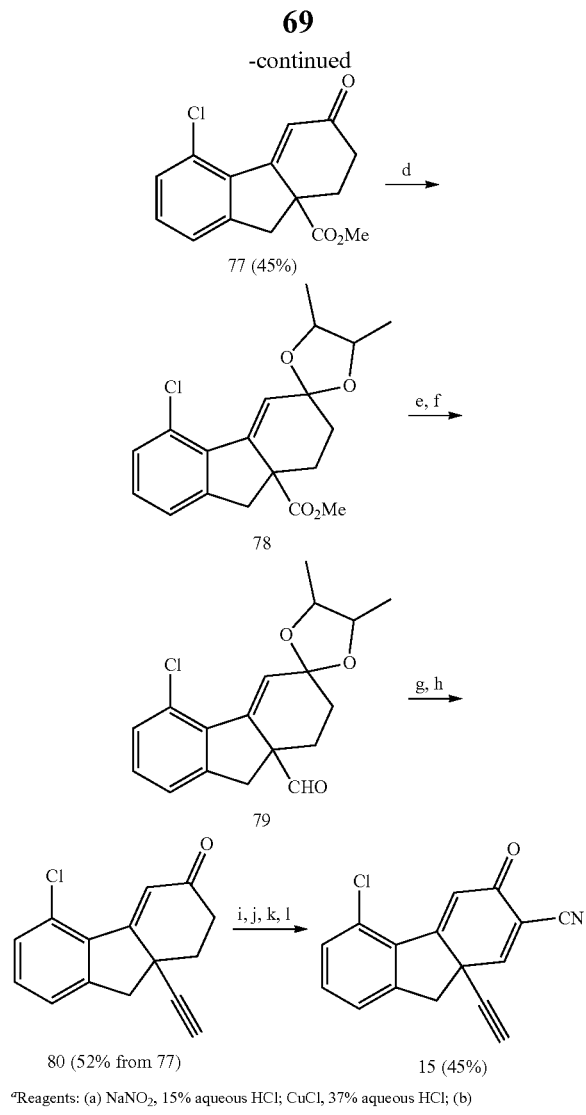

*Reagents: (a) NaNO₂, 15% aqueous HCl; CuCl, 37% aqueous HCl; (b) NaH, Me₂CO₃; (c) methyl vinyl ketone, NaOMe, MeOH; (d) 2,3-butanediol, PPTS, toluene; (e) LAH, Et₂O; (f) (COCl)₂, DMSO, CH₂Cl₂; (g) Ohira reagent, K₂CO₃, MeOH; (h) 10% aqueous HCl, MeOH; (i) HCO₂Et, NaOMe, PhH; (j) NH₂OH·HCl, aqueous EtOH; (k) NaOMe, MeOH; (l) PhSeCl, pyridine, CH₂Cl₂; 30% aqueous H₂O₂, CH₂Cl₂.

7-Chloro-2,3-dihydro-1H-inden-1-one (76)

To 7-amino-1-indanone (74) (300 mg, 2.04 mmol), which was placed in a flask, was added 15% aqueous HCl solution (5 mL) at rt until the mixture became a homogeneous solution. To the solution was added a solution of NaNO₂ (169 mg) in water (2 mL) dropwise at 0° C. After stirring at 0° C. for 15 min, the resultant red solution was added dropwise to a solution of CuCl (706 mg, 7.13 mmol) in 37% aqueous HCl solution (8 mL) at 0° C. The reaction mixture was stirred at 0° C. for 1 h. The mixture was extracted with EtOAc (25 mL×3). The combined extract was washed with saturated aqueous NaHCO₃ solution (20 mL×3) and brine (20 mL×3), dried over MgSO₄, filtered and concentrated in vacuo to give a residue, which was purified by flash column chromatography [hexanes/EtOAc (4:1)] to afford 76 (290 mg, 86%) as a pale yellow solid: $^1$H NMR (300 MHz, CDCl₃) δ 7.49 (1H, t, J=7.7 Hz), 7.38 (1H, d, J=7.6 Hz), 7.32 (1H, d, J=7.7 Hz), 3.13 (2H, t, J=6.2 Hz), 2.75 (2H, t, J=6.1 Hz).

Methyl 7-chloro-1-oxo-2,3-dihydro-1H-indene-2-carboxylate

To a suspension of NaH (60% in mineral oil, 295 mg, 7.38 mmol) in dimethyl carbonate (5 mL) was added a solution of 76 (410 mg, 2.46 mmol) in dimethyl carbonate (20 mL) at rt. The mixture was heated under reflux for 4 h. After cooling to rt, the reaction mixture was poured into ice water and extracted with EtOAc (30 mL×3). The combined extract was washed with brine (30 mL×2), dried over MgSO₄, filtered and concentrated in vacuo to give a residue, which was purified by flash column chromatography [hexanes/EtOAc (5:1)] to afford the titled compound (437 mg, 79%) as a pale yellow solid: $^1$H NMR (500 MHz, CDCl₃, The compound was observed as a mixture of keto and enol isomers.) Keto isomer: δ 7.38-7.34 (3H, m), 3.88 (3H, s,), 3.53 (2H, s); HRMS (ESI+) calcd for C₁₁H₉ClO₃+H, 225.0318, found 225.0319.

Methyl 5-chloro-3-oxo-2,3,9,9a-tetrahydro-1H-fluorene-9a-carboxylate (77)

To a mixture of methyl 7-chloro-1-oxo-2,3-dihydro-1H-indene-2-carboxylate (220 mg, 0.98 mmol) and NaOMe (162 mg, 2.93 mmol) in MeOH (13 mL) was added methyl vinyl ketone (105 μL, 1.22 mmol) dropwise at rt. The mixture was heated at 50° C. for 1 h and then was heated at 90° C. for 1 h. After cooling to rt, 5% aqueous HCl solution (2.5 mL) was added to adjust pH to neutral. The solvent was removed in vacuo and the resultant residue was treated with CH₂Cl₂ (30 mL) and water (30 mL). The aqueous layer was extract with CH₂Cl₂ (10 mL×3). The combined organic layer was washed with brine (20 mL×2), dried over MgSO₄, filtered and concentrated in vacuo to give a residue, which was purified by flash column chromatography [hexanes/EtOAc/CH₂Cl₂ (4:1:2)] to afford 77 (194 mg, 57%, 45% from 76) as a pale yellow oil: $^1$H NMR (CDCl₃) δ 7.29 (2H, d, J=4.8 Hz), 7.21 (1H, t, J=4.3 Hz), 7.05 (1H, s), 3.65 (3H, s), 3.57 (1H, d, J=16.5 Hz), 3.05 (1H, d, J=16.4 Hz), 2.78-2.73 (1H, m), 2.58-2.54 (2H, m), 2.23-2.15 (1H, m); $^{13}$C NMR (CDCl₃) δ 198.9, 173.5, 147.9, 132.0, 131.8, 130.2, 129.3, 123.5, 123.4, 54.4, 52.9, 43.0, 34.6, 32.8; HRMS (ESI+) calcd for C₁₅H₁₃ClO₃+H, 277.0631, found 277.0631.

Methyl 5-chloro-4,5-dimethyl-1',2',9',9a'-tetrahydrospiro [[1,3] dioxolane-2,3'-fluorene]-9a'-carboxylate (78)

A mixture of 77 (260 mg, 0.94 mmol), 2,3-butane-diol (682 μL, 7.526 mmol), and PPTS (20 mg) in anhydrous toluene (25 mL) was heated under reflux for 6 h using a Dean-Stark apparatus. After cooling down to rt, the solvent was removed in vacuo. The resultant residue was treated with water (40 mL) and CH₂Cl₂-Et₂O (1:2, 40 mL). The organic layer was washed with saturated aqueous NaHCO₃ solution (10 mL×2) and brine (10 mL×2), dried over MgSO₄, filtered and concentrated in vacuo to give 78 (crude, 502 mg) as a yellow oil: HRMS (ESI+) calcd for C₁₉H₂₁ClO₄+H, 349.1207, found 349.1211. This material was used for the next step without further purification.

(5'-Chloro-4,5-dimethyl-1',2',9',9a'-tetrahydrospiro [[1,3]dioxolane-2,3'-fluoren]-9a'-yl)methanol To a solution of 78 (502 mg) in anhydrous Et₂O (30 mL) was added LiAlH (82 mg, 2.16 mmol) slowly in batches. The mixture was stirred at rt for 2.5 h. To the reaction mixture were added water (0.42 mL), 40% aqueous NaOH solution (0.30 mL), and water (0.88 mL) sequentially. After stirring at rt for 1 h, the upper solution was decanted and the resultant off-white gummy solid in the reaction flask was washed with Et$_2$O (40 mL×3). The combined organic layer was dried over MgSO$_4$, filtered and concentrated in vacuo to give the titled compound (crude, 361 mg) as a yellow sticky oil: HRMS (ESI+) calcd for C$_{18}$H$_{21}$ClO$_3$+H, 321.1257, found 321.1264. This material was used for the next step without further purification.

5'-Chloro-4,5-dimethyl-1',2',9',9a'-tetrahydrospiro [[1,3]dioxolane-2,3'-fluorene]-9a'-carbaldehyde (79)

To a solution of oxalyl chloride (100 μL, 1.13 mmol) in CH$_2$Cl$_2$ (6 mL) was stirred at about −65° C. in an isopropanol-dry ice bath for 20 min. To the mixture was added a solution of DMSO (160 μL, 2.26 mmol) in CH$_2$Cl$_2$ (2 mL) dropwise. The resultant mixture was stirred for 10 min. To the mixture was added a solution (2 mL) of (5'-chloro-4,5-dimethyl-1',2',9',9a'-tetrahydrospiro[[1,3]dioxolane-2,3'-fluoren]-9a'-yl)methanol (crude, 361 mg) dropwise and then the mixture was stirred at −65° C. for 20 min. To the reaction mixture were added Et$_3$N (656 μL) and water (8 mL) after removal of the cooling bath. After dilution with CH$_2$Cl$_2$-Et$_2$O (1:2, 40 mL), the organic layer was washed with 5% aqueous HCl solution (10 mL×2), water (10 mL×2), saturated aqueous NaHCO$_3$ solution (10 mL×2), and brine (10 mL×2), dried over MgSO$_4$, filtered and concentrated in vacuo to give 79 (crude, 320 mg) as a pale yellow oil: HRMS (ESI+) calcd for C$_{18}$H$_{19}$ClO$_3$+H, 319.1101, found 319.1100. This material was used for the next step without further purification.

5'-Chloro-9a'-ethynyl-4,5-dimethyl-1',2',9',9a'-tetrahydrospiro [[1,3]dioxolane-2,3'-fluorene]

To a solution of 79 (320 mg) and K$_2$OC$_3$ (130 mg, 1.88 mmol) in anhydrous MeOH (30 mL) was added Ohira reagent[3] (217 mg, 1.130 mmol) dropwise. After stirring at rt for 4.5 h, the reaction mixture was concentrated in vacuo to remove the solvent. The resultant residue was treated with water (20 mL) and CH$_2$Cl$_2$-Et$_2$O (1:2, 40 mL). The organic layer was washed with saturated aqueous NaHCO$_3$ solution (15 mL). The aqueous layer was extracted with CH$_2$Cl$_2$-Et$_2$O (1:2, 50 mL×3). The combined organic layer was washed with brine (40 mL×2), dried over MgSO$_4$, filtered and concentrated in vacuo to give the titled compound (crude, 442 mg) as a pale yellow oil: HRMS (ESI+) calcd for C$_{19}$H$_{19}$ClO$_2$+H, 315.1152, found 315.1153. This material was used for the next step without further purification.

5-Chloro-9a-ethynyl-9,9a-dihydro-1H-fluoren-3 (2H)-one (80)

To a solution of 5'-chloro-9a'-ethynyl-4,5-dimethyl-1',2', 9',9a'-tetra-hydrospiro[[1,3]dioxolane-2,3'-fluorene (442 mg) in MeOH (60 mL) was added 10% aqueous HCl solution (16 mL). The mixture was stirred at rt for 1.5 h. The reaction mixture was carefully neutralized with Et$_3$N (10 mL). After most of the solvent was removed in vacuo, the resultant residue was treated with water (25 mL) and EtOAc (40 mL). The aqueous phase was extracted with EtOAc (25 mL×3). The combined organic layer was washed with brine (30 mL×2), dried over MgSO$_4$, filtered and concentrated in vacuo to give a residue, which was purified by flash column chromatography [hexanes/EtOAc (6:1)] to afford 80 (119 mg, 52% from 77) as a pale yellow solid: $^1$H NMR (500 MHz, CDCl$_3$) δ 7.32-7.24 (3H, m), 6.90 (1H, s), 3.42 (1H, d, J=15.8 Hz), 3.06 (1H, d, J=15.8 Hz), 2.96 (1H, ddd, J=18.3 Hz, 13.8 Hz, 4.5 Hz), 2.57 (1H, d, J=17.6 Hz), 2.48 (1H, ddd, J=12.6 Hz, 4.7 Hz, 1.8 Hz), 2.16-2.11 (1H, m), 2.10 (1H, s); $^{13}$C NMR (125 MHz, CDCl$_3$) δ 199.1, 162.8, 148.3, 133.6, 132.6, 132.0, 129.3, 123.9, 122.1, 85.5, 69.2, 45.7, 42.8, 34.9, 34.5; HRMS (ESI+) calcd for C$_{19}$H$_{11}$ClO+ H, 243.0577, found 243.0575.

5-Chloro-9a-ethynyl-2-(hydroxymethylene)-9,9a-dihydro-1H-fluoren-3(2H)-one

To a stirred solution of 80 (119 mg, 0.49 mmol) in PhH (5 mL) were added ethyl formate (217 μL, 2.70 mmol) and NaOMe (146 mg, 2.70 mmol) sequentially. After stirring at rt for 1 h, 5% aqueous HCl solution (5 mL) was added slowly to acidify the reaction mixture. The mixture was treated with CH$_2$Cl$_2$-Et$_2$O (1:2, 15 mL) and water (10 mL). The aqueous layer was extracted with CH$_2$Cl$_2$-Et$_2$O (1:2, 15 mL×3). The combined organic layer was washed with brine (20 mL×2), dried over MgSO$_4$, filtered and concentrated in vacuo to give the titled compound (crude, 140 mg) as a bright yellow solid: $^1$H NMR (500 MHz, CDCl$_3$) δ 14.3 (1H, brs), 7.99 (1H, s), 7.36-7.29 (3H, m), 7.13 (1H, s), 3.49 (1H, d, J=15.9 Hz), 3.05 (1H, d, J=15.9 Hz), 2.91 (1H, d, J=14.1 Hz), 2.67 (1H, d, J=14.1 Hz), 2.00 (1H, s); $^{13}$C NMR (125 MHz, CDCl$_3$) δ 186.0, 172.8, 158.8, 149.2, 133.1, 132.8, 131.9, 129.4, 124.0, 120.5, 105.8, 85.9, 68.8, 45.5, 41.7, 35.4; HRMS (ESI+) calcd for C$_{16}$H$_{11}$ClO$_2$+H, 271.0526, found 271.0532. This material was used for the next step without further purification.

9-Chloro-4a-ethynyl-4a,5-dihydro-4H-fluoreno[2,3-d]isoxazole

To a stirred solution of 5-chloro-9a-ethynyl-2-(hydroxymethylene)-9,9a-dihydro-1H-fluoren-3(2H)-one (140 mg) in EtOH (15 mL) was added a solution of hydroxylamine hydrochloride (273 mg, 3.93 mmol) in water (2 mL). The mixture was heated under reflux for 2 h. After cooling to rt, the solvent was removed in vacua. The resultant residue was treated with EtOAc (30 mL) and water (20 mL). The aqueous layer was extracted with EtOAc (15 mL×3). The combined organic layer was washed with brine (20 mL×2), dried over MgSO$_4$, filterd and concentrated in vacuo to give the titled compound (crude 134 mg) as an orange solid: $^1$H NMR (500 MHz, CDCl$_3$) δ 8.22 (1H, s), 7.65 (1H, s), 7.34-7.26 (3H, m), 3.53 (1H, d, J=15.5 Hz), 3.30 (1H, d, J=15.3 Hz), 3.01 (1H, d, J=15.7 Hz), 2.75 (1H, d, J=15.5 Hz), 1.85 (1H, s); $^{13}$C NMR (125 MHz, CDCl$_3$) δ 166.7, 148.4, 148.0, 133.5, 131.5, 130.3, 129.1, 124.0, 110.0, 109.4, 86.9, 67.2, 45.7, 42.1, 31.4; HRMS (ESI+) calcd for C$_{16}$H$_{10}$ClNO+H, 268.0529, found 268.0535. This material was used for the next step without further purification.

5-Chloro-9a-ethynyl-3-oxo-2,3,9,9a-tetrahydro-1H-fluorene-2-carbonitrile

To a solution of NaOMe (424 mg, 7.86 mmol) in anhydrous MeOH (9 mL) was added a solution of 9-chloro-4a-ethynyl-4a,5-dihydro-4H-fluoreno[2,3-d]isoxazole (134 mg) in anhydrous MeOH (10 mL). The mixture was stirred at rt for 1 h. After the solvent was removed in vacuo, the resultant residue was diluted with EtOAc (40 mL). The organic solution was washed with 5% aqueous HCl solution (10 mL×2), saturated aqueous NaHCO₃ solution (10 mL×2), and brine (10 mL×2), dried over MgSO₄, filtered and concentrated in vacuo to give a residue, which was purified through a silica gel plug (eluting with hexanes/EtOAc=1:1) to afford the titled compound (123 mg, 94% over three steps) as a yellow solid: $^1$H NMR (500 MHz, CDCl₃) δ 7.39 (1H, t, J=7.6 Hz), 7.35 (1H, d, J=7.7 Hz), 7.31 (1H, d, J=7.3 Hz), 7.01 (1H, s), 4.23 (1H, dd, J=13.4 Hz, 4.2 Hz), 3.48 (1H, d, J=14.0 Hz), 3.15 (1H, d, J=15.8 Hz), 2.89 (1H, dd, J=12.5 Hz, 4.2 Hz), 2.52 (1H, t, J=13.0 Hz), 2.25 (1H, s); $^{13}$C NMR (125 MHz, CDCl₃) δ 188.0, 163.7, 148.0, 133.2, 133.0, 132.8, 129.8, 124.1, 120.0, 116.7, 83.6, 71.2, 45.0, 42.5, 38.4, 37.9; HRMS (ESI+) calcd for C₁₆H₁₀ClNO+H, 268.0529, found 268.0528.

5-Chloro-9a-ethynyl-3-oxo-9,9a-dihydro-3H-fluorene-2-carbonitrile (15)

To a solution of PhSeCl (176 mg, 0.92 mmol) in anhydrous CH₂Cl₂ (9 mL) was added a solution of pyridine (88 μL, 1.01 mmol) in anhydrous CH₂Cl₂ (5 mL) at 0° C. The mixture was stirred at 0° C. for 20 min. Then, to the mixture was added a solution of 5-chloro-9a-ethynyl-3-oxo-2,3,9,9a-tetrahydro-1H-fluorene-2-carbonitrile (123 mg, 0.46 mmol) in anhydrous CH₂Cl₂ (3 mL) at 0° C. The mixture was stirred at 0° C. for 1 h. The reaction mixture was washed with 10% aqueous HCl solution (2 mL×2). At 0° C., to the mixture was added 30% aqueous H₂O₂ solution (40 μL) five times at 10 min interval. After the 5$^{th}$ addition, the mixture was stirred at 0° C. for additional 20 min. The mixture was washed with water (5 mL×2), saturated aqueous NaHCO₃ solution (10 mL), and brine (10 mL), dried over MgSO₄, filtered and concentrated in vacuo to give a residue, which was purified by flash column chromatography [hexanes/EtOAc (4:1)] to afford 15 (58 mg, 486, 45% from 80) as a pale yellow solid: mp 191-193° C.; $^1$H NMR (300 MHz, CDCl₃) δ 7.78 (1H, s), 7.41-7.32 (3H, m), 7.20 (1H, s), 3.52 (1H, d, J=14.7 Hz), 3.25 (1H, d, J=14.7 Hz), 2.22 (1H, s); $^{13}$C NMR (CDCl₃) δ 179.0, 160.6, 154.4, 146.3, 133.3, 132.6, 132.4, 129.8, 124.5, 121.4, 117.7, 113.6, 81.0, 71.0, 45.1, 42.8; HRMS (ESI+) calcd for C₁₆H₈ClNO+H, 266.0373, found 266.0380. Anal. Calcd for C₁₆H₈ClNO.1/7H₂O: C, 71.63; H, 3.11; Cl, 13.22; N, 5.22. Found: C, 71.81; H, 3.00; Cl, 13.24; N, 5.20.

The present invention provides synthetic methods and chemical intermediates that may be used to synthesize additional cyanoenones. Additional compounds, which are synthesized according to methods similar to those described in Schemes 1-10 or according to methods known in the art, have analogous activity to compounds 4-15.

Example 1. Monocyclic Ethynylcyanodienones

Monocyclic diethynylcyanodienone 4 was synthesized in 9 steps from 2,2-dimethyl-1,3-dioxan-5-one by the sequence as shown in Scheme 1. Known dienophile precursor 16 (Fearnley, S. P. et al. 2000) was synthesized in 42% yield through Sonogashira coupling between triisopropylsilylacetylene (TIPS acetylene) and the triflate derived from 2,2-dimethyl-1,3-dioxan-5-one. Diels-Alder reaction between the Danishefsky's diene and 16 gave previously reported adduct 17 (Fearnley, S. P. et al. 2000). Without purification of the crude adduct, 17 was treated with (chloromethyl)triphenylphosphonium chloride (Mella, M. et al. 1988) in the presence of n-BuLi in THF to afford 18. Dehydrochlorination of 18 with LDA in THF, followed by quenching the acetylide with TMSCl produced 19 (Corey, E. J. & Ruden, R. A. 1973). Monocyclic enone 20 was obtained at pure state by the treatment of 19 with TFA in 1,2-dichloroethane, followed by flash column chromatography purification (33% yield from 16). Cyanation of the enolate of 20 generated using LDA in THF, with p-TsCN, gave 21 in 77% yield (Kahne, D. & Collum, D. B. 1981). Deprotection of 21 with TBAF in THF, followed by addition of PhSeCl in the presence of pyridine and subsequent oxidation/elimination of the selenated intermediate with 30% aqueous H₂O₂ solution afforded 4 in 57% yield (Liotta, D. et al. 1981).

Monocyclic ethynylvinylcyanodienone 5 was synthesized in 5 steps from the same adduct 17 as for 4 (Scheme 2). Wittig reaction on 17 with methyltriphenylphosphonium iodide in the presence of n-BuLI in THF provided 22. Enone 23 was obtained by the treatment of 22 with D-(+)-camphor sulfonic acid [D-(+)-CSA] in 1,4-dioxane under reflux conditions (35% yield from 17). The desired compound 5 was prepared in three steps in 40% yield via 24 and 25 from 23 by the same sequence (cyanation, deprotection, and insertion of a double bond) as for 4.

Monocyclic ethylethynylcyanodienone 6 was synthesized 6 steps from Diels-Alder adduct 27 which was obtained from the Danishefsky's diene and 2-ethylacrolein (26) under microwave conditions (Scheme 3) (Zheng, S. et al. 2013). Enone 30 was produced in 3 steps from 27 by the same sequence (Wittig reaction, convertsion of a chlorovinyl group to a TMS protected ethynyl group, and deprotection) as for 20 (21% yield from 26). Cyanation of the enolate of 30 with p-TsCN, followed by deprotection with TBAF gave 32 in 29% yield. Cyanodienone 6 was prepared in 79% yield from 32 by addition of PhSeCl in the presence of pyridine and subsequent oxidation/elimination of the selenated intermediate with 30% aqueous H₂O₂ solution.

Example 2. Bicyclic Ethynylcyanodienones

Bicyclic ethynylcyanodienone 7 was synthesized in 10 steps from previously reported compound 33 (Shirakawa, S. et al. 2007), which was prepared by Michael addition between methyl 2-oxocyclopentanecarboxylate and but-3-en-2-one (Scheme 4). Intramolecular aldol condensation of 33 in the presence of pyrrolidine (1 equiv) and acetic acid (1 equiv) in EtOAc gave enone 34 in 58% yield. Enone 34 was protected with ethylene glycol in the presence of PPTS in toluene to afford 35 in 95% yield. Reduction of 35 with LAH in Et₂O, followed by Swern oxidation produced 36. Without purification, 36 was treated with Ohira reagent (dimethyl (1-diazo-2-oxopropyl)phosphonate) to give 37 (48% yield from 35) (Ohira, S. 1989). The lithium acetylide, which was derived from 37 with MeLi, was protected with TBSCl to afford 38 in 92% yield. Removal of a ketal of 38 under acidic conditions, followed by cyanation of the lithium enolate of 39 with p-TsCN provided 40 (47% yield from 38). The desired compound 7 was obtained by deprotection of 40 with TBAF in THF, followed by DDQ oxidation in PhH (22% yield from 40).

Bicyclic ethynylcyanodienone 8, which has a nonenolizable cyanodienone while 7 has an enolizable cyanodienone, was synthesized in 11 steps from the known compound 42, which was obtained by methoxycarbonylation of 2,2-dimethylcyclopentanone (Scheme 5) (Vedejs, E. et al. 2003). Enone 43 was prepared by intramolecular aldol condensation of the adduct, which was obtained by Michael addition between 42 and but-3-en-2-one (53% yield). Conversion from 43 to 46 was achieved by the same sequence (ketalization, reduction, oxidation, and introduction of an ethynyl group) as for 37 (23% yield from 43). A cyano group was introduced using Johnson isoxazole method[18] instead of p-TsCN. Removal of a ketal of 46, followed by formylation with ethylformate in the presence of NaH in THF gave 47. Without purification, 47 was treated with hydroxylamine hydrochloride in aqueous EtOH to afford isoxazole 48 (46% yield from 46) (Johnson, W. S. & Shelberg, W. E. 1945). The desired compound 8 was obtained by cleavage of the isoxazole moiety of 48 with NaOMe in MeOH (Johnson, W. S. & Shelberg, W. E. 1945), followed by DDQ oxidation in PhH (46% yield).

Bicyclic ethynylcyanodienone 9, which has a naphthalene skeleton, was synthesized via the known compound 51 from 1,2,3,4-tetrahydronaphtalene-1-carboxylic acid (49) as shown in Scheme 6. We have obtained racemic 51 by a new sequence that is different from the previously reported synthesis (Nareddy, P. et al. 2012; Hulme, A. N. & Meyers, A. I. 1994) of optically active 51. Methyl ester 50 (Noji, M. et al. 2008) was prepared by methylation of 49, followed by insertion of a methyl group (79% yield). Reduction of 50 with LAH and subsequent Swern oxidation gave 51 (100% yield). A formyl group of 51 was converted to an ethynyl group of 52 with Ohira reagent (87% yield). Chromium-mediated allylic oxidation (Muzart, J. 1987) of 52 provided ketone 53 in 52% yield. Formylation of 53 with ethylformate in the presence of NaOMe in PhH (Clinton, R. O. et al), followed by isoxazole formation with hydroxylamine hydrochloride in aqueous EtOH afforded 55 in 84% yield. The desired compound 9 was obtained by cleavage of the isoxazole moiety of 55 with NaOMe in a mixture of MeOH and Et$_2$O, followed by addition of PhSeCl in the presence of pyridine and subsequent oxidation/elimination of the selenated intermediate with 30% aqueous H$_2$O$_2$ solution (92% yield).

Example 3. Tricyclic Ethynylcyanodienones

Tricyclic ethynylcyanodienone 10, which has a phenanthrene skeleton, was synthesized in 11 steps from 1-tetralone (Scheme 7). The known compound 56 (Jusribo, V. et al. 2007) was prepared by a new method which is different from the previously reported method. Methoxycarbonylation of 1-tetralone, followed by Robinson annulation with ethyl vinyl ketone gave 56 in 75% yield. After protection of an enone of 56 with ethylene glycol (93% yield), a methoxycarbonyl group of 57 was converted to a formyl group of 58 by reduction with LAH and subsequent Swern oxidation (67% yield). Transformation of a formyl group of 58 to an ethynyl group with Ohira reagent afforded 59 in 74% yield. Isoxazole 60 was prepared in 73% yield from 59 by deketalization under acidic conditions, followed by formylation with ethyl formate and subsequent isoxazole formation with hydroxylamine hydrochloride. The desired compound 10 was obtained by isoxazole cleavage of 60 with NaOMe, followed by addition of PhSeCl in the presence of pyridine and subsequent oxidation/elimination of the selenated intermediate with 30% aqueous H$_2$O$_2$ solution (82% yield).

Tricyclic ethynylcyanodienone 10, which has a phenanthrene skeleton, was synthesized in 11 steps from 1-tetralone (Scheme 7). The known compound 56 (Jusribo, V. et al. 2007) was prepared by a new method which is different from the previously reported method. Methoxycarbonylation of 1-tetralone, followed by Robinson annulation with ethyl vinyl ketone gave 56 in 75% yield. After protection of an enone of 56 with ethylene glycol (93% yield), a methoxycarbonyl group of 57 was converted to a formyl group of 58 by reduction with LAH and subsequent Swern oxidation (67% yield). Transformation of a formyl group of 58 to an ethynyl group with Ohira reagent afforded 59 in 74% yield. Isoxazole 60 was prepared in 73% yield from 59 by deketalization under acidic conditions, followed by formylation with ethyl formate and subsequent isoxazole formation with hydroxylamine hydrochloride. The desired compound 10 was obtained by isoxazole cleavage of 60 with NaOMe, followed by addition of PhSeCl in the presence of pyridine and subsequent oxidation/elimination of the selenated intermediate with 30% aqueous H$_2$O$_2$ solution (82% yield).

Tricyclic ethynylcyanodienones 14 and 15, which have fluorene skeletons, were synthesized in 11 steps from 1-indanone (69) and 7-chloroindanone (76), respectively (Scheme 10). Unexpectedly, a previously reported method (Nguyen, P. et al. 2003) for conversion of 7-amino-1-indanone (74) to 76 using CuCl$_2$ and t-BuNO2 in CH$_3$CN gave 76 in much lower yield (15%) than the reported yield (64%) because N-(3-oxo-2,3-dihydro-1H-inden-4-yl)acetamide (75) was produced as a major product. However, we could obtain 76 in 86% yield by the traditional Sandmeyer reaction conditions (diazotization and subsequent chlorination with CuCl under acidic conditions). Methoxycarbonylation and subsequent Robinson annulation of 69 and 76 provided the known compound 70 (Nguyen, P. et al. 2003; Murakata, M. et al. 1999) and the new compound 77 in 60% and 45% yield, respectively. The ketal of fluorene 70 with diethylene glycol was easily converted to the original 70, while the ketal of phenanthrene 56 with ethylene glycol was stable (see Scheme 7). Enones 70 and 77 were protected with 2,3-butandiol to give 71 and 78, respectively. Ethynyl enones 73 and 80 were prepared via 72 and 79 from 71 and 78 in four steps (LAH reduction, Swern oxidation, ethynylation with Ohira reagent, and deprotection under acidic conditions), respectively. The desired compounds 14 and 15 were obtained in 61% and 45% yield from 73 and 80 in four steps (formylation, isoxazole formation, introduction of a cyano group and insertion of a double bond), respectively.

Example 4. Chemicl Reactivity as Michael Acceptors

Chemical reactivity of monocyclic, bicyclic, and tricyclic compounds 4-15 as Michael acceptors was evaluated using UV spectroscopy.

Michael reaction between ethynylcyanodienones with DTT give adducts IV (Scheme 11). Since adducts IV have different UV absorption spectra ($\lambda_{max}$ 330-380 nm) from those of the corresponding ethynylcyanodienones ($\lambda_{max}$ 230-320 nm), UV spectroscopy can clarify whether or not the Michael adducts are produced.[6]

Scheme 11

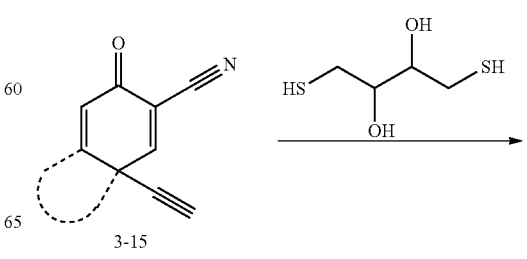

3-15

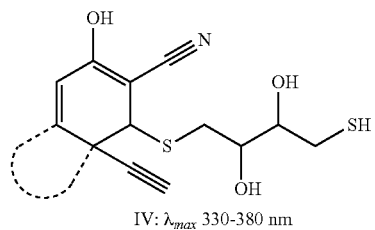

IV: λ_max 330-380 nm

Scheme 12.
Michael reaction between compound 4 and ten equivalents of DTT

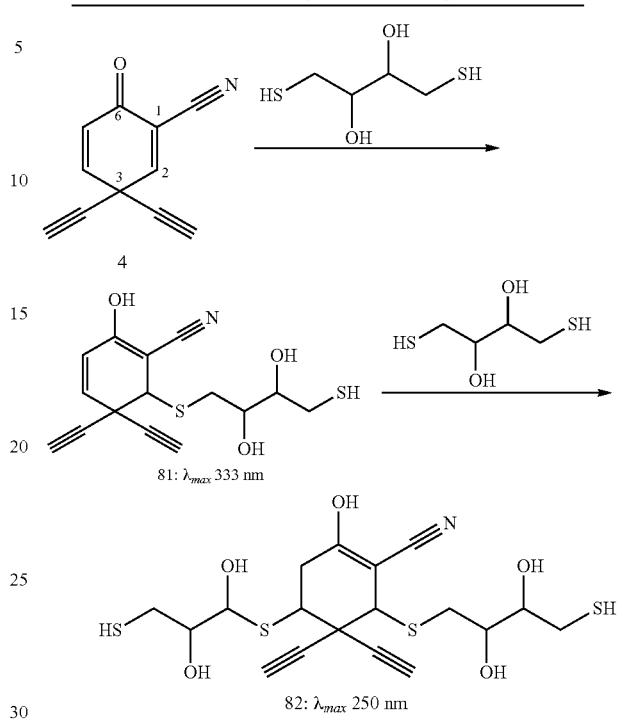

1. UV Studies on Monocyclic and Bicyclic Compounds 4-9 with DTT Compounds 5-8 with DTT gave similar UV spectra to those of 3 (Taylor, S. K. et al. 1988). Compounds 5-8 have local maximum absorptions at 332-338 nm upon the addition of DTT (1 and 10 equiv) under dilute (0.1 mM of the compounds) and neutral aqueous conditions (pH 7.4 phosphate buffered saline-1% ethanol containing 1 mM $KH_2PO_4$, 5.6 mM $Na_2HPO_4$, and 154 mM NaCl) (Table 1 and FIG. 2). Also, these compounds react with a chloride anion (a much weaker nucleophile than a sulfhydryl group of DTT), which is contained in the buffer solution, to give Michael adducts whose local maximum absorptions are observed at 320-326 nm.

We have calculated approximate equilibrium constants (K) of these Michael reactions in the solutions of 5-8 with DTT (each initial concentration, 0.1 mM. See the calculation of the equilibrium constants in the Supporting Information). The values of K are approximately $1.0$-$4.2 \times 10^3$ (L/mol), implying that these additions are very strongly favored.

Figures 2A, 2B, 2C, 2D, 2E, 2F, 2G, 2H:
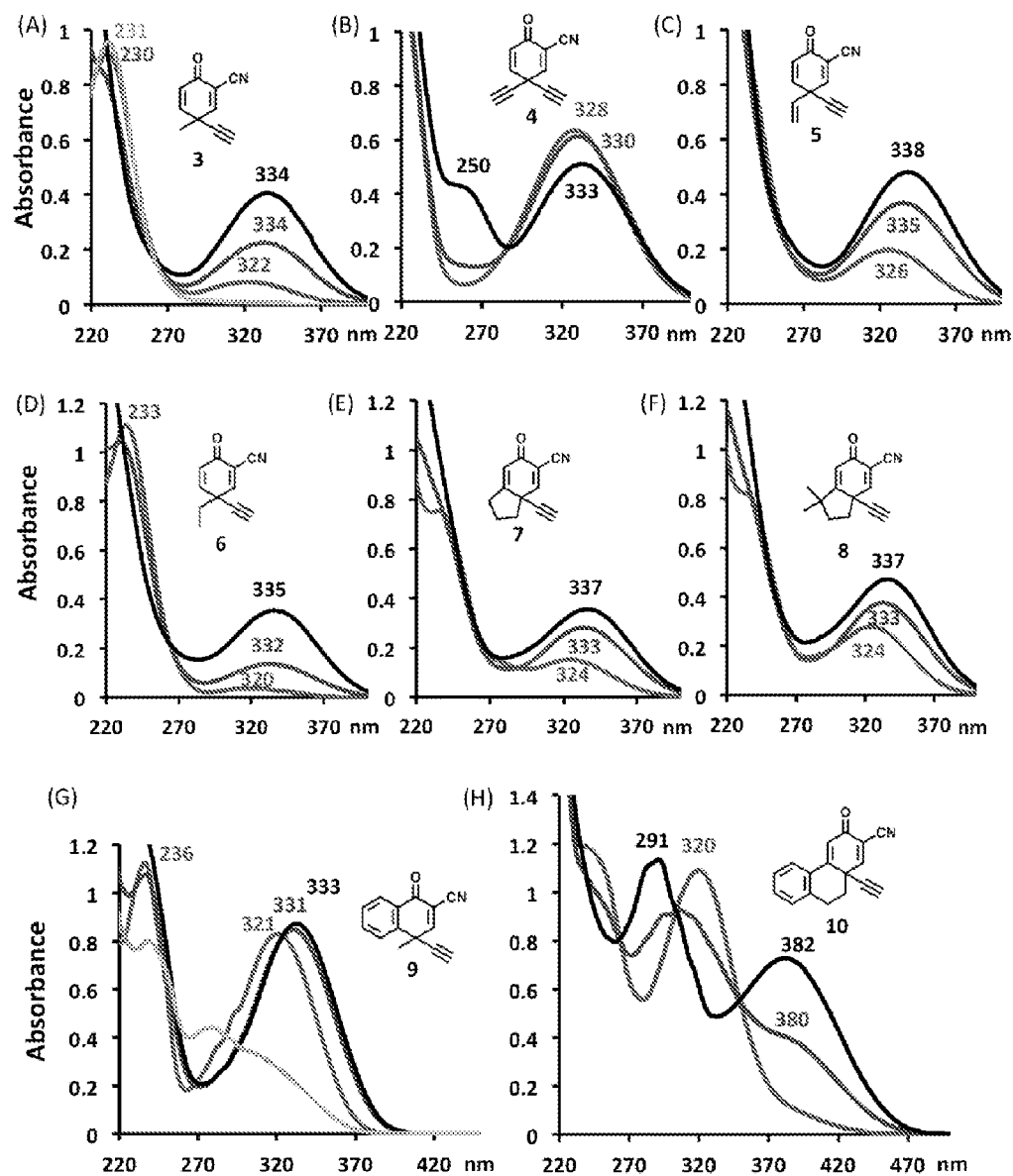
FIG. 2A: UV spectra of ethynylcyanodienones with DTT at rt. UV spectra of 0.1 mM ethynylcyanodienone in phosphate buffer saline-1% ethanol (pH 7.4) (red line, labeled 230 and 322) and the corresponding reaction mixtures with 0.1 mM DTT (blue line, lower line labeled 334) and 1 mM DTT (black line, upper line labeled 334). UV spectrum of 0.1 mM ethynylcyanodienone in water (light blue line, labeled 231).
FIG. 2B: UV spectra of 0.1 mM ethynylcyanodienone in phosphate buffer saline-1% ethanol (pH 7.4) (red line, labeled 328) and the corresponding reaction mixtures with 0.1 mM DTT (blue line, labeled 334) and 1 mM DTT (black line, labeled 250 and 333).
FIG. 2C: UV spectra of 0.1 mM ethynylcyanodienone in phosphate buffer saline-1% ethanol (pH 7.4) (red line, labeled 326) and the corresponding reaction mixtures with 0.1 mM DTT (blue line, labeled 335) and 1 mM DTT (black line, labeled 338).
FIG. 2D: UV spectra of 0.1 mM ethynylcyanodienone in phosphate buffer saline-1% ethanol (pH 7.4) (red line, labeled 233 and 320) and the corresponding reaction mixtures with 0.1 mM DTT (blue line, labeled 332) and 1 mM DTT (black line, labeled 335).
FIG. 2E: UV spectra of 0.1 mM ethynylcyanodienone in phosphate buffer saline-1% ethanol (pH 7.4) (red line, labeled 324) and the corresponding reaction mixtures with 0.1 mM DTT (blue line, labeled 333) and 1 mM DTT (black line, labeled 337).
FIG. 2F: UV spectra of 0.1 mM ethynylcyanodienone in phosphate buffer saline-1% ethanol (pH 7.4) (red line, labeled 324) and the corresponding reaction mixtures with 0.1 mM DTT (blue line, labeled 3343) and 1 mM DTT (black line, labeled 337).
FIG. 2G: UV spectra of 0.1 mM ethynylcyanodienone in phosphate buffer saline-1% ethanol (pH 7.4) (red line, labeld 236 and 321) and the corresponding reaction mixtures with 0.1 mM DTT (blue line, labeled 331) and 1 mM DTT (black line, labeled 333). UV spectrum of 0.1 mM ethynylcyanodienone in water (light blue line, unlabeled).
FIG. 2H: UV spectra of 0.1 mM ethynylcyanodienone in phosphate buffer saline-1% ethanol (pH 7.4) (red line, labeled 320) and the corresponding reaction mixtures with 0.1 mM DTT (blue line, labeled 380) and 1 mM DTT (black line, labeled 291 and 382).
Figures 2I, 2J, 2K, 2L:
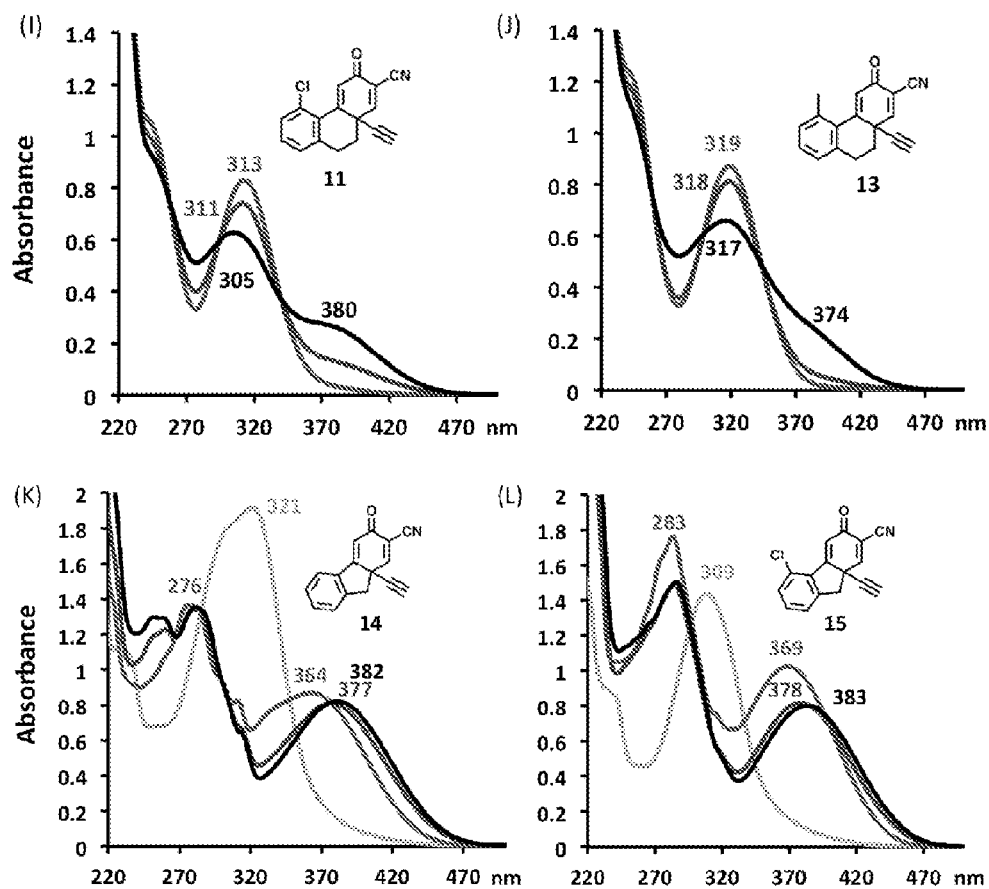
FIG. 2I: UV spectra of 0.1 mM ethynylcyanodienone in phosphate buffer saline-1% ethanol (pH 7.4) (red line, labeled 313) and the corresponding reaction mixtures with 0.1 mM DTT (blue line, labeled 311) and 1 mM DTT (black line, labeled 305 and 380).
FIG. 2J: UV spectra of 0.1 mM ethynylcyanodienone in phosphate buffer saline-1% ethanol (pH 7.4) (red line, labeled 319) and the corresponding reaction mixtures with 0.1 mM DTT (blue line, labeled 318) and 1 mM DTT (black line, labeled 317 and 374).
FIG. 2K: UV spectra of 0.1 mM ethynylcyanodienone in phosphate buffer saline-1% ethanol (pH 7.4) (red line, labeld 313) and the corresponding reaction mixtures with 0.1 mM OTT (blue line, labeled 311) and 1 mM DTT (black line, labeled 305 and 380). UV spectrum of 0.1 mM ethynylcyanodienone in water (light blue line, labeled 321).
FIG. 2L: UV spectra of 0.1 mM ethynylcyanodienone in phosphate buffer saline-1% ethanol (pH 7.4) (red line, labeld 283 and 369) and the corresponding reaction mixtures with 0.1 mM DTT (blue line, labeled 378) and 1 mM DTT (black line, labeled 383). UV spectrum of 0.1 mM ethynylcyanodienone in water (light blue line, labeled 309).

Compound 4 has two local maximum absorptions at 333 and 250 nm (absorbance (A)=0.510 and 0.439, Table 1 and FIG. 2) with 10 equiv of DTT. We have never observed such a spectrum with DTT. The wavelengths of the local maximum absorbance ($\lambda_{max}$) at 333 and 250 nm are assigned to those of 81 (cyanodiene) and 82 (cyanoenone), respectively (Scheme 12). Also, 4 reacts with a chloride anion to give a similar high concentration of the adduct to that of the adduct with DTT (1 equiv). Interestingly, these findings indicate that the two ethynyl groups at C3 increase the reactivity of both cyanoenone and enone without a cyano group. The approximate K of the Michael reactions of 4 with DTT (each initial concentration, 0.1 mM) is $10.6 \times 10^3$ (L/mol) and the value is much higher than those of 3 and 5-8. This means that the addition of 4 with DTT is much more favored than those of 3 and 5-8.

These K values demonstrate that the order of the reactivity as Michael acceptors is 4 (ethynyl group)>>8 (dimethylcyclopentane ring)≥5 (vinyl group)>7 (cyclopentane ring) >3 (methyl group)>6 (ethyl group). We have observed a tendency that electron-donating groups at C3 position decrease the reactivity. Again, notably, an ethynyl group, a moderate electron-withdrawing group, enhances the reactivity of enone without a cyano group. Importantly, the enolizable cyanodienone 7 is less reactive than the corresponding nonenolizable cyanodienone 8. The naphthalene derivative 9 also reacts with a chloride anion to give a similar high concentration of the adduct to those of the adducts with DTT (1 and 10 equiv). The reactivity of 9 is similar to that of 4.

2. UV Studies on Tricyclic Compounds 10-15 with DTT

Tricyclic compounds 10-15 react with DTT to give the adducts whose local maximum absorptions are observed at 374-383 nm range (Table 1 and FIG. 2). Interestingly, in this series, phenanthrene derivatives 10-13 are much less reactive than fluorene derivatives 14 and 15. Phenanthrene derivatives do not react with a chloride anion, while fluorene derivatives react with a chloride anion to give similar concentrations of the adducts to those of the adducts with DTT. Among phenanthrene derivatives, substitutents at C5 decrease the reactivity. Overall, UV spectra demonstrate that the order of the reactivity as Michael acceptors is 14 and 15 (fluorene)>>10 (phenanthrene)>11 (5-chlorophenanthrene)>13 (5-methylphenanthrene).

Example 5. Biological Activity

1. Compounds 4-15 induce NQO1 in Hepa1c1c7 Murine Hepatoma Cells.

Figure 3:
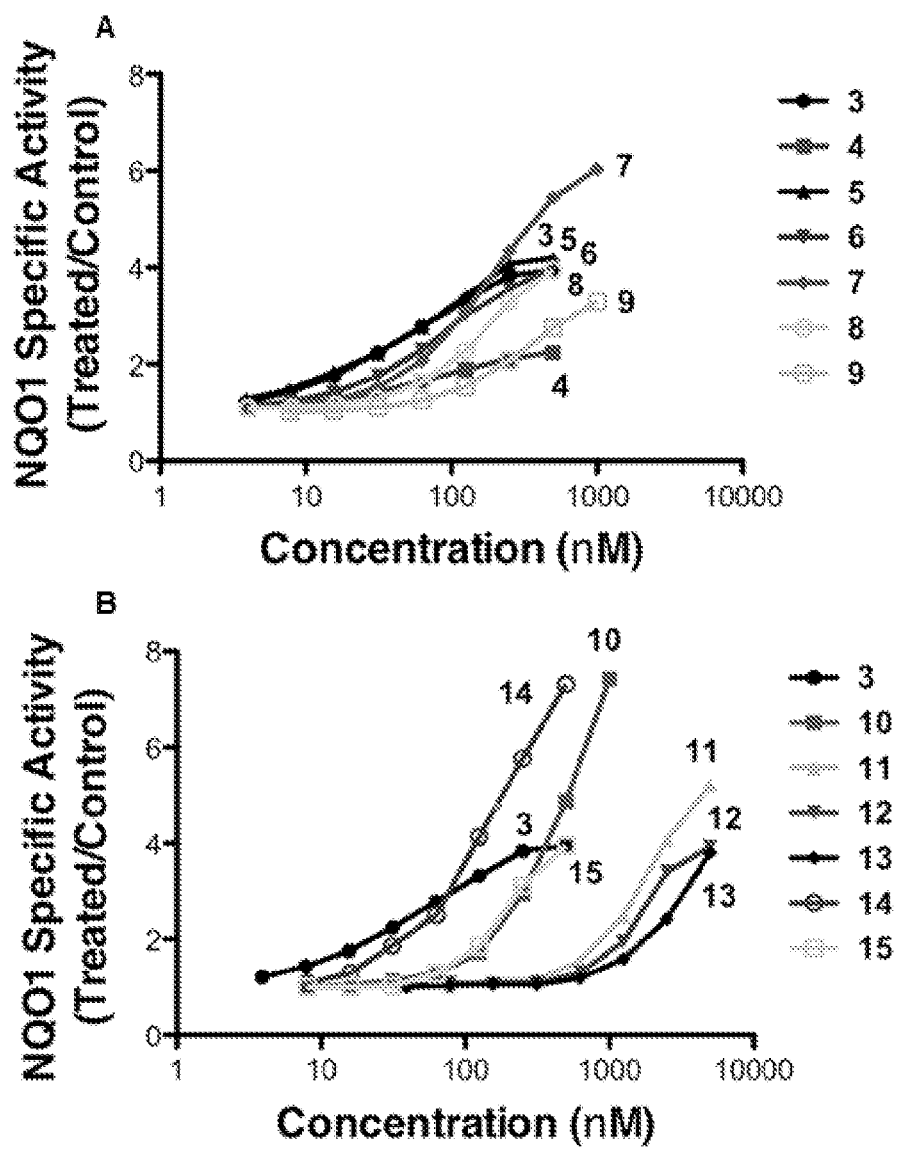
FIG. 3A: Compounds 3, 4, 5, 6, 7, 8 and 9 tested in NQO1 Specific Activity assay.
FIG. 3B: Compounds 3, 10, 11, 12, 13, 14 and 15 tested in NQO1 Specific Activity assay.

To determine the ability to activate the Keap1/Nrf2/ARE pathway, compounds 4-15 were evaluated for the induction of the classical Nrf2 target, the phase 2 cytoprotective enzyme NQO1 in Hepa1c1c7 murine hepatoma cells (Prochaska, H. J. & Santamaria, A. B. 1988; Fahey, J. W. et al. 2004). In this assay, the concentration required to double (CD value) the specific enzyme activity of NQO1 is used to quantify inducer potency. The CD values (nM) of 3-15, TBE-31, and CDDO are shown in Table 1. The CD values of these compounds are observed in the 20-2000 nM concentration range. Notably, most of these compounds are more potent than sulforaphane (Zhang, Y. et al. 1992), which is a widely used activator of the Keap1/Nrf2/ARE pathway and has demonstrated protective effects in many disease models related to inflammation and cancer (Zhang, Y. et al. 1992; Dinkova-KOstova, A. T. et al. 2012). Among these compounds, 5 is the most potent and the potency is similar to that of 3. Compounds 6 and 14 are next in the rank order of potency. Interestingly, bicyclic compound 7 and tricyclic compounds 10, 11, and 14 induce NQO1 more effectively than monocyclic compounds 3-6 at the higher concentrations (FIG. 3) although these compounds are less potent than the monocyclic compounds according to the CD values. These compounds may be more robust inducers than monocyclic compounds.

As previously reported (Zheng, S. et al. 2012), a correlation was found between reactivity of monocyclic cyanoenones as Michael acceptors and biological potency. In this series of monocyclic and bicyclic compounds 3-9, we found a similar correlation. Compounds 4 and 9, which have the highest reactivity with a sulfhydryl group and a chloride anion in this series, and compound 8, which has the third highest reactivity, are less potent than other compounds which have much lower reactivity with a chloride anion than 4, 8 and 9. Based on these results, it is proposed that: (i) due to its exceedingly high chemical reactivity, a large portion of 4, 8 and 9 could be "quenched" by abundant cellular thiols, such as the cysteine residue of glutathione, which is present at millimolar concentrations; (ii) 4, 8 and 9 could be inactivated by chloride anion in the cell culture medium used for biological testing and/or (iii) in addition to the chemical reactivity, other factors such as cellular uptake and export mechanisms may play a role in determining the biological potency. Among the compounds whose reactivity with a chloride anion is relatively low, interestingly, compound 5 which has the highest reactivity with a sulfhydryl group is the most biologically potent.

On the other hand, a series of tricyclic compounds having phenanthrene and fluorene skeletons, 10-15, show a different correlation between reactivity and potency. The fluorene derivatives 14 and 15 are more potent than the phenanthrene derivatives 10-13, while 14 and 15 show much higher reactivity with a chloride anion and a sulfhydryl group than 10, 11, and 13. Notably, amongst these monocyclic, bicyclic, and tricyclic compounds 3-15, 14 shows not only the third lowest CD value but also induces NQO1 to a greater magnitude than 3 and 5 at higher concentrations. In a series of phenanthrene derivatives, the potency is well correlated to the reactivity.

2. Compounds 4-15 inhibit NO Production Induced by LPS Stimulation in RAW 264.7 Cells.

The inhibitory activities of 3-15 on NO production was evaluated in

RAW 264.7 cells stimulated with LPS (Suh, N. et al. 1998). The inhibitory activities [$IC_{50}$ (nM) values] of 3-15, TBE-31, and CDDO are shown in Table 1. Among these new compounds, 5 has the highest potency, which is similar to that of 3. Notably, both 3 and 5, which are monocyclic compounds, are as potent as or even slightly more potent than a pentacyclic tritepenenoid, CDDO.

Figure 4:
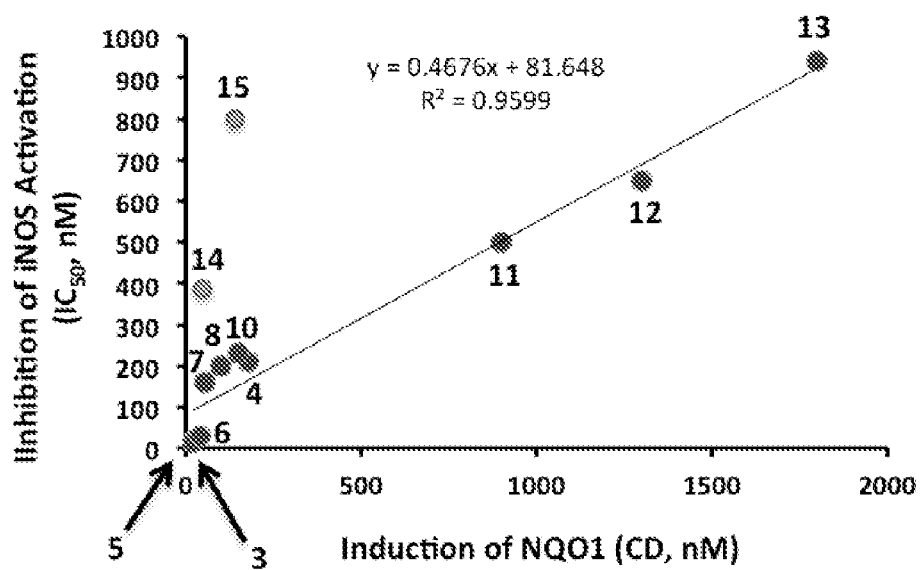
FIG. 4: Correlation of potencies of ethynylcyanodienones 3-8, 10-13, (as shown in blue circle) and 14-15 (shown as orange circles) as inducers of NQO1 in Hepa1c1c7 murine hepatoma cells, expressed as CD values, and for suppression of iNOS induction by LPS in RAW 264.7 cells, expressed as $IC_{50}$ values. The linear correlation coefficient for the blue circles is $r^2=0.96$.

We previously demonstrated a linear correlation between NQO1 inducer potency (CD) and inhibitory activity against NO production ($IC_{50}$) of semisynthestic triterpenoids (Dinkova-Kostova, A. et al. 2005; Honda, T. et al. 2011) and synthetic tricyclic compound (Honda, T. et al. 2007). However, we did not observe a linear correlation in monocyclic cyanoenones which have been previously reported, although there was a general correlation between the rank order of potencies in the two assays (Zheng, S. et al. 2012. Remarkably, in this series of compounds 3-13, we observed an even more striking linear correlation ($r^2$=0.96) than the previous reported correlations ($r^2$=0.91) (FIG. 4) (Dinkova-Kostova, A. et al. 2005). Interestingly, the fluorene derivatives 14 and 15 are not correlated to this line. While 14 has high potency in the NQO1 induction assay, 14 shows only moderate inhibitory activity in the iNOS assay.

TABLE 1

UV spectra$^a$ & biological potency of ethynylcyanodienones 3-15

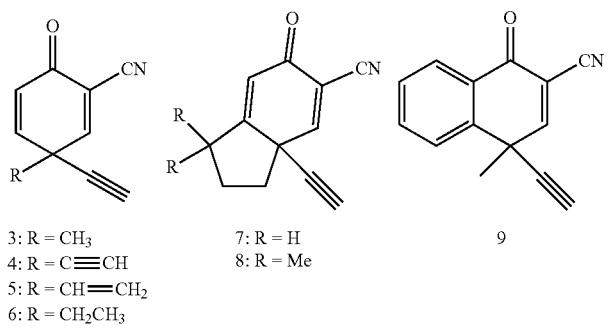

3: R = CH$_3$
4: R = C≡CH
5: R = CH=CH$_2$
6: R = CH$_2$CH$_3$

7: R = H
8: R = Me

9

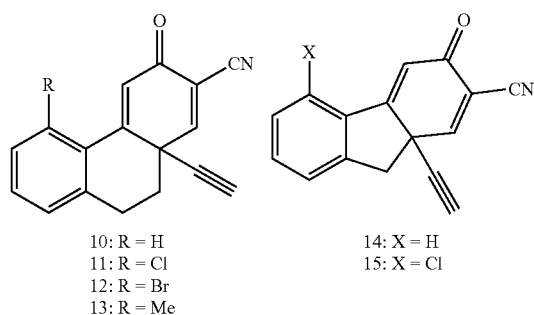

10: R = H
11: R = Cl
12: R = Br
13: R = Me

14: X = H
15: X = Cl

TABLE 1-continued

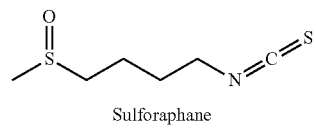

Sulforaphane

| Compd | With DTT (10 equiv) | | With DTT (1 equiv) | | Without DTT[b] (With Cl−) | | K[c] ×10³ L/mol | NQO1[h] CD (nM) | iNOS[i] IC₅₀ (nM) |
|---|---|---|---|---|---|---|---|---|---|
| | $\lambda_{max}$ (nm) | A[d] | $\lambda_{max}$ (nm) | A[d] | $\lambda_{max}$ (nm) | A[d] | | | |
| 3[e] | 334 | 0.406 | 334 | 0.227 | 322 | 0.083 | 2.0 | 21 | 18 |
| 4 | 333 | 0.510 | 330 | 0.614 | 328 | 0.635 | 10.6 | 180 | 210 |
|  | 250 | 0.439 |  |  |  |  |  |  |  |
| 5 | 338 | 0.481 | 335 | 0.369 | 326 | 0.197 | 4.0 | 20 | 16 |
| 6 | 335 | 0.353 | 332 | 0.135 | 320 | 0.036 | 1.0 | 42 | 29 |
| 7 | 337 | 0.355 | 333 | 0.281 | 324 | 0.151 | 2.7 | 56 | 160 |
| 8 | 337 | 0.472 | 333 | 0.376 | 324 | 0.279 | 4.2 | 100 | 200 |
| 9 | 333 | 0.872 | 331 | 0.848 | 321 | 0.831 | NT[g] | 220 | NT |
| 10 | 382 | 0.723 | 380 | shoulder | — | — | NT[g] | 150 | 230 |
| 11 | 380 | 0.262 | 380 | shoulder | — | — | NT[g] | 900 | 500 |
| 12 | NT[f] | | NT[f] | | NT[f] | | NT[g] | 1300 | 650 |
| 13 | 374 | 0.279 | — | — | — | — | NT[g] | 1800 | 940 |
| 14 | 382 | 0.820 | 377 | 0.808 | 364 | 0.867 | NT[g] | 41 | 480 |
| 15 | 383 | 0.803 | 378 | 0.819 | 369 | 1.025 | NT[g] | 130 | 800 |
| TBE-31 (1) | | | | | | | | 0.9 | 1.0 |
| CDDO | | | | | | | | 2.3 | 23 |
| Sulforaphane | | | | | | | | 200 | 400 |

[a]UV spectra of the Michael adducts between ethynylcyanodienones (0.1 mM) and DTT (1 mM and 0.1 mM) in phosphate buffer saline-1% ethanol (pH 7.4) at rt. The full UV spectra of the reaction mixtures are shown in FIG. 2.
[b]Some ethynylcyanodienones gave Michael adducts with Cl− in phosphate buffer saline-1% ethanol (pH 7.4).
[c]Equilibrium constant at 0.1 mM of compound with 0.1 mM of DTT.
[d]A: absorbance
[e]See reference Zheng, S. et al. 2012.
[f]Not observed. Compound 12 was not soluble in phosphate buffer saline-1% ethanol (pH 7.4).
[g]Not calculated.
[h]Hepa1c1c7 cells (10,000 per well) were grown in 96-well plates for 24 h and then treated with increasing concentrations of compounds for 48 h. Cells were lysed and the protein concentration of the lysates was determined by the bicinchoninic acid (BCA) assay (Thermo Scientific). The concentration required to double (CD) the specific enzyme activity of NQO1 was used to quantity inducer potency. The value is based on the activity from eight replicate wells at each concentration. The standard deviation in each case was between 5 and 10%.
[i]RAW 264.7 cells (20,000 per well) were grown in 96-well plates for 24 h. Cells were then co-treated with LPS (10 ng/mL) and increasing concentrations of compounds for a further 48 h. The concentration of NO in the cell culture medium was determined using the Griess reagent. The cells were lysed and the protein concentration of the lysates was determined by the BCA assa. IC₅₀ values were determined based on suppression of LPS-induced NO production normalized to the protein concentration. The value is based on determinations from eight replicate wells at each concentration. Results shown are the average of three independent experiments.

Example 6. Additional Analogs

An additional aspect of the invention provides derivatvies of compounds 4-15 that are also Keap1/Nrf2/ARE activators, NQO1 inducers and/or iNOS inhibitors. These derivatives have analogous activity to any one of compounds 4-15.

Example 7. Diseases Implicated by Keap1/Nrf2/ARE Pathway, Overexpression of COX-2 and/or Overexpression of iNOS An amount of the compound of the present invention is administered to a subject afflicted with cancer. The amount of the compound is effective to treat the subject by inhibiting growth of the cancer cells, killing the cancer cells and/or inducing apoptosis in the cancer cells.

An amount of the compound of the present invention is administered to a subject afflicted with an inflammatory disease. The amount of the compound is effective to treat the subject.

An amount of the compound of the present invention is administered to a subject afflicted with a cardiovascular disease. The amount of the compound is effective to treat the subject.

An amount of the compound of the present invention is administered to a subject afflicted with a neurodegenerative disease. The amount of the compound is effective to treat the subject.

An amount of the compound of the present invention is administered to a subject afflicted with renal or kidney disease. The amount of the compound is effective to treat the subject.

An amount of the compound of the present invention is administered to a subject afflicted with a disease characterized by the overexperession of COX-2. The amount of the compound is effective to treat the subject.

An amount of the compound of the present invention is administered to a subject afflicted with a disease characterized by the overexperession iNOS genes. The amount of the compound is effective to treat the subject.

Discussion

In order to explore reversible covalent drugs, new monocyclic, bicyclic, and tricyclic ethynylcyanodienones 4-15 were synthesized, and biologically evaluated, containing 3 as the electrophilic fragment. The designed compounds have been synthesized in relatively few steps and good yields from the starting materials, respectively. Diels-Alder reaction and Robinson annulation were employed for the key cyclization steps of these syntheses.

It was speculated that 1 regulates proteins affecting inflammation, oxidative stress, differentiation, apoptosis, and proliferation, including Keap1, IKKJ3, and JAK1, to name a few, by reversible Michael addition between the cyanoenone functionalities and the sulfhydryl groups of cysteine moieties on these proteins. We focused on these monocyclic cyanoenones, which are considered to be the phamacophores of 1. A preliminary set of eight monocylic cyanoenones including 2 and 3 were prepared, and then, evaluated the chemical reactivity as Michael acceptors and biological potency (Zheng, S. et al. 2012). Amongst monocyclic cyanoenones, ethynylcyanodienone 3 is a highly reactive Michael acceptor with thiol nucleophiles. Furthermore an important feature of 3 is that its Michael addition is reversible. For the induction of NQO1, 3 demonstrates the considerable potency (Zheng, S. et al. 2012). For the inhibition of nitric oxide (NO) production in RAW264.7 cells (murine macrophage-like cell line) stimulated with IFN-γ, 3 also shows the strong potency (Zheng, S. et al. 2012). Remarkably, in this assay, ethynylcyanodienone 3, which has such a simple structure, is about three times more potent than a pentacyclic triterpenoid, CDDO, whose methyl ester (bardoxolone methyl) is presently being evaluated in phase 2 clinical trials for the treatment of pulmonary arterial hypertension (PAH) in the United States and diabetic nephropathy in Japan.

Figure 5:
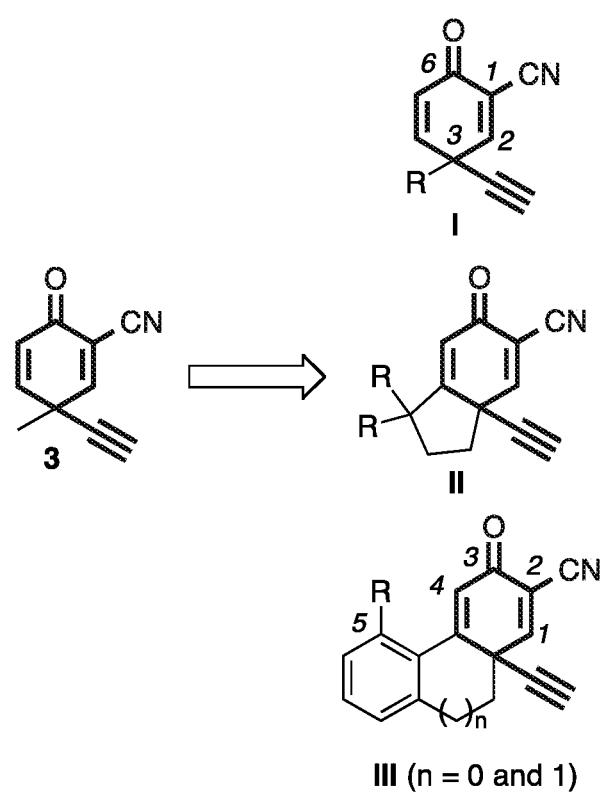
FIG. 5: Monocyclic, bicyclic, and tricyclic compounds I-III were designed and synthesized containing 3 as the electrophilic fragment

Ethynylcyanodienone 3 is considered to be a useful fragment for exploring reversible covalent drugs which are targeting on the Keap1/Nrf2/ARE pathway. Thus, new monocyclic, bicyclic, and tricyclic compounds I-III (see FIG. 5) were designed and synthesized containing 3 as the electrophilic fragment (FIG. 5, specifically Table 1). Then, the reactivity of ethynylcyanodienone moiety as a Michael acceptor was measured in these compounds by UV spectroscopy and evaluated their potency for the induction of NQO1 in Hepa1c1c murine hepatoma cells and for the inhibition of iNOS in RAW264.7 cells stimulated with LPS.

In this series of monocyclic, bicyclic, and tricyclic compounds excluding a fluorene derivative 14, biological potency of the compounds, which have high reactivity with a chloride anion, are weak as inducers of NQO1 and as inhibitors of iNOS. The compounds, which have low reactivity with a chloride anion but high reactivity with a sulfhydryl group, are highly potent as the inducers and the inhibitors. A monocyclic compound 5 is the most potent among them and is as potent as the electrophilic fragment 3. Exceptionally, while 14 has high reactivity with a chloride anion, 14 has high potency as the inducer of NQO1. However, potency of 14 as the inhibitor of iNOS is weak.

Notably, a striking linear correlation ($r^2=0.96$) was observed between the potency of the compounds 3-13 as inducers of NQO1 (CD values) and as inhibitors of iNOS ($IC_{50}$ values), but compounds 14 and 15 do not fit this line. As the iNOS inhibitory activity is only partially dependent on Nrf2 (Liu, H. et al. 2008), this finding suggests that 14 and 15 may be more specific as Nrf2 activators than as iNOS inhibitors. Although the potency of 14 is lower than that of 3 and 5 according to the CD values, the magnitude of NQO1 induction by 14 is greater than that by 3 and 5 at concentrations higher than the CD values. Thus, 14 may be a more robust inducer than 3 and 5. Overall, interestingly and notably, 14 is clearly different from the other compounds in this series.

Compound 5 is as potent in the NQO1 induction assay and the iNOS inhibition assay. Compound 14 has improved properties relative to compound 3 because it is more specific as a NQO1 inducer than as an iNOS inhibitor. Although the potency of 14 as a NQO1 inducer is lower than that of 3 and 5 according to the CD values, because the magnitude of NQO1 induction by 14 is greater than that by 3 and 5 at concentrations higher than the CD values, 14 is a more robust NQO1 inducer than 3 and 5. Additional polycyclic compounds disclosed hereinhave improved properties similar to compound 14.

In summary, compounds containing the fragment 3 maintain or improve the features of the reactivity and biological potency of 3.

REFERENCES

Brown, D. S.; Marples, B. A.; Smith, P.; Walton, L.; Epoxidation with dioxiranes derived from 2-fluoro-2-substituted-1-tetralones and 1-indanones. Tetrahedron 1995, 51, 3587-3606.

Clinton, R. O.; Manson, A. J.; Stonner, F. W.; Neumann, H. C.; Christiansen, R. G.; Clarke, R. L.; Ackerman, J. H.; Page, D. F.; Dean, J. W.; Dickinson W. B.; Carabateas, C. Steroidal[3,2-c]pyrazoles. II. Androstanes, 19-norandrostanes and their unsaturated analogs. J. Am. Chem. Soc. 1961, 83, 1478-1491.

Corey, E. J.; Ruden, R. A. Stereoselective methods for the synthesis of terminal cis and trans enyne units. Tetrahedron Lett. 1973, 1495-1499.

Dinkova-Kostova, A. T.; Liby, K. T.; Stephenson, K. K.; Holtzclaw, W. D.; Gao, X.; Suh, N.; Williams, C.; Risingsong, R.; Honda, T.; Gribble, G. W.; Sporn, M. B., Talalay, P. Extremely potent triterpenoid inducers of the phase 2 response: correlations of protection against oxidant and inflammatory stress. Proc. Natl. Acad. Sci. USA 2005, 102, 4584-4589.

Dinkova-Kostova, A. T.; Talalay, P.; Sharkey, J.; Zhang, Y.; Holtzclaw, W. D.; Xiu Jun Wang, X. J.; David, E.; Schiavoni, K. H.; Finlayson, S.; Dale F. Mierke, D. F.; Honda, T. An exceptionally potent inducer of cytoprotective enzymes: elucidation of the structural features that determine inducer potency and reactivity with Keap1. J. Biol. Chem. 2010, 285, 33747-33755.

Dinkova-Kostova, A. T.; Kostov R. V. Glucosinolates and isothiocyanates in health and disease. Trends Mol. Med. 2012, 18, 337-347.

Fahey, J. W.; Dinkova-Kostova, A. T.; Stephenson, K. K.; Talalay, P. The "Prochaska" microtiter plate bioassay for inducers of NQO1. Methods Enzymol. 2004, 382, 243-258.

Fearnley, S. P.; Funk, R. L.; Gregg, R. Preparation of 2-alkyl- and 2-acylpropenals from 5-(trifluoromethanesulfonyloxy)-4H-1,3-dioxin: A versatile acrolein a-cation synthon. Tetrahedron 2000, 56, 10275-10281.

Gold, R.; Kappos, L.; Arnold, D. L.; Bar-Or, A.; Giovannoni, G.; Selmaj, K.; Tornatore, C.; Sweetser, M. T.; Yang, M.; Sheikh, S. I.; Dawson, K. T. Placebo-controlled phase 3 study of oral BG-12 for relapsing multiple sclerosis. N. Engl. J. Med. 2012, 367, 1098-1107.

Honda, T.; Sundararajan, C.; Yoshizawa, H.; Su, X.; Honda, Y.; Liby, K. T.; Sporn, M. B.; Gribble, G. W. Novel tricyclic compounds having acetylene groups at C8a and cyano enones in rings A and C: Highly potent anti-inflammatory and cytoprotective agents. J. Med. Chem. 2007, 50, 1731-1734.

Honda, T.; Yoshizawa, H.; Sundararajan, C.; David, E.; Lajoie, M. j.; Favaloro, F. G. Jr.; Janosik, T.; Su, X.; Honda, Y.; Roebuck, B. D.; Gribble, G. W. Tricyclic compounds containing non-enolizable cyano enones. A novel class of highly potent anti-inflammatory and cytoprotective agents. J. Med. Chem. 2011, 54, 1762-1778.

Honda, T; Dinkova-Kostova, A. T.; David, E.; Padegimas, E. M.; Sundararajan, C.; Visnick, M.; Bumeister, R.; Wigley, W. C. Synthesis and biological evaluation of 1-[2-Cyano- 3,12-dioxooleana-1,9(11)-Bien-28-oyl]-4-ethynylimidazole. A novel and highly potent anti-inflammatory and cytoprotective agent. Bioorg. Med. Chem. Lett. 2011, 21, 2188-2191.

Hulme, A. N.; Meyers, A. I. Asymmetric synthesis of 1,1-disubstituted tetralins and dihydronaphthalenes by diastereoselective addition of lithiosilanes to chiral naphthalenes. *J. Org. Chem.* 1994, 59, 952-953.

Johnson, W. S.; Shelberg, W. E. A plan for distinguishing between some five- and six-membered ring ketones. J. Am. Chem. Soc. 1945, 67, 1745-1754.

Justribó, V.; Pellegrinet, S. C.; Colombo, M. I. Studies on the intramolecular cyclizations of bicyclic 6-hydroxynitriles promoted by triflic anhydride. *J. Org. Chem.* 2007, 72, 3702-3712.

Kahne, D.; Collum, D. B. Kinetic cyanations of ketone enolates. Tetrahedron Lett. 1981, 22, 5011-5014.

Kalra, S.; Knatko, E. V.; Zhang, Y.; Honda, T.; Yamamoto, Y.; Dinkova-Kostova A. T. Highly potent activation of Nrf2 by topical tricyclic bis(cyano enone): implications for protection against UV radiation during thiopurine therapy. Cancer Prev. Res. 2012, 5, 973-981.

Liby, K.; Yore, M. M.; Roebuck B. D.; Baumgartner, K. J.; Honda, T.; Sundararajan, C.; Yoshizawa, H.; Gribble, G. W.; Williams, C. R.; Risingsong, R.; Royce, D. B.; Dinkova-Kostova, A. T.; Stephenson, K. K.; Egner, P. A.; Yates, M. S.; Groopman, J. D.; Kensler, T. W.; Sporn, M. B. A novel acetylenic tricyclic bis-(cyano enone) potently induces phase 2 cytoprotective pathways and blocks liver carcinogenesis induced by aflatoxin. Cancer Res. 2008, 68, 6727-6732.

Liotta, D.; Barnum, C.; Puleo, R.; Zima, G.; Bayer, C.; Kezar, H. S. III. A simple method for the efficient synthesis of unsaturated β-dicarbonyl compounds. J. Org. Chem. 1981, 46, 2920-2923.

Liu, H.; Dinkova-Kostova. A. T.; Talalay, P. Coordinate regulation of enzyme markers for inflammation and for protection against oxidants and electrophiles. *Proc. Natl. Acad. Sci. USA* 2008, 105, 15926-15931.

Mella, M.; Panza, L.; Ronchetti, F.; Toma, L. 1,2-Dideoxy-3,4:5,7-bis-O-(1-methylethylidene)-D-gluco- and D-galacto-hept-1-ynitols: synthesis and conformational studies. Tetrahedron 1988, 44, 1673-1678.

Miller, R. A.; Paavilainen, V. O.; Krishnan, S.; Serafimova, I. M.; Taunton, J. Electrophilic fragment-based design of reversible covalent kinase inhibitors. J. Am. Chem. Soc. 2013, 135, 5298-5301.

Murakata, M.; Mizuno, Y.; Yamaguchi, H.; Hoshino, O. Synthesis of (R)-(−)-3-methoxymethyl-3-propyl-3,4-dihydrocoumarin from a chiral Michael adduct: Absolute configuration of the allylated products of enatioselective radical-mediated reactions. Chem. Pharm. Bull. 1999, 47, 1380-1383.

Muzart J. Synthesis of unsaturated carbonyl compounds via a chromium-mediated allylic oxidation by 70% tert-butylhydroperoxide. Tetrahedron Lett. 1987, 28, 4665-4668.

Nareddy, P.; Mantilli, L.; Guenee, L.; Mazet, C. Atropoisomeric (P,N) ligands for the highly enantioselective Pd-catalysed intramolecular asymmetric a-arylation of a-branched aldehydes. *Angew. Chem. Int. Ed.* 2012, 51, 3826-3831.

Nguyen, P.; Corpuz, E.; Heidelbaugh, T. M.; Chow, K.; Garst, M. E. A convenient synthesis of 7-halo-indanones and 8-halo-1-tetralones. *J. Org. Chem.* 2003, 68, 10195-10198.

Nguyen, H. N.; Huang, X.; Buchwald, S. L. The first general palladium catalyst for the Suzuki-Miyaura and carbonyl enolate coupling of aryl arenesulfonates. *J. Am. Chem. Soc.* 2003, 125, 11818-11819.

Noji, M.; Sunahara, H.; Tsuchiya, K.; Mukai, T.; Komasaka, A.; Ishii, K. A novel synthetic route of 2-arylalkanoic acids by a ruthenium-catalysed chemoselective oxidation of furan rings. Synthesis, 2008, 3835-3845.

Ohira, S. Methanolysis of dimethyl (1-diazo-2-oxopropyl) phosphonate: Generation of dimethyl(diazomethyl)phosphonate and reaction with carbonyl compounds. *Synth. Commun.* 1989, 19, 561.

Prochaska, H. J.; Santamaria, A. B. Direct measurement of NAD(P)H:quinone reductase from cells cultured in microtiter wells: a screening assay for anticarcinogenic enzyme inducers. Anal. Biochem. 1988, 169, 328-336.

Shirakawa, S.; Shimizu, S. Hydrogen-bond-promoted C—C bond-forming reaction: Catalyst-free Michael addition reactions in ethanol. *Synlett* 2007, 3160-3164.

Suh, N.; Honda, T.; Finlay, H. J.; Barchowsky, A.; Williams, C.; Benoit, N. E.; Xie, Q. W.; Nathan, C.; Gribble, G. W.; Sporn, M. B. Novel triterpenoids suppress inducible nitric oxide synthase (iNOS) and inducible cyclooxygenase (COX-2) in mouse macrophages. Cancer Res. 1998, 58, 717-723.

Taylor, S. K.; Blackespoor, C. L.; Harvey, S. M.; Richardson, L. J. Friedel-Crafts cyclialkylations of some epoxides. 3. Cyclizations of tertiary and meta-substituted arylalkyl epoxides. *J. Org. Chem.* 1988, 53, 3309-3312.

Vedejs, E.; Daugulis, 0.; Harper, L. A.; MacKay, J. A.; Powell, D. R. A comparison of monocyclic and bicyclic phospholanes as acyl-transfer catalysts. *J. Org. Chem.* 2003, 68, 5020-5027.

Walker, S. D.; Barder, T. E.; Martinelli, J. R.; Buchwald, S. L. A rationally designed universal catalyst for Suzuki-Miyaura coupling processes. Angew. Chem. Int. Ed. 2004, 43, 1871-1876.

Zhang Y, Talalay P, Cho C. G., Posner G. H. A major inducer of anticarcinogenic protective enzymes from broccoli: isolation and elucidation of structure. Proc. Natl. Acad. Sci. USA, 1992, 89, 2399-2403.

Zheng, S; Laxmi, Y. R. S.; David, E; Dinkova-Kostova, A. T.; Katherine H. Shiavoni, K. H.; Ren, Y.; Zheng, Y.; Trevino, I.; Bumeister, R.; Ojima, I.; Wigley, W. C.; James J. B.; Mierke, D. F.; Honda, T. Synthesis, chemical reactivity as Michael acceptors, and biological potency of monocyclic cyanoenones, novel and highly potent anti-inflammatory and cytoprotective agents. J. Med. Chem. 2012, 55, 4837-4846.

Zheng, S.; Chowdhury, A.; Ojima, I.; Honda, T. Microwave-assisted Diels-Alder reactions between Danishefsky's diene and derivatives of ethyl α-(hydroxymethyl)acrylate. Synthetic approach towards a biotinylated anti-inflammatory monocyclic cyanoenone. Tetrahedron 2013, 69, 2052-2055.

What is claimed is:
1. A compound having the structure:

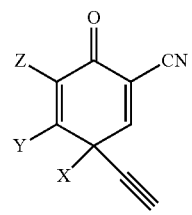

wherein
X is $C_1$-$C_{12}$ alkyl, $C_2$-$C_{12}$ alkenyl, $C_2$-$C_{12}$ alkynyl, cyano, aryl, heteroaryl, alkylaryl, alkylheteroaryl, alkenylaryl, alkenylheteroaryl, alkynylaryl, alkynylheteroaryl, alkoxy, alkenyloxy, alkynyloxy, aryloxy, heteroaryloxy, acyl, alkylhydroxy, alkylamino, alkenylamino, alkynylamino, amido, carboxyl, or carboxyl ester, or forms an unsubstituted or substituted indane or tetralin with Y, Y is H or forms an unsubstituted or substituted indane or tetralin with X, or forms an unsubstituted or substituted monocycle with Z; and Z is H or forms an unsubstituted or substituted monocycle with Y,
wherein when Z and Y are both H, then X is $C_2$ alkenyl or $C_2$ alkynyl,
or a salt or ester thereof.

2. The compound of claim 1, wherein
X is $C_1$-$C_{12}$ alkyl, $C_2$-$C_{12}$ alkenyl, $C_2$-$C_{12}$ alkynyl, cyano, aryl, heteroaryl, alkylaryl, alkylheteroaryl, alkenylaryl, alkenylheteroaryl, alkynylaryl, alkynylheteroaryl, alkoxy, alkenyloxy, alkynyloxy, aryloxy, heteroaryloxy, acyl, alkylhydroxy, alkylamino, alkenylamino, alkynylamino, amido, carboxyl, or carboxyl ester, or forms an unsubstituted or substituted indane or tetralin with Y, Y is H or forms an unsubstituted or substituted indane or tetralin with X; and Z is H
wherein when Z and Y are both H, then X is $C_2$ alkenyl or $C_2$ alkynyl,
or a salt or ester thereof.

3. The compound of claim 1, wherein
X is $C_1$-$C_{12}$ alkyl, $C_2$-$C_{12}$ alkenyl, $C_2$-$C_{12}$ alkynyl, cyano, aryl, heteroaryl, alkylaryl, alkylheteroaryl, alkenylaryl, alkenylheteroaryl, alkynylaryl, alkynylheteroaryl, alkoxy, alkenyloxy, alkynyloxy, aryloxy, heteroaryloxy, acyl, alkylhydroxy, alkylamino, alkenylamino, alkynylamino, amido, carboxyl, or carboxyl ester, Y is H or forms an unsubstituted or substituted monocycle with Z; and Z is H or forms an unsubstituted or substituted monocycle with Y,
wherein when Z and Y are both H, then X is $C_2$ alkenyl or $C_2$ alkynyl,
or a salt or ester thereof.

4. The compound of claim 1, wherein
X is $C_1$-$C_{12}$ alkyl, $C_2$-$C_{12}$ alkenyl, $C_2$-$C_{12}$ alkynyl, cyano, aryl, heteroaryl, alkylaryl, alkylheteroaryl, alkenylaryl, alkenylheteroaryl, alkynylaryl, alkynylheteroaryl, alkoxy, alkenyloxy, alkynyloxy, aryloxy, heteroaryloxy, acyl, alkylhydroxy, alkylamino, alkenylamino, alkynylamino, amido, carboxyl, or carboxyl ester, Y forms an unsubstituted or substituted monocycle with Z; and Z forms an unsubstituted or substituted monocycle with Y,
or a salt or ester thereof.

5. The compound of claim 1 having the structure:

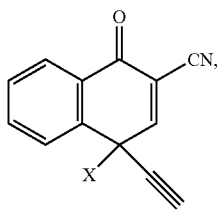

wherein X is $C_1$-$C_{12}$ alkyl, $C_2$-$C_{12}$ alkenyl, $C_2$-$C_{12}$ alkynyl, cyano, aryl, heteroaryl, alkylaryl, alkylheteroaryl, alkenylaryl, alkenylheteroaryl, alkynylaryl, alkynylheteroaryl, alkoxy, alkenyloxy, alkenyloxy, aryloxy, heteroaryloxy, acyl, alkylhydroxy, alkylamino, alkenylamino, alkynylamino, amido, carboxyl, or carboxyl ester,
or a salt or ester thereof.

6. The compound of claim 5,
wherein X is $C_1$-$C_{12}$ alkyl, $C_2$-$C_{12}$ alkenyl, $C_2$-$C_{12}$ alkynyl.

7. The compound of claim 1 having the structure:

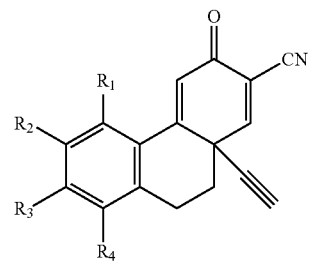

wherein $R_1$, $R_2$, $R_3$ and $R_4$ are each independently, —H, halogen, —CN, —$CF_3$, —$OCF_3$, —($C_1$-$C_{12}$ alkyl), —($C_2$-$C_{12}$ alkenyl), —($C_2$-$C_{12}$ alkynyl), -(aryl), -(heteroaryl), —($C_1$-$C_{12}$ alkyl)-(aryl), —($C_2$-$C_{12}$ alkenyl)-(aryl), —($C_2$-$C_{12}$ alkynyl)-(aryl), —($C_1$-$C_{12}$ alkyl)-(heteroaryl), —($C_2$-$C_{12}$ alkenyl)-(heteroaryl), —($C_2$-$C_{12}$ alkynyl)-(heteroaryl), -(heteroalkyl), -(hydroxyalkyl), -(alkyl)-$NH_2$, —NH-(alkyl), —NH-(alkenyl), —NH-(alkynyl), —NH-(aryl), —NH-(heteroaryl), —OH, —OAc, —$CO_2H$, —$CO_2$-(alkyl), —O—C(O)(alkyl), —O-(alkyl), —O-(alkenyl), —O-(alkynyl), —O-(aryl), —O-(heteroaryl), C(O)—$NH_2$, C(O)—NH-(alkyl), C(O)—NH-(aryl) or C(O)—NH-(heteroaryl),
or a salt or ester thereof.

8. The compound of claim 7,
wherein $R_1$, $R_2$, $R_3$ and $R_4$ are each independently, —H, halogen or —($C_1$-$C_{12}$ alkyl).

9. The compound of claim 1 having the structure:

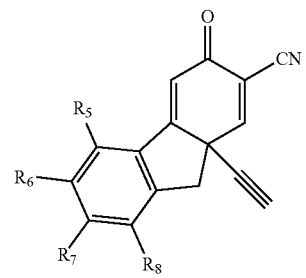

wherein $R_5$, $R_6$, $R_7$ and $R_8$ are each independently, —H, halogen, —CN, —$CF_3$, —$OCF_3$, —($C_1$-$C_{12}$ alkyl), —($C_2$-$C_{12}$ alkenyl), —($C_2$-$C_{12}$ alkynyl), -(aryl), -(heteroaryl), —($C_1$-$C_{12}$ alkyl)-(aryl), —($C_2$-$C_{12}$ alkenyl)-(aryl), —($C_2$-$C_{12}$ alkynyl)-(aryl), —($C_1$-$C_{12}$ alkyl)-(heteroaryl), —($C_2$-$C_{12}$ alkenyl)-(heteroaryl), —($C_2$-$C_{12}$ alkynyl)-(heteroaryl), -(heteroalkyl), -(hydroxyalkyl), -(alkyl)-$NH_2$, —NH-(alkyl), —NH-(alkenyl), —NH-(alkynyl) —NH-(aryl), —NH-(heteroaryl), —OH, —OAc, —CO₂H, —CO₂-(alkyl), —O—C(O)(alkyl), —O-(alkyl), —O-(alkenyl), —O-(alkynyl), —O-(aryl), —O-(heteroaryl), C(O)—NH₂, C(O)—NH-(alkyl), C(O)—NH-(aryl) or C(O)—NH-(heteroaryl), or a salt or ester thereof.

10. The compound of claim 9,
wherein $R_5$, $R_6$, $R_7$ and $R_8$ are each independently, —H, halogen or —($C_1$-$C_{12}$ alkyl).

11. The compound of claim 1 having the structure:

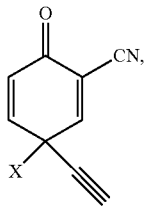

wherein X is $C_2$ alkenyl or $C_2$ alkynyl.

12. A compound having the structure:

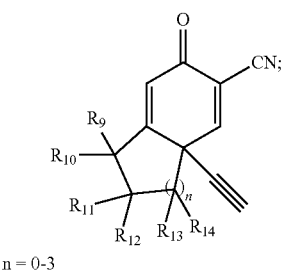

n = 0-3

$R_9$, $R_{10}$, $R_{11}$ and $R_{12}$ are each independently, —H, halogen, —CN, —CF₃, —OCF₃, —($C_1$-$C_{12}$ alkyl), —($C_2$-$C_{12}$ alkenyl), —($C_2$-$C_{12}$ alkynyl), -(aryl), -(heteroaryl), —($C_1$-$C_{12}$ alkyl)-(aryl), —($C_2$-$C_{12}$ alkenyl)-(aryl), —($C_2$-$C_{12}$ alkynyl)-(aryl), —($C_1$-$C_{12}$ alkyl)-(heteroaryl), —($C_2$-$C_{12}$ alkenyl)-(heteroaryl), —($C_2$-$C_{12}$ alkynyl)-(heteroaryl), -(heteroalkyl), -(hydroxyalkyl), -(alkyl)-NH₂, —NH-(alkyl), —NH-(alkenyl), —NH-(alkynyl) —NH-(aryl), —NH-(heteroaryl), —OH, —OAc, —CO₂H, —CO₂-(alkyl), —O—C(O)(alkyl), —O-(alkyl), —O-(alkenyl), —O-(alkynyl), —O-(aryl), —O-(heteroaryl), C(O)—NH₂, C(O)—NH-(alkyl), C(O)—NH-(aryl) or C(O)—NH-(heteroaryl); and each occurrence of $R_{13}$ and $R_{14}$ is each independently, —H, halogen, —CN, —CF₃, —OCF₃, —($C_1$-$C_{12}$ alkyl), —($C_2$-$C_{12}$ alkenyl), —($C_2$-$C_{12}$ alkynyl), -(aryl), -(heteroaryl), —($C_1$-$C_{12}$ alkyl)-(aryl), —($C_2$-$C_{12}$ alkenyl)-(aryl), —($C_2$-$C_{12}$ alkynyl)-(aryl), —($C_1$-$C_{12}$ alkyl)-(heteroaryl), —($C_2$-$C_{12}$ alkenyl)-(heteroaryl), —($C_2$-$C_{12}$ alkynyl)-(heteroaryl), -(heteroalkyl), -(hydroxyalkyl), -(alkyl)-NH₂, —NH-(alkenyl), —NH-(alkynyl) —NH-(aryl), —NH-(heteroaryl), —OH, —OAc, —CO₂H, —CO₂-(alkyl), —O—C(O)(alkyl), —O-(alkyl), —O-(alkenyl), —O-(alkynyl), —O-(aryl), —O-(heteroaryl), C(O)—NH₂, C(O)—NH-(alkyl), C(O)—NH-(aryl) or C(O)—NH-(heteroaryl), wherein when n=2, the cyclohexyl is other than a trisubstituted cyclohexyl bearing CH₃, i-Pr and (CH₂)₂CO₂CH₃ groups or CH₃, i-Pr and (CH₂)₃NH₂ groups, or a salt or ester thereof.

13. The compound of claim 12, wherein n=1, or a salt or ester thereof.

14. The compound of claim 12, wherein n=1 and each occurrence of $R_n$ and $R_{14}$ is —H; or wherein n=2 and each occurrence of $R_{13}$ and $R_{14}$ is —H; or wherein n=3 and each occurrence of $R_n$ and $R_{14}$ is —H, or a salt or ester thereof.

15. The compound of claim 12 having the structure:

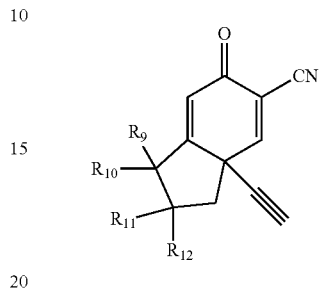

wherein $R_9$, $R_{10}$, $R_{11}$ and $R_{12}$ are each independently, —H, halogen, —CN, —CF₃, —OCF₃, —($C_1$-$C_{12}$ alkyl), —($C_2$-$C_{12}$ alkenyl), —($C_2$-$C_{12}$ alkynyl), -(aryl), -(heteroaryl), —($C_1$-$C_{12}$ alkyl)-(aryl), —($C_2$-$C_{12}$ alkenyl)-(aryl), —($C_2$-$C_{12}$ alkynyl)-(aryl), —($C_1$-$C_{12}$ alkyl)-(heteroaryl), —($C_2$-$C_{12}$ alkenyl)-(heteroaryl), —($C_2$-$C_{12}$ alkynyl)-(heteroaryl), (heteroalkyl), -(hydroxyalkyl), -(alkyl)-NH₂, —NH-(alkyl), —NH-(alkenyl), —NH-(alkynyl) —NH-(aryl), —NH-(heteroaryl), —OH, —OAc, —CO₂H, —CO₂-(alkyl), —O—C(O)(alkyl), —O-(alkyl), —O-(alkenyl), —O-(alkynyl), —O-(aryl), —O-(heteroaryl), C(O)—NH₂, C(O)—NH-(alkyl), C(O)—NH-(aryl) or C(O)—NH-(heteroaryl), or a salt or ester thereof.

16. The compound of claim 15,
wherein $R_9$, $R_{10}$, $R_{11}$ and $R_{12}$ are each independently, —H or —($C_1$-$C_{12}$ alkyl).

17. The compound of claim 1 having the structure:

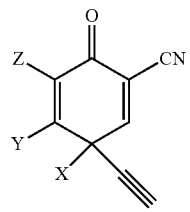

wherein

X is $C_1$-$C_{12}$ alkyl, $C_2$-$C_{12}$ alkenyl or $C_2$-$C_{12}$ alkynyl, or forms an unsubstituted or substituted indane or tetralin with Y, Y is H or forms an unsubstituted or substituted indane or tetralin with X, or forms an unsubstituted or substituted phenyl with Z; and Z is H or forms an unsubstituted or substituted phenyl with Y;

wherein when Z and Y are both H, then X is $C_2$ alkenyl or $C_2$ alkynyl, or a salt or ester thereof.

18. The compound of claim 1 having the structure:

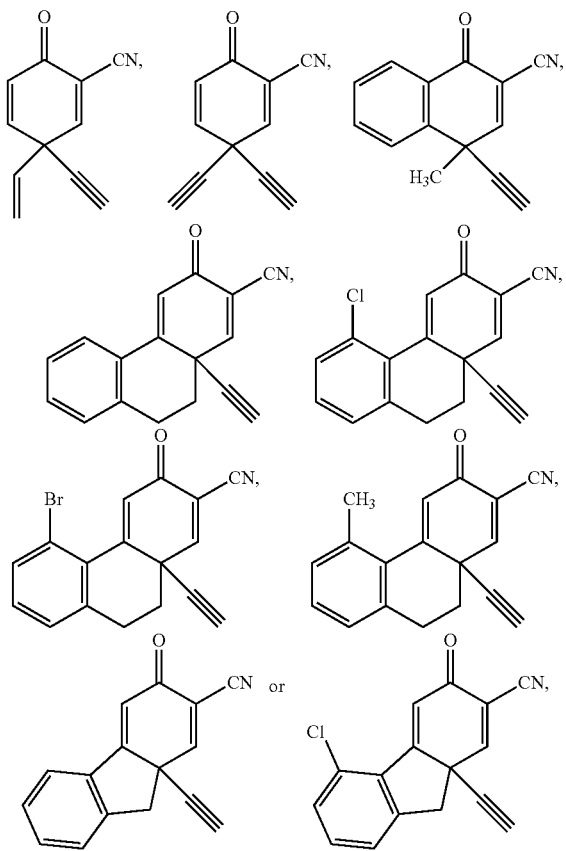

or a salt thereof.

19. A pharmaceutical composition comprising the compound of claim 1 and a pharmaceutically acceptable carrier.

20. A method of treating a subject afflicted with cancer, an inflammatory disease, a neurodegenerative disease, renal disease, kidney disease, a disease characterized by overexpression of COX-2 genes or a disease characterized by overexpression of iNOS genes comprising administering an effective amount of the compound of claim 1 to the subject so as to thereby treat the subject.

21. The compound of claim 12 having the structure:

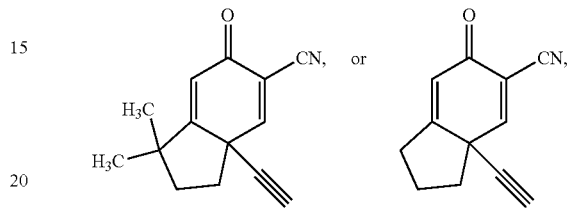

or a salt thereof.

22. A pharmaceutical composition comprising the compound of claim 12 and a pharmaceutically acceptable carrier.

23. A method of treating a subject afflicted with cancer, an inflammatory disease, a neurodegenerative disease, renal disease, kidney disease, a disease characterized by overexpression of COX-2 genes or a disease characterized by overexpression of iNOS genes comprising administering an effective amount of the compound of claim 12 to the subject so as to thereby treat the subject.

* * * * *